(12) United States Patent
Devico et al.

(10) Patent No.: US 7,399,473 B2
(45) Date of Patent: Jul. 15, 2008

(54) VIRUS COAT PROTEIN/RECEPTOR CHIMERAS AND METHOD OF USE

(75) Inventors: Anthony Louis Devico, Alexandria, VA (US); Timothy R. Fouts, Columbia, MD (US); Robert G. Tuskan, Baltimore, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 17 days.

(21) Appl. No.: 11/124,027

(22) Filed: May 6, 2005

(65) Prior Publication Data

US 2005/0221445 A1  Oct. 6, 2005

Related U.S. Application Data

(62) Division of application No. 09/934,060, filed on Aug. 21, 2001, now Pat. No. 6,908,612.

(51) Int. Cl.
*A61K 39/00* (2006.01)
(52) U.S. Cl. .............. 424/185.1; 424/192.1; 424/204.1; 424/207.1; 424/208.1; 435/7.1; 435/69.7; 530/350; 536/23.4
(58) Field of Classification Search ........................ None
See application file for complete search history.

(56) References Cited

U.S. PATENT DOCUMENTS

| | | | |
|---|---|---|---|
| 5,420,030 A | 5/1995 | Reitz, Jr. et al. | |
| 5,518,723 A | 5/1996 | Devico et al. | |
| 5,576,000 A | 11/1996 | Reitz, Jr. et al. | |
| 5,689,313 A | 11/1997 | Sotheran | |
| 5,714,316 A * | 2/1998 | Weiner et al. .................. | 435/6 |
| 5,770,572 A | 6/1998 | Gershoni | |
| 5,843,454 A | 12/1998 | Devico et al. | |
| 5,871,913 A | 2/1999 | Maddon et al. | |
| 5,925,741 A | 7/1999 | Gershoni | |
| 6,020,468 A | 2/2000 | Gershoni | |
| 6,060,316 A * | 5/2000 | Young et al. ................. | 435/455 |
| 6,143,876 A | 11/2000 | Gershoni | |
| 6,165,722 A | 12/2000 | Gershoni et al. | |
| 6,329,202 B1 | 12/2001 | Gershoni | |

FOREIGN PATENT DOCUMENTS

| EP | 0 325 262 A2 | 7/1989 |
|---|---|---|
| WO | WO-92/05799 | 4/1992 |
| WO | WO-93/15750 | 8/1993 |
| WO | WO-94/26305 | 11/1994 |
| WO | WO-98/47916 | 10/1998 |

OTHER PUBLICATIONS

Xu, et al. Virology, 2006, vol. 349, p. 276-289.*
Feinberg and Moore, Nature Medicine, 2002, vol. 8, p. 207-210.*
McMichael and Hanke, Nature Medicine, 2003, vol. 9, p. 874-880.*
Zolla-Pazner, Nature Immunology, 2004, vol. 4, p. 199-210.*
R.A. Kaup et al., "Shutting down HIV," Nature, 370; 416 (1994).
R.A. Kaup et al., "Temporal association of cellular immune responses with the initial control of viremia in primary human immunodeficiency virus type 1 syndrome," Journal of Virol,vol. 68; 4650-4655 (1994).
E.A. Emini, et al., "Prevention of HIB-1 infection in chimpanzees by gp120 V3 domain-specific monoclonal antibody," Nature, vol. 355; 728-739 (1992).
R. Shibata et al., "Neutralizing antibody directed against the HIV-1 envelope glycoprotein can completely block HIV-1/SIV chimeric virus infections of macaque monkeys," Nature Medicine, vol. 5; 204-210 (1999).
M.C. Gauduin et al., "Passive immunization with a human monoclonal antibody protects huPBL-SCID mice against challenge by primary isolates of HIV-1," Nature Medicine, vol. 3; 1389-1393 (1997).
P.W. Parren et al., "Protection against HIV-1 infection in hu-PBL-SCID mice by passive immunization with a neutralizing human monoclonal antibody against the gp120 CD4binding site," AIDS, vol. 9; F1-F6 (1995).
J.W. Eichberg et al., "Prevention of HIV infection by passive immunization with HIVIG or CD4 IgG," AIDS Res. Hum. Retroviruses, vol. 8; 1515 (1992).
R.H. Ward et al, "Prevention of HIV-1 HIB infection in chimpanzees by CD4 immunoadhesin," Nature, vol. 352; 434-436 (1991).
J.L. Heeney et al, "Beta-chemokines and neutralizing antibody titers correlate with sterilizing immunity generated in HIV-1 vaccinated macaques," Proc. Nat. Acad. Sci. U.S.A., 95; 10803-10808 (1998).
Mascola et al., "Protection of macaques against pathogenic simian/human immunodeficiency virus 89.6PD by passive transfer of neutralizing antibodies," Jour. OfVirol., vol. 73; 4009-4018 (1999).
J.P. Moore et al, "HIV-1 neutralization: the consequences of viral adaptation to growth on transformed T cells," AIDS, vol. 9; S117-S136 (1995).
Sells, Mary Ann, et al. "Epitope-tag vectors for eukaryotic protein production." Gene, vol. 152, (1995), pp. 187-189.
Q.J. Sattentau, "Neutralization of HIV01 by antibody," Curr. Opin. Immun., vol. 8; 540-545 (1996).
R. Wyatt et al., "The HIV-1 envelope glycoproteins: fusogens, antigens, and immunogens," Science, vol. 280; 1884-1888 (1998).
Claudio Vita, "Rational engineering of a miniprotein that reproduces the core of the CD4 site interacting with HIV-1 envelope glycoprotein," PNAS, vol. 96, No. 23, pp. 13091-13096 (Nov. 9, 1999).

(Continued)

*Primary Examiner*—Bruce Campell
*Assistant Examiner*—Agnieszka Boesen
(74) *Attorney, Agent, or Firm*—Marianne Fuierer; Moore & Van Allen PLLC

(57) ABSTRACT

The invention relates to chimeric molecules comprising a virus coat sequence and a receptor sequence that can inter-act with each other to form a complex that is capable of binding a co-receptor. Such chimeric molecules therefore exhibit functional properties characteristic of a receptor-coat protein complex and are useful as agents that inhibit virus infection of cells due to occupancy of a co-receptor present on the cell. In particular aspects, the chimeric polypeptide includes an immunodeficiency virus envelope polypeptide, such as that of HIV, SIV, FIV, FeLV, FPV and herpes virus. Receptor sequences suitable for use in a chimeric polypeptide include, for example, CD4 D1D2 and CD4M9 sequences.

11 Claims, 21 Drawing Sheets

OTHER PUBLICATIONS

Fouts et al. "Expression and characterization of a single-chain polypeptide analogue of the human immunodeficiency virus type 1 gp120-CD4receptor complex," Journal of Virology, vol. 74, No. 24, pp. 11427-11436, (Dec. 2000).

Gershoni, et al. "HIV binding to its receptor creates specific epitopes for the CD4/lgp120 complex," FASEB Journal, vol. 7, pp. 1185-1187, (Sep. 1993).

Partidos, et al., "The Influence of Orientation and Number of Copies of T and B Cell Epitopes on the Specificity and Affinity of Antibodies Induced by Chimeric Peptides," European Journal of Immunology, vol. 22, pp. 2675-2680 (1992).

Zeng, et al., "Assembly of Synthetic Peptide Vaccine by Chemoselective Ligation of Epitopes: Influence of Different Chemical Linkages and Epitope Orientations on Biological Activity," Vaccine, vol. 19, pp. 3843-3852 (2001).

Moore, G.J., "Designing Peptide Mimetics," Trends in Protein Science, vol. 15, pp. 124-129 (1994).

Chackerian, et al., "Induction of Antibodies to Mouse CCR5 with Recombinant Papilmavirus Particles," Proceedings of the National Academy of Science, vol. 96, pp. 2373-2378 (Mar. 1999).

Freed, et al., Mutational Analysis of the Cleavage Sequence of the Human Immunodeficiency Virus Type 1 Envelope Glycoprotein Precursor Gp160. *Journal of Virology*, vol. 63, No. 11, pp. 4670-4675 (1989).

Stratagene Catalog, Affinity Protein Expression and Purification System, p. 112, (1997/1998).

DeVico et al, 1996 "Covalently Crosslinked Complexes of Human Immunodefciency Virus Type 1 (HIV-1) gp120 and CD4 Receptor Elicit a Neutralizing Immune Response That Includes Antibodies Selective for Primary Virus Isolates" *Virology* 218, 258-263.

DeVico, et al., 1995, "Monoclonal Antibodies Raised against Covalently Crosslinked Complexes of Human Immunodeficiency Virus Type 1 gp120 and CD4 Receptors Identify a Novel Complex Dependent Epitope on gp120" *Virology* 211, 583-588.

Rizzuto, Carlo D., et al. "A Conserved HIV gp120 Glycoprotein Structure Involved in Chemokine Receptor Binding." Science, vol. 280, (1998), pp. 1949-1953.

Sullivan, Nancy, et al. "CD4-Induced Conformational Changes in the Human Immunodeficiency Virus Type 1 gp120 Glycoprotein: Consequences for Virus Entry and Neutralization." Journal of Virology, (1998), pp. 4694-4703.

* cited by examiner

1. Purified Single Chain
2. Single Chain crosslinked with BS³

SEQUENCE LISTING

<160> NUMBER OF SEQ ID NOS: 33

<210> SEQ ID NO 1
<211> LENGTH: 2159
<212> TYPE: DNA
<213> ORGANISM: Artificial Sequence
<220> FEATURE:
<223> OTHER INFORMATION: Synthetic construct

<400> SEQUENCE: 1

```
atgcccatgg ggtctctgca accgctggcc accttgtacc tgctggggat gctggtcgct      60
tcctgcctcg gaaacgccga ggagaagctg tgggtgaccg tgtactacgg cgtgcccgtg     120
tggaaggagg ccaccaccac cctgttctgc gccagcgacc gcaaggccta cgacaccgag     180
gtgcacaacg tgtgggccac ccacgcctgc gtgccaccg accccaaccc ccaggaggtg      240
gagctgaaga acgtgaccga gaacttcaac atgtggaaga caacatggt ggagcagatg      300 cacgaggaca tcatcagcct gtgggaccag agcctgaagc cctgcgtgaa gctgaccccc     360
ctgtgcgtga ccctgaactg caccgacctg cgcaacgcca ccaacggcaa cgacaccaac     420
accactagta gcagccgcgg catggtgggc ggcggcgaga tgaagaactg cagcttcaac     480
atcaccacca acatccgcgg caaggtgcag aaggagtacg ccctgttcta caagctggac     540
atcgccccca tcgacaacaa cagcaacaac cgctaccgcc tgatcagctg caacaccagc     600
gtgatcaccc aggcctgccc caaggtgagc ttcgagccca tccccatcca ctactgcgcc     660
cccgccggct tcgccatcct gaagtgcaag gacaagaagt tcaacggcaa gggcccctgc     720
accaacgtga gcaccgtgca gtgcacccac ggcatccgcc ccgtggtgag cacccagctg     780
ctgctgaacg gcagcctggc cgaggaggag gtggtgatcc gcagcgccaa cttcgccgac     840
aacgccaagg tgatcatcgt gcagctgaac gagagcgtgg agatcaactg cacccgcccc     900
aacaacaaca cccgcaagtc catccacatc ggccccggcc gcgccttcta caccaccggc     960
gagatcatcg gcgacatccg ccaggcccac tgcaacctga ccgcgccaa gtggaacgac    1020 accctgaaca agatcgtgat caagctgcgc gagcagttcg caacaagac catcgtgttc    1080 aagcacagca gcggcggcga ccccgagatc gtgacccaca gcttcaattg cggcggcgag    1140
ttcttctact gcaacagcac ccagctgttc aacagcacct ggaacgtgac cgaggagagc    1200
aacaacaccg tggagaacaa caccatcacc ctgccctgcc gcatcaagca gatcatcaac    1260
atgtggcagg aggtgggccg cgccatgtac gcccccccca tccgcggcca gatccgctgc    1320
agttchaaca tcaccggcct gctgctgacc cgcgacggcg gccccgagga caacaagacc    1380
gaggtgttcc gccccggcgg cggcgacatg cgcgacaact ggcgcagcga gctgtacaag    1440
tacaaggtgg tgaagatcga gcccctgggc gtggccccca ccaaggccaa gcgccgcgtg    1500
gtgcagcgcg agaagcgtgg atcctctggt ggcggtggct cgggctccgg aggaggtggg    1560
tcgggtggcg gcgcggccgc taagaaagtg gtgctgggca aaaaggggga tacagtggaa    1620
ctgacctgta cagcttccca gaagaagagc atacaattcc actggaaaaa ctccaaccag    1680
ataaagattc tgggaaatca gggctccttc ttaactaaag gtccatccaa gctgaatgat    1740
cgcgctgact caagaagaag cctttgggac caaggaaact tcccctgat catcaagaat    1800
```

-continued

```
cttaagatag aagactcaga tacttacatc tgtgaagtgg aggaccagaa ggaggaggtg   1860
caattgctag tgttcggatt gactgccaac tctgacaccc acctgcttca ggggcagagc   1920
ctgaccctga ccttggagag ccccctggt agtagcccct cagtgcaatg taggagtcca    1980
aggggtaaaa acatacaggg ggggaagacc ctctccgtgt ctcagctgga gctccaggat   2040
agtggcacct ggacatgcac tgtcttgcag aaccagaaga aggtggagtt caaaatagac   2100
atcgtggtgc tagctgaaca aaaactcatc tcagaagagg atctgtaata tgtttaaac    2159
```

<210> SEQ ID NO 2
<211> LENGTH: 720
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (716)..(716)
<223> OTHER INFORMATION: Xaa can be any amino acid
<220> FEATURE:
<221> NAME/KEY: MISC_FEATURE
<222> LOCATION: (719)..(719)
<223> OTHER INFORMATION: Xaa can be any amino acid

<400> SEQUENCE: 2

```
Met Pro Met Gly Ser Leu Gln Pro Leu Ala Thr Leu Tyr Leu Leu Gly
1               5                   10                  15

Met Leu Val Ala Ser Cys Leu Gly Asn Ala Glu Glu Lys Leu Trp Val
            20                  25                  30

Thr Val Tyr Tyr Gly Val Pro Val Trp Lys Glu Ala Thr Thr Thr Leu
        35                  40                  45

Phe Cys Ala Ser Asp Arg Lys Ala Tyr Asp Thr Glu Val His Asn Val
    50                  55                  60

Trp Ala Thr His Ala Cys Val Pro Thr Asp Pro Asn Pro Gln Glu Val
65                  70                  75                  80

Glu Leu Lys Asn Val Thr Glu Asn Phe Asn Met Trp Lys Asn Asn Met
                85                  90                  95

Val Glu Gln Met His Glu Asp Ile Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asp Leu Arg Asn Ala Thr Asn Gly Asn Asp Thr Asn Thr Thr Ser Ser
    130                 135                 140

Ser Arg Gly Met Val Gly Gly Glu Met Lys Asn Cys Ser Phe Asn
145                 150                 155                 160

Ile Thr Thr Asn Ile Arg Gly Lys Val Gln Lys Glu Tyr Ala Leu Phe
                165                 170                 175

Tyr Lys Leu Asp Ile Ala Pro Ile Asp Asn Asn Ser Asn Asn Arg Tyr
            180                 185                 190

Arg Leu Ile Ser Cys Asn Thr Ser Val Ile Thr Gln Ala Cys Pro Lys
        195                 200                 205

Val Ser Phe Glu Pro Ile Pro Ile His Tyr Cys Ala Pro Ala Gly Phe
    210                 215                 220

Ala Ile Leu Lys Cys Lys Asp Lys Lys Phe Asn Gly Lys Gly Pro Cys
225                 230                 235                 240

Thr Asn Val Ser Thr Val Gln Cys Thr His Gly Ile Arg Pro Val Val
                245                 250                 255
```

-continued

```
Ser Thr Gln Leu Leu Asn Gly Ser Leu Ala Glu Glu Val Val
        260                 265                 270

Ile Arg Ser Ala Asn Phe Ala Asp Asn Ala Lys Val Ile Val Gln
            275                 280                 285

Leu Asn Glu Ser Val Glu Ile Asn Cys Thr Arg Pro Asn Asn Thr
        290                 295                 300

Arg Lys Ser Ile His Ile Gly Pro Gly Arg Ala Phe Tyr Thr Thr Gly
305                 310                 315                 320

Glu Ile Ile Gly Asp Ile Arg Gln Ala His Cys Asn Leu Ser Arg Ala
                325                 330                 335

Lys Trp Asn Asp Thr Leu Asn Lys Ile Val Ile Lys Leu Arg Glu Gln
                340                 345                 350

Phe Gly Asn Lys Thr Ile Val Phe Lys His Ser Ser Gly Gly Asp Pro
            355                 360                 365

Glu Ile Val Thr His Ser Phe Asn Cys Gly Gly Glu Phe Phe Tyr Cys
        370                 375                 380

Asn Ser Thr Gln Leu Phe Asn Ser Thr Trp Asn Val Thr Glu Glu Ser
385                 390                 395                 400

Asn Asn Thr Val Glu Asn Asn Thr Ile Thr Leu Pro Cys Arg Ile Lys
                405                 410                 415

Gln Ile Ile Asn Met Trp Gln Glu Val Gly Arg Ala Met Tyr Ala Pro
                420                 425                 430

Pro Ile Arg Gly Gln Ile Arg Cys Ser Ser Asn Ile Thr Gly Leu Leu
            435                 440                 445

Leu Thr Arg Asp Gly Gly Pro Glu Asp Asn Lys Thr Glu Val Phe Arg
        450                 455                 460

Pro Gly Gly Gly Asp Met Arg Asp Asn Trp Arg Ser Glu Leu Tyr Lys
465                 470                 475                 480

Tyr Lys Val Val Lys Ile Glu Pro Leu Gly Val Ala Pro Thr Lys Ala
                485                 490                 495

Lys Arg Arg Val Val Gln Arg Glu Lys Arg Gly Ser Ser Gly Gly Gly
            500                 505                 510

Gly Ser Gly Ser Gly Gly Gly Ser Gly Gly Ala Ala Ala Lys
        515                 520                 525

Lys Val Val Leu Gly Lys Lys Gly Asp Thr Val Glu Leu Thr Cys Thr
        530                 535                 540

Ala Ser Gln Lys Lys Ser Ile Gln Phe His Trp Lys Asn Ser Asn Gln
545                 550                 555                 560

Ile Lys Ile Leu Gly Asn Gln Gly Ser Phe Leu Thr Lys Gly Pro Ser
            565                 570                 575

Lys Leu Asn Asp Arg Ala Asp Ser Arg Arg Ser Leu Trp Asp Gln Gly
        580                 585                 590

Asn Phe Pro Leu Ile Ile Lys Asn Leu Lys Ile Glu Asp Ser Asp Thr
            595                 600                 605

Tyr Ile Cys Glu Val Glu Asp Gln Lys Glu Glu Val Gln Leu Leu Val
        610                 615                 620

Phe Gly Leu Thr Ala Asn Ser Asp Thr His Leu Leu Gln Gly Gln Ser
625                 630                 635                 640

Leu Thr Leu Thr Leu Glu Ser Pro Pro Gly Ser Ser Pro Ser Val Gln
                645                 650                 655

Cys Arg Ser Pro Arg Gly Lys Asn Ile Gln Gly Gly Lys Thr Leu Ser
            660                 665                 670
```

-continued

```
Val Ser Gln Leu Glu Leu Gln Asp Ser Gly Thr Trp Thr Cys Thr Val
        675                 680                 685

Leu Gln Asn Gln Lys Lys Val Glu Phe Lys Ile Asp Ile Val Val Leu
    690                 695                 700

Ala Glu Gln Lys Leu Ile Ser Glu Glu Asp Leu Xaa Tyr Val Xaa Thr
705                 710                 715                 720

<210> SEQ ID NO 3
<211> LENGTH: 2159
<212> TYPE: DNA
<213> ORGANISM: Artificial Sequence
<220> FEATURE:
<223> OTHER INFORMATION: Synthetic construct

<400> SEQUENCE: 3
atgcccatgg ggtctctgca accgctggcc accttgtacc tgctggggat gctggtcgct      60
tcctgcctcg gaaacgccga ggagaagctg tgggtgaccg tgtactacgg cgtgcccgtg     120
tggaaggagg ccaccaccac cctgttctgc gccagcgacg caaggcccta cgacaccgag     180
gtgcacaacg tgtgggccac ccacgcctgc gtgcccaccg accccaaccc ccaggaggtg     240
gagctgaaga acgtgaccga gaacttcaac atgtggaaga caacatggt ggagcagatg      300 cacgaggaca tcatcagcct gtgggaccag agcctgaagc cctgcgtgaa gctgacccc      360 ctgtgcgtga ccctgaactg caccgacctg cgcaacgcca ccaacggcaa cgacaccaac     420
accactagta gcagccgcgg catggtgggc ggcggcgaga tgaagaactg cagcttcaac     480
atcaccacca acatccgcgg caaggtgcag aaggagtacg ccctgttcta caagctggac     540
atcgccccca tcgacaacaa cagcaacaac cgctaccgcc tgatcagctg caacaccagc     600
gtgatcaccc aggcctgccc caaggtgagc ttcgagccca tccccatcca ctactgcgcc     660
cccgccggct tcgccatcct gaagtgcaag gacaagaagt tcaacggcaa gggcccctgc     720
accaacgtga gcaccgtgca gtgcacccac ggcatccgcc ccgtggtgag cacccagctg     780
ctgctgaacg gcagcctggc cgaggaggag gtggtgatcc gcagcgccaa cttcgccgac     840
aacgccaagg tgatcatcgt gcagctgaac gagagcgtgg agatcaactg cacccgcccc     900
aacaacaaca cccgcaagtc catccacatc ggccccggcc gcgccttcta caccaccggc     960
gagatcatcg gcgacatccg ccaggcccac tgcaacctga gccgcgccaa gtggaacgac    1020 acccctgaaca agatcgtgat caagctgcgc gagcagttcg caacaagac catcgtgttc    1080 aagcacagca gcggcggcga ccccgagatc gtgacccaca gcttcaattg cggcggcgag    1140
ttcttctact gcaacagcac ccagctgttc aacagcacct ggaacgtgac cgaggagagc    1200
aacaacaccg tggagaacaa caccatcacc ctgccctgcc gcatcaagca gatcatcaac    1260
atgtggcagg aggtgggccg cgccatgtac gccccccca tccgcggcca gatccgctgc    1320
agttchaaca tcaccggcct gctgctgacc cgcgacggcg gccccgagga caacaagacc    1380
gaggtgttcc gccccggcgg cggcgacatg cgcgacaact ggcgcagcga gctgtacaag    1440
tacaaggtgg tgaagatcga gcccctgggc gtggccccca ccaaggccaa cgccgcgtg    1500 gtgcagcgcg agaagaccgg atcctctggt ggcggtggct cgggctccgg aggaggtggg    1560
tcgggtggcg gcgcggccgc taagaaagtg gtgctgggca aaaaggggga tacagtggaa    1620
ctgacctgta cagcttccca gaagaagagc atacaattcc actggaaaaa ctccaaccag    1680
ataaagattc tgggaaatca gggctccttc ttaactaaag gtccatccaa gctgaatgat    1740
cgcgctgact caagaagaag cctttgggac caaggaaact ccccctgat catcaagaat    1800
```

-continued

```
cttaagatag aagactcaga tacttacatc tgtgaagtgg aggaccagaa ggaggaggtg   1860
caattgctag tgttcggatt gactgccaac tctgacaccc acctgcttca ggggcagagc   1920
ctgaccctga ccttggagag ccccctggt agtagcccct cagtgcaatg taggagtcca   1980
aggggtaaaa acatacaggg ggggaagacc ctctccgtgt ctcagctgga gctccaggat   2040
agtggcacct ggacatgcac tgtcttgcag aaccagaaga aggtggagtt caaaatagac   2100
atcgtggtgc tagctgaaca aaaactcatc tcagaagagg atctgtaata tgtttaaac    2159
```

<210> SEQ ID NO 4
<211> LENGTH: 720
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (716)..(716)
<223> OTHER INFORMATION: Xaa can be any amino acid
<220> FEATURE:
<221> NAME/KEY: MISC_FEATURE
<222> LOCATION: (719)..(719)
<223> OTHER INFORMATION: Xaa can be any amino acid

<400> SEQUENCE: 4

```
Met Pro Met Gly Ser Leu Gln Pro Leu Ala Thr Leu Tyr Leu Leu Gly
1               5                   10                  15

Met Leu Val Ala Ser Cys Leu Gly Asn Ala Glu Glu Lys Leu Trp Val
                20                  25                  30

Thr Val Tyr Tyr Gly Val Pro Val Trp Lys Glu Ala Thr Thr Thr Leu
            35                  40                  45

Phe Cys Ala Ser Asp Arg Lys Ala Tyr Asp Thr Glu Val His Asn Val
        50                  55                  60

Trp Ala Thr His Ala Cys Val Pro Thr Asp Pro Asn Pro Gln Glu Val
65                  70                  75                  80

Glu Leu Lys Asn Val Thr Glu Asn Phe Asn Met Trp Lys Asn Asn Met
                85                  90                  95

Val Glu Gln Met His Glu Asp Ile Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asp Leu Arg Asn Ala Thr Asn Gly Asn Asp Thr Asn Thr Thr Ser Ser
    130                 135                 140

Ser Arg Gly Met Val Gly Gly Glu Met Lys Asn Cys Ser Phe Asn
145                 150                 155                 160

Ile Thr Thr Asn Ile Arg Gly Lys Val Gln Lys Glu Tyr Ala Leu Phe
                165                 170                 175

Tyr Lys Leu Asp Ile Ala Pro Ile Asp Asn Asn Ser Asn Asn Arg Tyr
            180                 185                 190

Arg Leu Ile Ser Cys Asn Thr Ser Val Ile Thr Gln Ala Cys Pro Lys
        195                 200                 205

Val Ser Phe Glu Pro Ile Pro Ile His Tyr Cys Ala Pro Ala Gly Phe
    210                 215                 220

Ala Ile Leu Lys Cys Lys Asp Lys Phe Asn Gly Lys Gly Pro Cys
225                 230                 235                 240

Thr Asn Val Ser Thr Val Gln Cys Thr His Gly Ile Arg Pro Val Val
                245                 250                 255
```

-continued

```
Ser Thr Gln Leu Leu Asn Gly Ser Leu Ala Glu Glu Val Val
            260                 265                 270

Ile Arg Ser Ala Asn Phe Ala Asp Asn Ala Lys Val Ile Val Gln
            275                 280                 285

Leu Asn Glu Ser Val Glu Ile Asn Cys Thr Arg Pro Asn Asn Asn Thr
            290                 295                 300

Arg Lys Ser Ile His Ile Gly Pro Gly Arg Ala Phe Tyr Thr Thr Gly
305                 310                 315                 320

Glu Ile Ile Gly Asp Ile Arg Gln Ala His Cys Asn Leu Ser Arg Ala
                    325                 330                 335

Lys Trp Asn Asp Thr Leu Asn Lys Ile Val Ile Lys Leu Arg Glu Gln
                    340                 345                 350

Phe Gly Asn Lys Thr Ile Val Phe Lys His Ser Ser Gly Gly Asp Pro
                    355                 360                 365

Glu Ile Val Thr His Ser Phe Asn Cys Gly Gly Glu Phe Phe Tyr Cys
    370                 375                 380

Asn Ser Thr Gln Leu Phe Asn Ser Thr Trp Asn Val Thr Glu Glu Ser
385                 390                 395                 400

Asn Asn Thr Val Glu Asn Asn Thr Ile Thr Leu Pro Cys Arg Ile Lys
                    405                 410                 415

Gln Ile Ile Asn Met Trp Gln Glu Val Gly Arg Ala Met Tyr Ala Pro
                    420                 425                 430

Pro Ile Arg Gly Gln Ile Arg Cys Ser Ser Asn Ile Thr Gly Leu Leu
                    435                 440                 445

Leu Thr Arg Asp Gly Gly Pro Glu Asp Asn Lys Thr Glu Val Phe Arg
            450                 455                 460

Pro Gly Gly Gly Asp Met Arg Asp Asn Trp Arg Ser Glu Leu Tyr Lys
465                 470                 475                 480

Tyr Lys Val Val Lys Ile Glu Pro Leu Gly Val Ala Pro Thr Lys Ala
                    485                 490                 495

Lys Arg Arg Val Val Gln Arg Glu Lys Thr Gly Ser Ser Gly Gly Gly
            500                 505                 510

Gly Ser Gly Ser Gly Gly Gly Ser Gly Gly Ala Ala Ala Lys
            515                 520                 525

Lys Val Val Leu Gly Lys Lys Gly Asp Thr Val Glu Leu Thr Cys Thr
530                 535                 540

Ala Ser Gln Lys Lys Ser Ile Gln Phe His Trp Lys Asn Ser Asn Gln
545                 550                 555                 560

Ile Lys Ile Leu Gly Asn Gln Gly Ser Phe Leu Thr Lys Gly Pro Ser
            565                 570                 575

Lys Leu Asn Asp Arg Ala Asp Ser Arg Arg Ser Leu Trp Asp Gln Gly
            580                 585                 590

Asn Phe Pro Leu Ile Ile Lys Asn Leu Lys Ile Glu Asp Ser Asp Thr
            595                 600                 605

Tyr Ile Cys Glu Val Glu Asp Gln Lys Glu Glu Val Gln Leu Leu Val
    610                 615                 620

Phe Gly Leu Thr Ala Asn Ser Asp Thr His Leu Leu Gln Gly Gln Ser
625                 630                 635                 640

Leu Thr Leu Thr Leu Glu Ser Pro Pro Gly Ser Ser Pro Ser Val Gln
            645                 650                 655

Cys Arg Ser Pro Arg Gly Lys Asn Ile Gln Gly Gly Lys Thr Leu Ser
            660                 665                 670
```

```
Val Ser Gln Leu Glu Leu Gln Asp Ser Gly Thr Trp Thr Cys Thr Val
        675                 680                 685

Leu Gln Asn Gln Lys Lys Val Glu Phe Lys Ile Asp Ile Val Val Leu
    690                 695                 700

Ala Glu Gln Lys Leu Ile Ser Glu Glu Asp Leu Xaa Tyr Val Xaa Thr
705                 710                 715                 720

<210> SEQ ID NO 5
<211> LENGTH: 1668
<212> TYPE: DNA
<213> ORGANISM: Artificial Sequence
<220> FEATURE:
<223> OTHER INFORMATION: Synthetic construct

<400> SEQUENCE: 5
atgcccatgg ggtctctgca accgctggcc accttgtacc tgctggggat gctggtcgct     60
tcctgcctcg gaaacgccga ggagaagctg tgggtgaccg tgtactacgg cgtgcccgtg    120
tggaaggagg ccaccaccac cctgttctgc gccagcgacc gcaaggccta cgacaccgag    180
gtgcacaacg tgtgggccac ccacgcctgc gtgccaccg accccaaccc ccaggaggtg    240
gagctgaaga cgtgaccga gaacttcaac atgtggaaga caacatggt ggagcagatg    300 cacgaggaca tcatcagcct gtgggaccag agcctgaagc cctgcgtgaa gctgacccc    360 ctgtgcgtga ccctgaactg caccgacctg cgcaacgcca ccaacggcaa cgacaccaac    420
accactagta gcagccgcgg catggtgggc ggcggcgaga tgaagaactg cagcttcaac    480
atcaccacca acatccgcgg caaggtgcag aaggagtacg ccctgttcta caagctggac    540
atcgccccca tcgacaacaa cagcaacaac cgctaccgcc tgatcagctg caacaccagc    600
gtgatcaccc aggcctgccc caaggtgagc ttcgagccca tccccatcca ctactgcgcc    660
cccgccggct cgccatcct gaagtgcaag acaagaagt tcaacggcaa gggcccctgc    720
accaacgtga gcaccgtgca gtgcacccac ggcatccgcc ccgtggtgag cacccagctg    780
ctgctgaacg gcagcctggc cgaggaggag gtggtgatcc gcagcgccaa cttcgccgac    840
aacgccaagg tgatcatcgt gcagctgaac gagagcgtgg agatcaactg cacccgcccc    900
aacaacaaca cccgcaagtc catccacatc ggccccggcc gcgccttcta caccaccggc    960
gagatcatcg gcgacatccg ccaggcccac tgcaacctga gccgcgccaa gtggaacgac   1020
accctgaaca gatcgtgat caagctgcgc gagcagttcg caacaagac catcgtgttc   1080 aagcacagca gcggcggcga ccccgagatc gtgacccaca gcttcaattg cggcggcgag   1140
ttcttctact gcaacagcac ccagctgttc aacagcacct ggaacgtgac cgaggagagc   1200
aacaacaccg tggagaacaa caccatcacc ctgccctgcc gcatcaagca gatcatcaac   1260
atgtggcagg aggtgggccg cgccatgtac gccccccca tccgcggcca gatccgctgc   1320
agttchaaca tcaccggcct gctgctgacc cgcgacggcg gccccgagga caacaagacc   1380
gaggtgttcc gccccggcgg cggcgacatg cgcgacaact ggcgcagcga gctgtacaag   1440
tacaaggtgg tgaagatcga gcccctgggc gtggcccca ccaaggccaa cgccgcgtg   1500 gtgcagcgcg agaagaccgg atcctctggt ggcggtggct cgggctccgg aggaggtggg   1560
tcgggtggcg gcgcggccgc ttgcaacctg gcccgctgcc agctgcgctg caagagcctg   1620
ggcctgctgg gcaagtgcgc cggcagcttc tgcgcctgcg gcccctaa              1668
```

-continued

```
<210> SEQ ID NO 6
<211> LENGTH: 556
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (556)..(556)
<223> OTHER INFORMATION: Xaa can be any amino acid

<400> SEQUENCE: 6

Met Pro Met Gly Ser Leu Gln Pro Leu Ala Thr Leu Tyr Leu Leu Gly
 1               5                  10                  15

Met Leu Val Ala Ser Cys Leu Gly Asn Ala Glu Glu Lys Leu Trp Val
                20                  25                  30

Thr Val Tyr Tyr Gly Val Pro Val Trp Lys Glu Ala Thr Thr Thr Leu
            35                  40                  45

Phe Cys Ala Ser Asp Arg Lys Ala Tyr Asp Thr Glu Val His Asn Val
        50                  55                  60

Trp Ala Thr His Ala Cys Val Pro Thr Asp Pro Asn Pro Gln Glu Val
 65                 70                  75                  80

Glu Leu Lys Asn Val Thr Glu Asn Phe Asn Met Trp Lys Asn Asn Met
                85                  90                  95

Val Glu Gln Met His Glu Asp Ile Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asp Leu Arg Asn Ala Thr Asn Gly Asn Asp Thr Asn Thr Thr Ser Ser
    130                 135                 140

Ser Arg Gly Met Val Gly Gly Glu Met Lys Asn Cys Ser Phe Asn
145                 150                 155                 160

Ile Thr Thr Asn Ile Arg Gly Lys Val Gln Lys Glu Tyr Ala Leu Phe
                165                 170                 175

Tyr Lys Leu Asp Ile Ala Pro Ile Asp Asn Asn Ser Asn Asn Arg Tyr
            180                 185                 190

Arg Leu Ile Ser Cys Asn Thr Ser Val Ile Thr Gln Ala Cys Pro Lys
        195                 200                 205

Val Ser Phe Glu Pro Ile Pro Ile His Tyr Cys Ala Pro Ala Gly Phe
    210                 215                 220

Ala Ile Leu Lys Cys Lys Asp Lys Lys Phe Asn Gly Lys Gly Pro Cys
225                 230                 235                 240

Thr Asn Val Ser Thr Val Gln Cys Thr His Gly Ile Arg Pro Val Val
                245                 250                 255

Ser Thr Gln Leu Leu Leu Asn Gly Ser Leu Ala Glu Glu Val Val
            260                 265                 270

Ile Arg Ser Ala Asn Phe Ala Asp Asn Ala Lys Val Ile Ile Val Gln
        275                 280                 285

Leu Asn Glu Ser Val Glu Ile Asn Cys Thr Arg Pro Asn Asn Asn Thr
    290                 295                 300

Arg Lys Ser Ile His Ile Gly Pro Gly Arg Ala Phe Tyr Thr Thr Gly
305                 310                 315                 320

Glu Ile Ile Gly Asp Ile Arg Gln Ala His Cys Asn Leu Ser Arg Ala
                325                 330                 335

Lys Trp Asn Asp Thr Leu Asn Lys Ile Val Ile Lys Leu Arg Glu Gln
            340                 345                 350
```

-continued

```
Phe Gly Asn Lys Thr Ile Val Phe Lys His Ser Ser Gly Gly Asp Pro
            355                 360                 365
Glu Ile Val Thr His Ser Phe Asn Cys Gly Gly Glu Phe Phe Tyr Cys
        370                 375                 380
Asn Ser Thr Gln Leu Phe Asn Ser Thr Trp Asn Val Thr Glu Glu Ser
385                 390                 395                 400
Asn Asn Thr Val Glu Asn Asn Thr Ile Thr Leu Pro Cys Arg Ile Lys
                405                 410                 415
Gln Ile Ile Asn Met Trp Gln Glu Val Gly Arg Ala Met Tyr Ala Pro
            420                 425                 430
Pro Ile Arg Gly Gln Ile Arg Cys Ser Ser Asn Ile Thr Gly Leu Leu
        435                 440                 445
Leu Thr Arg Asp Gly Gly Pro Glu Asp Asn Lys Thr Glu Val Phe Arg
    450                 455                 460
Pro Gly Gly Gly Asp Met Arg Asp Asn Trp Arg Ser Glu Leu Tyr Lys
465                 470                 475                 480
Tyr Lys Val Val Lys Ile Glu Pro Leu Gly Val Ala Pro Thr Lys Ala
                485                 490                 495
Lys Arg Arg Val Val Gln Arg Glu Lys Thr Gly Ser Ser Gly Gly Gly
            500                 505                 510
Gly Ser Gly Ser Gly Gly Gly Ser Gly Gly Ala Ala Ala Cys
        515                 520                 525
Asn Leu Ala Arg Cys Gln Leu Arg Cys Lys Ser Leu Gly Leu Leu Gly
    530                 535                 540
Lys Cys Ala Gly Ser Phe Cys Ala Cys Gly Pro Xaa
545                 550                 555

<210> SEQ ID NO 7
<211> LENGTH: 39
<212> TYPE: DNA
<213> ORGANISM: Artificial Sequence
<220> FEATURE:
<223> OTHER INFORMATION: Synthetic construct
<220> FEATURE:
<221> NAME/KEY: primer_bind
<222> LOCATION: (1)..(39)

<400> SEQUENCE: 7
gggggtacca tgcccatggg gtctctgcaa ccgctggcc                          39

<210> SEQ ID NO 8
<211> LENGTH: 66
<212> TYPE: DNA
<213> ORGANISM: Artificial Sequence
<220> FEATURE:
<223> OTHER INFORMATION: Synthetic construct

<400> SEQUENCE: 8
gggtccggag cccgagccac cgccaccaga ggatccacgc ttctcgcgct gcaccacgcg   60
gcgctt                                                             66

<210> SEQ ID NO 9
<211> LENGTH: 69
<212> TYPE: DNA
<213> ORGANISM: Artificial Sequence
<220> FEATURE:
<223> OTHER INFORMATION: Synthetic construct
<220> FEATURE:
<221> NAME/KEY: primer_bind
<222> LOCATION: (1)..(69)
```

```
<400> SEQUENCE: 9
gggtccggag gaggtgggtc gggtggcggc gcggccgcta agaaagtggt gctgggcaaa      60
aaaggggat                                                              69

<210> SEQ ID NO 10
<211> LENGTH: 76
<212> TYPE: DNA
<213> ORGANISM: Artificial Sequence
<220> FEATURE:
<223> OTHER INFORMATION: Synthetic  construct
<220> FEATURE:
<221> NAME/KEY: primer_bind
<222> LOCATION: (1)..(76)

<400> SEQUENCE: 10
ggggtttaaa cttattacag atcctcttct gagatgagtt ttgttcagct agcaccacga      60
tgtctatttt gaactc                                                      76

<210> SEQ ID NO 11
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(21)
<223> OTHER INFORMATION: Spacer

<400> SEQUENCE: 11
gssggggsgs ggggsgggaa a                                                21

<210> SEQ ID NO 12
<211> LENGTH: 1769
<212> TYPE: DNA
<213> ORGANISM: Artificial Sequence
<220> FEATURE:
<223> OTHER INFORMATION: Synthetic construct

<400> SEQUENCE: 12
atgcccatgg ggtctctgca accgctggcc accttgtacc tgctggggat gctggtcgct      60
tcctgcctcg gaaagaacgt gaccgagaac ttcaacatgt ggaagaacaa catggtggag     120
cagatgcacg aggacatcat cagcctgtgg gaccagagcc tgaagccctg cgtgaagctg     180 accccccctgt gcgtgaccct gggcgcgggc gagatgaaga actgcagctt caacatcggc     240
gcgggccgcc tgatcagctg caacaccagc gtgatcaccc aggcctgccc caaggtgagc     300
ttcgagccca tccccatcca ctactgcgcc ccgccggct tcgccatcct gaagtgcaag     360
gacaagaagt tcaacggcaa gggcccctgc accaacgtga gcaccgtgca gtgcacccac     420
ggcatccgcc ccgtggtgag cacccagctg ctgctgaacg gcagcctggc cgaggaggag     480
gtggtgatcc gcagcgccaa cttcgccgac aacgccaagg tgatcatcgt gcagctgaac     540
gagagcgtgg agatcaactg cacccgcccc aacaacaaca cccgcaagtc catccacatc     600
ggccccggcc gcgccttcta caccaccggc gagatcatcg gcgacatccg ccaggccac     660 tgcaacctga gccgcgccaa gtggaacgac accctgaaca agatcgtgat caagctgcgc     720
gagcagttcg gcaacaagac catcgtgttc aagcacagca gcggcggcga ccccgagatc     780
gtgacccaca gcttcaattg cggcggcgag ttcttctact gcaacagcac ccagctgttc     840
aacagcacct ggaacgtgac cgaggagagc aacaacaccg tggagaacaa caccatcacc     900
```

-continued

```
ctgccctgcc gcatcaagca gatcatcaac atgtggcagg aggtgggccg cgccatgtac    960
gcccccccca tccgcggcca gatccgctgc agttchaaca tcaccggcct gctgctgacc   1020
cgcgacggcg gccccgagga caacaagacc gaggtgttcc gccccggcgg cggcgacatg   1080
cgcgacaact ggcgcagcga gctgtacaag tacaaggtgg tgaagatcgg atcctctggt   1140
ggcggtggct cgggctccgg aggaggtggg tcgggtggcg gcgcggccgc taagaaagtg   1200
gtgctgggca aaaaggggga tacagtggaa ctgacctgta cagcttccca gaagaagagc   1260
atacaattcc actggaaaaa ctccaaccag ataaagattc tgggaaatca gggctccttc   1320
ttaactaaag gtccatccaa gctgaatgat cgcgctgact caagaagaag cctttgggac   1380
caaggaaact tccccctgat catcaagaat cttaagatag aagactcaga tacttacatc   1440
tgtgaagtgg aggaccagaa ggaggaggtg caattgctag tgttcggatt gactgccaac   1500
tctgacaccc acctgcttca ggggcagagc ctgaccctga ccttggagag ccccccctggt   1560 agtagcccct cagtgcaatg taggagtcca aggggtaaaa acatacaggg ggggaagacc   1620
ctctccgtgt ctcagctgga gctccaggat agtggcacct ggacatgcac tgtcttgcag   1680
aaccagaaga aggtggagtt caaaatagac atcgtggtgc tagctgaaca aaaactcatc   1740
tcagaagagg atctgtaata tgtttaaac                                     1769
```

<210> SEQ ID NO 13
<211> LENGTH: 590
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (586)..(586)
<223> OTHER INFORMATION: Xaa can be any amino acid
<220> FEATURE:
<221> NAME/KEY: MISC_FEATURE
<222> LOCATION: (589)..(589)
<223> OTHER INFORMATION: Xaa can be any amino acid

<400> SEQUENCE: 13

```
Met Pro Met Gly Ser Leu Gln Pro Leu Ala Thr Leu Tyr Leu Leu Gly
1               5                   10                  15

Met Leu Val Ala Ser Cys Leu Gly Lys Asn Val Thr Glu Asn Phe Asn
            20                  25                  30

Met Trp Lys Asn Asn Met Val Glu Gln Met His Glu Asp Ile Ile Ser
        35                  40                  45

Leu Trp Asp Gln Ser Leu Lys Pro Cys Val Lys Leu Thr Pro Leu Cys
    50                  55                  60

Val Thr Leu Gly Ala Gly Glu Met Lys Asn Cys Ser Phe Asn Ile Gly
65                  70                  75                  80

Ala Gly Arg Leu Ile Ser Cys Asn Thr Ser Val Ile Thr Gln Ala Cys
                85                  90                  95

Pro Lys Val Ser Phe Glu Pro Ile Pro Ile His Tyr Cys Ala Pro Ala
            100                 105                 110

Gly Phe Ala Ile Leu Lys Cys Lys Asp Lys Lys Phe Asn Gly Lys Gly
        115                 120                 125

Pro Cys Thr Asn Val Ser Thr Val Gln Cys Thr His Gly Ile Arg Pro
    130                 135                 140

Val Val Ser Thr Gln Leu Leu Leu Asn Gly Ser Leu Ala Glu Glu Glu
145                 150                 155                 160
```

-continued

```
Val Val Ile Arg Ser Ala Asn Phe Ala Asp Asn Ala Lys Val Ile Ile
            165                 170                 175

Val Gln Leu Asn Glu Ser Val Glu Ile Asn Cys Thr Arg Pro Asn Asn
        180                 185                 190

Asn Thr Arg Lys Ser Ile His Ile Gly Pro Gly Arg Ala Phe Tyr Thr
        195                 200                 205

Thr Gly Glu Ile Ile Gly Asp Ile Arg Gln Ala His Cys Asn Leu Ser
    210                 215                 220

Arg Ala Lys Trp Asn Asp Thr Leu Asn Lys Ile Val Ile Lys Leu Arg
225                 230                 235                 240

Glu Gln Phe Gly Asn Lys Thr Ile Val Phe Lys His Ser Ser Gly Gly
                245                 250                 255

Asp Pro Glu Ile Val Thr His Ser Phe Asn Cys Gly Gly Glu Phe Phe
            260                 265                 270

Tyr Cys Asn Ser Thr Gln Leu Phe Asn Ser Thr Trp Asn Val Thr Glu
        275                 280                 285

Glu Ser Asn Asn Thr Val Glu Asn Asn Thr Ile Thr Leu Pro Cys Arg
    290                 295                 300

Ile Lys Gln Ile Ile Asn Met Trp Gln Glu Val Gly Arg Ala Met Tyr
305                 310                 315                 320

Ala Pro Pro Ile Arg Gly Gln Ile Arg Cys Ser Ser Asn Ile Thr Gly
                325                 330                 335

Leu Leu Leu Thr Arg Asp Gly Gly Pro Glu Asp Asn Lys Thr Glu Val
            340                 345                 350

Phe Arg Pro Gly Gly Gly Asp Met Arg Asp Asn Trp Arg Ser Glu Leu
        355                 360                 365

Tyr Lys Tyr Lys Val Val Lys Ile Gly Ser Ser Gly Gly Gly Gly Ser
    370                 375                 380

Gly Ser Gly Gly Gly Ser Gly Gly Gly Ala Ala Ala Lys Lys Val
385                 390                 395                 400

Val Leu Gly Lys Lys Gly Asp Thr Val Glu Leu Thr Cys Thr Ala Ser
                405                 410                 415

Gln Lys Lys Ser Ile Gln Phe His Trp Lys Asn Ser Asn Gln Ile Lys
            420                 425                 430

Ile Leu Gly Asn Gln Gly Ser Phe Leu Thr Lys Gly Pro Ser Lys Leu
        435                 440                 445

Asn Asp Arg Ala Asp Ser Arg Arg Ser Leu Trp Asp Gln Gly Asn Phe
    450                 455                 460

Pro Leu Ile Ile Lys Asn Leu Lys Ile Glu Asp Ser Asp Thr Tyr Ile
465                 470                 475                 480

Cys Glu Val Glu Asp Gln Lys Glu Glu Val Gln Leu Leu Val Phe Gly
                485                 490                 495

Leu Thr Ala Asn Ser Asp Thr His Leu Leu Gln Gly Gln Ser Leu Thr
            500                 505                 510

Leu Thr Leu Glu Ser Pro Pro Gly Ser Ser Pro Ser Val Gln Cys Arg
        515                 520                 525

Ser Pro Arg Gly Lys Asn Ile Gln Gly Gly Lys Thr Leu Ser Val Ser
    530                 535                 540

Gln Leu Glu Leu Gln Asp Ser Gly Thr Trp Thr Cys Thr Val Leu Gln
545                 550                 555                 560
```

```
Asn Gln Lys Lys Val Glu Phe Lys Ile Asp Ile Val Val Leu Ala Glu
            565                 570                 575

Gln Lys Leu Ile Ser Glu Glu Asp Leu Xaa Tyr Val Xaa Thr
        580                 585                 590

<210> SEQ ID NO 14
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (14)..(14)
<223> OTHER INFORMATION: Xaa can be any amino acid

<400> SEQUENCE: 14

Glu Gln Lys Leu Ile Ser Glu Glu Asp Leu Xaa Tyr Val Xaa Thr
1               5                   10                  15

<210> SEQ ID NO 15
<211> LENGTH: 111
<212> TYPE: DNA
<213> ORGANISM: Artificial Sequence
<220> FEATURE:
<223> OTHER INFORMATION: Synthetic construct

<400> SEQUENCE: 15
gggggtacca tgcccatggg gtctctgcaa ccgctggcca ccttgtacct gctggggatg      60
ctggtcgctt cctgcctcgg aaagaacgtg accgagaact tcaacatgtg g              111

<210> SEQ ID NO 16
<211> LENGTH: 39
<212> TYPE: DNA
<213> ORGANISM: Artificial Sequence
<220> FEATURE:
<223> OTHER INFORMATION: Synthetic construct

<400> SEQUENCE: 16
gggggatccg atcttcacca ccttgatctt gtacagctc                            39

<210> SEQ ID NO 17
<211> LENGTH: 75
<212> TYPE: DNA
<213> ORGANISM: Artificial Sequence
<220> FEATURE:
<223> OTHER INFORMATION: Synthetic construct

<400> SEQUENCE: 17
ctgtgcgtga ccctgggcgc ggccgagatg aagaactgca gcttcaacat cggcgcgggc      60
cgcctgatca gctgc                                                      75

<210> SEQ ID NO 18
<211> LENGTH: 75
<212> TYPE: DNA
<213> ORGANISM: Artificial Sequence
<220> FEATURE:
<223> OTHER INFORMATION: Synthetic  construct
```

```
<400> SEQUENCE: 18
gcagctgatc aggcggcccg cgccgatgtt gaagctgcag ttcttcatct cgcccgcgcc      60
cagggtcacg cacag                                                      75

<210> SEQ ID NO 19
<211> LENGTH: 87
<212> TYPE: DNA
<213> ORGANISM: Artificial Sequence
<220> FEATURE:
<223> OTHER INFORMATION: Synthetic  construct

<400> SEQUENCE: 19
tgcaacctgg cccgctgcca gctgcgctgc aagagcctgg gcctgctggg caagtgcgcc      60
ggcagcttct gcgcctgcgg cccctaa                                         87

<210> SEQ ID NO 20
<211> LENGTH: 28
<212> TYPE: PRT
<213> ORGANISM: Artificial Sequence
<220> FEATURE:
<223> OTHER INFORMATION: Synthetic construct

<400> SEQUENCE: 20

Cys Asn Leu Ala Arg Cys Gln Leu Arg Cys Lys Ser Leu Gly Leu Leu
1               5                   10                  15

Gly Lys Cys Ala Gly Ser Phe Cys Ala Cys Gly Pro
            20                  25

<210> SEQ ID NO 21
<211> LENGTH: 102
<212> TYPE: DNA
<213> ORGANISM: Artificial Sequence
<220> FEATURE:
<223> OTHER INFORMATION: Synthetic  construct

<400> SEQUENCE: 21
gcggccgctt gcaacctggc ccgctgccag ctgcgctgca agagcctggg cctgctgggc      60
aagtgcgccg gcagcttctg cgcctgcggc ccctaagaat tc                        102

<210> SEQ ID NO 22
<211> LENGTH: 102
<212> TYPE: DNA
<213> ORGANISM: Artificial Sequence
<220> FEATURE:
<223> OTHER INFORMATION: Synthetic  construct

<400> SEQUENCE: 22
gaattcttag gggccgcagg cgcagaagct gccggcgcac ttgcccagca ggcccaggct      60
cttgcagcgc agctggcagc gggccaggtt gcaagcggcc gc                        102

<210> SEQ ID NO 23
<211> LENGTH: 1518
<212> TYPE: DNA
<213> ORGANISM: Artificial Sequence
<220> FEATURE:
<223> OTHER INFORMATION: Synthetic  construct

<400> SEQUENCE: 23
atgcccatgg ggtctctgca accgctggcc accttgtacc tgctggggat gctggtcgct      60
tcctgcctcg gaaacgccga ggagaagctg tgggtgaccg tgtactacgg cgtgcccgtg     120
tggaaggagg ccaccaccac cctgttctgc gccagcgacc gcaaggccta cgacaccgag     180
```

```
gtgcacaacg tgtgggccac ccacgcctgc gtgcccaccg accccaaccc ccaggaggtg      240
gagctgaaga acgtgaccga gaacttcaac atgtggaaga caacatggt ggagcagatg       300 cacgaggaca tcatcagcct gtgggaccag agcctgaagc cctgcgtgaa gctgaccccc      360
ctgtgcgtga ccctgaactg caccgacctg cgcaacgcca ccaacggcaa cgacaccaac      420
accactagta gcagccgcgg catggtgggc ggcggcgaga tgaagaactg cagcttcaac      480
atcaccacca acatccgcgg caaggtgcag aaggagtacc ccctgttcta caagctggac      540
atcgccccca tcgacaacaa cagcaacaac cgctaccgcc tgatcagctg caacaccagc      600
gtgatcaccc aggcctgccc caaggtgagc ttcgagccca tccccatcca ctactgcgcc      660
cccgccggct tcgccatcct gaagtgcaag gacaagaagt tcaacggcaa gggcccctgc      720
accaacgtga gcaccgtgca gtgcacccac ggcatccgcc ccgtggtgag cacccagctg      780
ctgctgaacg gcagcctggc cgaggaggag gtggtgatcc gcagcgccaa cttcgccgac      840
aacgccaagg tgatcatcgt gcagctgaac gagagcgtgg agatcaactg cacccgcccc      900
aacaacaaca cccgcaagtc catccacatc ggccccggcc gcgccttcta caccaccggc      960
gagatcatcg gcgacatccg ccaggcccac tgcaacctga ccgcgccaa gtggaacgac      1020 accctgaaca agatcgtgat caagctgcgc gagcagttcg gcaacaagac catcgtgttc      1080
aagcacagca gcggcggcga ccccgagatc gtgacccaca gcttcaattg cggcggcgag      1140
ttcttctact gcaacagcac ccagctgttc aacagcacct ggaacgtgac cgaggagagc      1200
aacaacaccg tggagaacaa caccatcacc ctgccctgcc gcatcaagca gatcatcaac      1260
atgtggcagg aggtgggccg cgccatgtac gccccccccca tccgcggcca gatccgctgc      1320
agttcaaaca tcaccggcct gctgctgacc cgcgacggcg gccccgagga caacaagacc      1380
gaggtgttcc gccccggcgg cggcgacatg cgcgacaact ggcgcagcga gctgtacaag      1440
tacaaggtgg tgaagatcga gcccctgggc gtggccccca ccaaggccaa gcgccgcgtg      1500
gtgcagcgcg agaagcgt                                                   1518
```

<210> SEQ ID NO 24
<211> LENGTH: 506
<212> TYPE: PRT
<213> ORGANISM: Artificial Sequence
<220> FEATURE:
<223> OTHER INFORMATION: Synthetic construct

<400> SEQUENCE: 24

```
Met Pro Met Gly Ser Leu Gln Pro Leu Ala Thr Leu Tyr Leu Leu Gly
1               5                   10                  15

Met Leu Val Ala Ser Cys Leu Gly Asn Ala Glu Glu Lys Leu Trp Val
            20                  25                  30

Thr Val Tyr Tyr Gly Val Pro Val Trp Lys Glu Ala Thr Thr Thr Leu
        35                  40                  45

Phe Cys Ala Ser Asp Arg Lys Ala Tyr Asp Thr Glu Val His Asn Val
    50                  55                  60

Trp Ala Thr His Ala Cys Val Pro Thr Asp Pro Asn Pro Gln Glu Val
65                  70                  75                  80

Glu Leu Lys Asn Val Thr Glu Asn Phe Asn Met Trp Lys Asn Asn Met
                85                  90                  95

Val Glu Gln Met His Glu Asp Ile Ile Ser Leu Trp Asp Gln Ser Leu
            100                 105                 110

Lys Pro Cys Val Lys Leu Thr Pro Leu Cys Val Thr Leu Asn Cys Thr
        115                 120                 125
```

Asp Leu Arg Asn Ala Thr Asn Gly Asn Asp Thr Asn Thr Thr Ser Ser
130                 135                 140

Ser Arg Gly Met Val Gly Gly Glu Met Lys Asn Cys Ser Phe Asn
145                 150                 155                 160

Ile Thr Thr Asn Ile Arg Gly Lys Val Gln Lys Glu Tyr Ala Leu Phe
            165                 170                 175

Tyr Lys Leu Asp Ile Ala Pro Ile Asp Asn Asn Ser Asn Asn Arg Tyr
            180                 185                 190

Arg Leu Ile Ser Cys Asn Thr Ser Val Ile Thr Gln Ala Cys Pro Lys
            195                 200                 205

Val Ser Phe Glu Pro Ile Pro Ile His Tyr Cys Ala Pro Ala Gly Phe
210                 215                 220

Ala Ile Leu Lys Cys Lys Asp Lys Lys Phe Asn Gly Lys Gly Pro Cys
225                 230                 235                 240

Thr Asn Val Ser Thr Val Gln Cys Thr His Gly Ile Arg Pro Val Val
            245                 250                 255

Ser Thr Gln Leu Leu Leu Asn Gly Ser Leu Ala Glu Glu Val Val
            260                 265                 270

Ile Arg Ser Ala Asn Phe Ala Asp Asn Ala Lys Val Ile Ile Val Gln
            275                 280                 285

Leu Asn Glu Ser Val Glu Ile Asn Cys Thr Arg Pro Asn Asn Asn Thr
290                 295                 300

Arg Lys Ser Ile His Ile Gly Pro Gly Arg Ala Phe Tyr Thr Thr Gly
305                 310                 315                 320

Glu Ile Ile Gly Asp Ile Arg Gln Ala His Cys Asn Leu Ser Arg Ala
            325                 330                 335

Lys Trp Asn Asp Thr Leu Asn Lys Ile Val Ile Lys Leu Arg Glu Gln
            340                 345                 350

Phe Gly Asn Lys Thr Ile Val Phe Lys His Ser Ser Gly Gly Asp Pro
            355                 360                 365

Glu Ile Val Thr His Ser Phe Asn Cys Gly Gly Glu Phe Phe Tyr Cys
370                 375                 380

Asn Ser Thr Gln Leu Phe Asn Ser Thr Trp Asn Val Thr Glu Glu Ser
385                 390                 395                 400

Asn Asn Thr Val Glu Asn Asn Thr Ile Thr Leu Pro Cys Arg Ile Lys
            405                 410                 415

Gln Ile Ile Asn Met Trp Gln Glu Val Gly Arg Ala Met Tyr Ala Pro
            420                 425                 430

Pro Ile Arg Gly Gln Ile Arg Cys Ser Ser Asn Ile Thr Gly Leu Leu
            435                 440                 445

Leu Thr Arg Asp Gly Gly Pro Glu Asp Asn Lys Thr Glu Val Phe Arg
450                 455                 460

Pro Gly Gly Gly Asp Met Arg Asp Asn Trp Arg Ser Glu Leu Tyr Lys
465                 470                 475                 480

Tyr Lys Val Val Lys Ile Glu Pro Leu Gly Val Ala Pro Thr Lys Ala
            485                 490                 495

Lys Arg Arg Val Val Gln Arg Glu Lys Arg
            500                 505

<210> SEQ ID NO 25
<211> LENGTH: 534
<212> TYPE: DNA
<213> ORGANISM: Artificial Sequence
<220> FEATURE:
<223> OTHER INFORMATION: Synthetic construct

<400> SEQUENCE: 25

```
aagaaagtgg tgctgggcaa aaaggggat acagtggaac tgacctgtac agcttcccag      60
aagaagagca tacaattcca ctggaaaaac tccaaccaga taaagattct gggaaatcag     120
ggctccttct taactaaagg tccatccaag ctgaatgatc gcgctgactc aagaagaagc     180
ctttgggacc aaggaaactt ccccctgatc atcaagaatc ttaagataga agactcagat     240
acttacatct gtgaagtgga ggaccagaag gaggaggtgc aattgctagt gttcggattg     300
actgccaact ctgacaccca cctgcttcag ggcagagcc tgaccctgac cttggagagc      360 cccctggta gtagcccctc agtgcaatgt aggagtccaa ggggtaaaaa catacagggg      420
gggaagaccc tctccgtgtc tcagctggag ctccaggata gtggcacctg gacatgcact     480
gtcttgcaga accagaagaa ggtggagttc aaaatagaca tcgtggtgct agct          534
```

<210> SEQ ID NO 26
<211> LENGTH: 178
<212> TYPE: PRT
<213> ORGANISM: Artificial Sequence
<220> FEATURE:
<223> OTHER INFORMATION: Synthetic construct

<400> SEQUENCE: 26

```
Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala
```

<210> SEQ ID NO 27
<211> LENGTH: 1128
<212> TYPE: DNA
<213> ORGANISM: Artificial Sequence
<220> FEATURE:
<223> OTHER INFORMATION: Synthetic construct

<400> SEQUENCE: 27

```
atgcccatgg ggtctctgca accgctggcc accttgtacc tgctggggat gctggtcgct      60
tcctgcctcg gaaagaacgt gaccgagaac ttcaacatgt ggaagaacaa catggtggag     120
```

```
cagatgcacg aggacatcat cagcctgtgg gaccagagcc tgaagccctg cgtgaagctg    180
acccccctgt gcgtgaccct gggcgcgggc gagatgaaga actgcagctt caacatcggc    240
gcgggccgcc tgatcagctg caacaccagc gtgatcaccc aggcctgccc caaggtgagc    300
ttcgagccca tccccatcca ctactgcgcc ccgccggct cgccatcct gaagtgcaag     360 gacaagaagt tcaacggcaa gggcccctgc accaacgtga gcaccgtgca gtgcacccac    420
ggcatccgcc ccgtggtgag cacccagctg ctgctgaacg gcagcctggc cgaggaggag    480
gtggtgatcc gcagcgccaa cttcgccgac aacgccaagg tgatcatcgt gcagctgaac    540
gagagcgtgg agatcaactg cacccgcccc aacaacaaca cccgcaagtc catccacatc    600
ggccccggcc gcgccttcta caccaccggc gagatcatcg cgacatccg ccaggcccac     660 tgcaacctga ccgcgccaa gtggaacgac accctgaaca agatcgtgat caagctgcgc    720
gagcagttcg gcaacaagac catcgtgttc aagcacagca gcggcggcga ccccgagatc    780
gtgacccaca gcttcaattg cggcggcgag ttcttctact gcaacagcac ccagctgttc    840
aacagcacct ggaacgtgac cgaggagagc aacaacaccg tggagaacaa caccatcacc    900
ctgccctgcc gcatcaagca gatcatcaac atgtggcagg aggtgggccg cgccatgtac    960
gcccccccca tccgcggcca gatccgctgc agttchaaca tcaccggcct gctgctgacc    1020
cgcgacggcg gccccgagga caacaagacc gaggtgttcc gccccggcgg cggcgacatg    1080
cgcgacaact ggcgcagcga gctgtacaag tacaaggtgg tgaagatc    1128
```

<210> SEQ ID NO 28
<211> LENGTH: 376
<212> TYPE: PRT
<213> ORGANISM: Artificial Sequence
<220> FEATURE:
<223> OTHER INFORMATION: Synthetic construct

<400> SEQUENCE: 28

```
Met Pro Met Gly Ser Leu Gln Pro Leu Ala Thr Leu Tyr Leu Leu Gly
1               5                   10                  15

Met Leu Val Ala Ser Cys Leu Gly Lys Asn Val Thr Glu Asn Phe Asn
            20                  25                  30

Met Trp Lys Asn Asn Met Val Glu Gln Met His Glu Asp Ile Ile Ser
        35                  40                  45

Leu Trp Asp Gln Ser Leu Lys Pro Cys Val Lys Leu Thr Pro Leu Cys
    50                  55                  60

Val Thr Leu Gly Ala Gly Glu Met Lys Asn Cys Ser Phe Asn Ile Gly
65                  70                  75                  80

Ala Gly Arg Leu Ile Ser Cys Asn Thr Ser Val Ile Thr Gln Ala Cys
                85                  90                  95

Pro Lys Val Ser Phe Glu Pro Ile Pro Ile His Tyr Cys Ala Pro Ala
            100                 105                 110

Gly Phe Ala Ile Leu Lys Cys Lys Asp Lys Lys Phe Asn Gly Lys Gly
        115                 120                 125

Pro Cys Thr Asn Val Ser Thr Val Gln Cys Thr His Gly Ile Arg Pro
    130                 135                 140

Val Val Ser Thr Gln Leu Leu Leu Asn Gly Ser Leu Ala Glu Glu Glu
145                 150                 155                 160

Val Val Ile Arg Ser Ala Asn Phe Ala Asp Asn Ala Lys Val Ile Ile
                165                 170                 175

Val Gln Leu Asn Glu Ser Val Glu Ile Asn Cys Thr Arg Pro Asn Asn
            180                 185                 190
```

```
Asn Thr Arg Lys Ser Ile His Ile Gly Pro Gly Arg Ala Phe Tyr Thr
            195                 200                 205

Thr Gly Glu Ile Ile Gly Asp Ile Arg Gln Ala His Cys Asn Leu Ser
210                 215                 220

Arg Ala Lys Trp Asn Asp Thr Leu Asn Lys Ile Val Ile Lys Leu Arg
225                 230                 235                 240

Glu Gln Phe Gly Asn Lys Thr Ile Val Phe Lys His Ser Ser Gly Gly
            245                 250                 255

Asp Pro Glu Ile Val Thr His Ser Phe Asn Cys Gly Gly Glu Phe Phe
            260                 265                 270

Tyr Cys Asn Ser Thr Gln Leu Phe Asn Ser Thr Trp Asn Val Thr Glu
            275                 280                 285

Glu Ser Asn Asn Thr Val Glu Asn Asn Thr Ile Thr Leu Pro Cys Arg
            290                 295                 300

Ile Lys Gln Ile Ile Asn Met Trp Gln Glu Val Gly Arg Ala Met Tyr
305                 310                 315                 320

Ala Pro Pro Ile Arg Gly Gln Ile Arg Cys Ser Ser Asn Ile Thr Gly
            325                 330                 335

Leu Leu Leu Thr Arg Asp Gly Gly Pro Glu Asp Asn Lys Thr Glu Val
            340                 345                 350

Phe Arg Pro Gly Gly Gly Asp Met Arg Asp Asn Trp Arg Ser Glu Leu
            355                 360                 365

Tyr Lys Tyr Lys Val Val Lys Ile
            370                 375

<210> SEQ ID NO 29
<211> LENGTH: 1518
<212> TYPE: DNA
<213> ORGANISM: Artificial Sequence
<220> FEATURE:
<223> OTHER INFORMATION: Synthetic construct

<400> SEQUENCE: 29
atgcccatgg ggtctctgca accgctggcc accttgtacc tgctggggat gctggtcgct     60
tcctgcctcg gaaacgccga ggagaagctg tgggtgaccg tgtactacgg cgtgcccgtg    120
tggaaggagg ccaccaccac cctgttctgc gccagcgacc gcaaggccta cgacaccgag    180
gtgcacaacg tgtgggccac ccacgcctgc gtgcccaccg accccaaccc ccaggaggtg    240 agctgaaga cgtgaccga gaacttcaac atgtggaaga caacatggt ggagcagatg    300 cacgaggaca tcatcagcct gtgggaccag agcctgaagc cctgcgtgaa gctgaccccc    360
ctgtgcgtga ccctgaactg caccgacctg cgcaacgcca ccaacggcaa cgacaccaac    420
accactagta gcagccgcgg catggtgggc ggcggcgaga tgaagaactg cagcttcaac    480
atcaccacca acatccgcgg caaggtgcag aaggagtacg ccctgttcta caagctggac    540
atcgccccca tcgacaacaa cagcaacaac cgctaccgcc tgatcagctg caacaccagc    600
gtgatcaccc aggcctgccc caaggtgagc ttcgagccca tcccatcca ctactgcgcc    660 cccgccggct cgccatcct gaagtgcaag gacaagaagt tcaacggcaa gggcccctgc    720
accaacgtga gcaccgtgca gtgcacccac ggcatccgcc cgtggtgag cacccagctg    780 ctgctgaacg gcagcctggc cgaggaggag gtggtgatcc gcagcgccaa cttcgccgac    840
aacgccaagg tgatcatcgt gcagctgaac gagagcgtgg agatcaactg cacccgcccc    900
aacaacaaca cccgcaagtc catccacatc ggccccggcc gcgccttcta caccaccggc    960
gagatcatcg gcgacatccg ccaggcccac tgcaacctga gccgcgccaa gtggaacgac   1020
```

```
acctgaaca agatcgtgat caagctgcgc gagcagttcg gcaacaagac catcgtgttc    1080
aagcacagca gcggcggcga ccccgagatc gtgacccaca gcttcaattg cggcggcgag    1140
ttcttctact gcaacagcac ccagctgttc aacagcacct ggaacgtgac cgaggagagc    1200
aacaacaccg tggagaacaa caccatcacc ctgccctgcc gcatcaagca gatcatcaac    1260
atgtggcagg aggtgggccg cgccatgtac gccccccca tccgcggcca gatccgctgc    1320
agttchaaca tcaccggcct gctgctgacc cgcgacggcg ccccgagga caacaagacc    1380 gaggtgttcc gccccggcgg cggcgacatg cgcgacaact ggcgcagcga gctgtacaag    1440
tacaaggtgg tgaagatcga gcccctgggc gtggccccca ccaaggccaa gcgccgcgtg    1500
gtgcagcgcg agaagacc                                                 1518
```

<210> SEQ ID NO 30
<211> LENGTH: 506
<212> TYPE: PRT
<213> ORGANISM: Artificial Sequence
<220> FEATURE:
<223> OTHER INFORMATION: Synthetic construct

<400> SEQUENCE: 30

```
Met Pro Met Gly Ser Leu Gln Pro Leu Ala Thr Leu Tyr Leu Leu Gly
1               5                   10                  15

Met Leu Val Ala Ser Cys Leu Gly Asn Ala Glu Glu Lys Leu Trp Val
            20                  25                  30

Thr Val Tyr Tyr Gly Val Pro Val Trp Lys Glu Ala Thr Thr Thr Leu
        35                  40                  45

Phe Cys Ala Ser Asp Arg Lys Ala Tyr Asp Thr Glu Val His Asn Val
    50                  55                  60

Trp Ala Thr His Ala Cys Val Pro Thr Asp Pro Asn Pro Gln Glu Val
65                  70                  75                  80

Glu Leu Lys Asn Val Thr Glu Asn Phe Asn Met Trp Lys Asn Asn Met
                85                  90                  95

Val Glu Gln Met His Glu Asp Ile Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asp Leu Arg Asn Ala Thr Asn Gly Asn Asp Thr Asn Thr Thr Ser Ser
    130                 135                 140

Ser Arg Gly Met Val Gly Gly Glu Met Lys Asn Cys Ser Phe Asn
145                 150                 155                 160

Ile Thr Thr Asn Ile Arg Gly Lys Val Gln Lys Glu Tyr Ala Leu Phe
                165                 170                 175

Tyr Lys Leu Asp Ile Ala Pro Ile Asp Asn Asn Ser Asn Asn Arg Tyr
            180                 185                 190

Arg Leu Ile Ser Cys Asn Thr Ser Val Ile Thr Gln Ala Cys Pro Lys
        195                 200                 205

Val Ser Phe Glu Pro Ile Pro Ile His Tyr Cys Ala Pro Ala Gly Phe
    210                 215                 220

Ala Ile Leu Lys Cys Lys Asp Lys Lys Phe Asn Gly Lys Gly Pro Cys
225                 230                 235                 240

Thr Asn Val Ser Thr Val Gln Cys Thr His Gly Ile Arg Pro Val Val
                245                 250                 255

Ser Thr Gln Leu Leu Leu Asn Gly Ser Leu Ala Glu Glu Val Val
            260                 265                 270
```

Ile Arg Ser Ala Asn Phe Ala Asp Asn Ala Lys Val Ile Ile Val Gln
        275                 280                 285

Leu Asn Glu Ser Val Glu Ile Asn Cys Thr Arg Pro Asn Asn Asn Thr
        290                 295                 300

Arg Lys Ser Ile His Ile Gly Pro Gly Arg Ala Phe Tyr Thr Thr Gly
305                 310                 315                 320

Glu Ile Ile Gly Asp Ile Arg Gln Ala His Cys Asn Leu Ser Arg Ala
                325                 330                 335

Lys Trp Asn Asp Thr Leu Asn Lys Ile Val Ile Lys Leu Arg Glu Gln
                340                 345                 350

Phe Gly Asn Lys Thr Ile Val Phe Lys His Ser Ser Gly Gly Asp Pro
            355                 360                 365

Glu Ile Val Thr His Ser Phe Asn Cys Gly Gly Glu Phe Phe Tyr Cys
        370                 375                 380

Asn Ser Thr Gln Leu Phe Asn Ser Thr Trp Asn Val Thr Glu Glu Ser
385                 390                 395                 400

Asn Asn Thr Val Glu Asn Asn Thr Ile Thr Leu Pro Cys Arg Ile Lys
                405                 410                 415

Gln Ile Ile Asn Met Trp Gln Glu Val Gly Arg Ala Met Tyr Ala Pro
                420                 425                 430

Pro Ile Arg Gly Gln Ile Arg Cys Ser Ser Asn Ile Thr Gly Leu Leu
            435                 440                 445

Leu Thr Arg Asp Gly Gly Pro Glu Asp Asn Lys Thr Glu Val Phe Arg
        450                 455                 460

Pro Gly Gly Gly Asp Met Arg Asp Asn Trp Arg Ser Glu Leu Tyr Lys
465                 470                 475                 480

Tyr Lys Val Val Lys Ile Glu Pro Leu Gly Val Ala Pro Thr Lys Ala
                485                 490                 495

Lys Arg Arg Val Val Gln Arg Glu Lys Thr
            500                 505

<210> SEQ ID NO 31
<211> LENGTH: 776
<212> TYPE: DNA
<213> ORGANISM: Artificial Sequence
<220> FEATURE:
<223> OTHER INFORMATION: Synthetic construct

<400> SEQUENCE: 31
atgcccatgg ggtctctgca accgctggcc accttgtacc tgctggggat gctggtcgct    60
tccgtgctag cggatcccga ggagcccaaa tcttgtgaca aaactcacac atgcccaccg   120
tgcccagcac ctgaactcct ggggggaccg tcagtcttcc tcttcccccc aaaacccaag   180
gacaccctca tgatctcccg gacccctgag gtcacatgcg tggtggtgga cgtgagccac   240
gaagaccctg aggtcaagtt caactggtac gtggacggcg tggaggtgca taatgccaag   300
acaaagccgc gggaggagca gtacaacagc acgtaccggg tggtcagcgt cctcaccgtc   360
ctgcaccagg actggctgaa tgcaaggag tacaagtgca aggtctccaa caaagccctc   420
ccagccccca tcgagaaaac catctccaaa gccaagggc agccccgaga accacaggtg   480
tacaccctgc ccccatcccg ggatgagctg accaagaacc aggtcagcct gacctgcctg   540
gtcaaaggct tctatcccag cgacatcgcc gtggagtggg agagcaatgg gcagccggag   600
aacaactaca agaccacgcc tcccgtgctg gactccgacg gctccttctt cctctacagc   660

```
aagctcaccg tggacaagag caggtggcag caggggaacg tcttctcatg ctccgtgatg    720
catgaggctc tgcacaacca ctacacgcag aagagcctct ccctgtctcc gggtaa        776
```

<210> SEQ ID NO 32
<211> LENGTH: 259
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (259)..(259)
<223> OTHER INFORMATION: Xaa can be any amino acid

<400> SEQUENCE: 32

```
Met Pro Met Gly Ser Leu Gln Pro Leu Ala Thr Leu Tyr Leu Leu Gly
1               5                   10                  15

Met Leu Val Ala Ser Val Leu Ala Asp Pro Glu Glu Pro Lys Ser Cys
            20                  25                  30

Asp Lys Thr His Thr Cys Pro Pro Cys Pro Ala Pro Glu Leu Leu Gly
        35                  40                  45

Gly Pro Ser Val Phe Leu Phe Pro Pro Lys Pro Lys Asp Thr Leu Met
    50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
        115                 120                 125

Lys Glu Tyr Lys Cys Lys Val Ser Asn Lys Ala Leu Pro Ala Pro Ile
    130                 135                 140

Glu Lys Thr Ile Ser Lys Ala Lys Gly Gln Pro Arg Glu Pro Gln Val
145                 150                 155                 160

Tyr Thr Leu Pro Pro Ser Arg Asp Glu Leu Thr Lys Asn Gln Val Ser
                165                 170                 175

Leu Thr Cys Leu Val Lys Gly Phe Tyr Pro Ser Asp Ile Ala Val Glu
            180                 185                 190

Trp Glu Ser Asn Gly Gln Pro Glu Asn Asn Tyr Lys Thr Thr Pro Pro
        195                 200                 205

Val Leu Asp Ser Asp Gly Ser Phe Phe Leu Tyr Ser Lys Leu Thr Val
    210                 215                 220

Asp Lys Ser Arg Trp Gln Gln Gly Asn Val Phe Ser Cys Ser Val Met
225                 230                 235                 240

His Glu Ala Leu His Asn His Tyr Thr Gln Lys Ser Leu Ser Leu Ser
                245                 250                 255

Pro Gly Xaa
```

<210> SEQ ID NO 33
<211> LENGTH: 63
<212> TYPE: DNA
<213> ORGANISM: Artificial Sequence
<220> FEATURE:
<223> OTHER INFORMATION: Synthetic construct -continued

```
<400> SEQUENCE: 33
ggatcctctg gtggcggtgg ctcgggctcc ggaggaggtg ggtcgggtgg cggcgcggcc      60
gct                                                                    63
```

VIRUS COAT PROTEIN/RECEPTOR CHIMERAS AND METHOD OF USE

CROSS REFERENCE TO RELATED APPLICATION

This application is a divisonal of U.S. patent application Ser. No. 09/934,060 filed on Aug. 21, 2001, now U.S. Pat. No. 6,908,612 which claims priority from co-pending application U.S. Ser. No. 09/684,026 filed on Oct. 6, 2000 that claims priority from U.S. Provisional application No. 60/158,321 filed on Oct. 8, 1999.

STATEMENT AS TO FEDERALLY SPONSORED RESEARCH

This invention was made with Government support under R0 1 HL59796 awarded by National Institutes of Health. The Government may have certain rights in the invention.

BACKGROUND THE INVENTION

1. Field of the Invention

This invention relates generally to receptor ligand interactions, and more specifically to chimeric polypeptides having virus coat polypeptide and cell receptor polypeptide sequences that bind to each other and mimic the structural, functional and immunogenic properties that naturally occur when the virus protein and receptor interact in vivo.

2. Description of Related Art

Humoral immunity arising after primary infection with HIV-1 may not prevent progression to AIDS (R. A. Koup et al., *Nature*, 370:416 (1994); R. A. Koup et al., *J. Virol.* 68:4650-5 (1994)). However, it is likely that Humoral immunity can prevent infection if an individual has high-titered neutralizing antibodies prior to exposure to the virus. This concept is largely supported by passive immunization studies in which chimps were transfused with neutralizing anti-V3 monoclonal antibodies or pooled, high-titered neutralizing antisera around the time of challenge with cell-free virus (E. A. Emini et al., *Nature*: 355:728-30 (1992); R. Shibata et al., *Nat. Med.*, 5:204-10 (1999)). Protection was obtained in both sets of studies, indicating that humoral immunity can be protective provided the right antibodies are present in sufficient titers at the time of challenge or shortly thereafter.

Additional studies suggest that humoral immunity can be protective against HIV-1. For example, passive immunization using the SCID-hu mouse system have shown that human monoclonal antibodies specific for the CD4 binding domain of gp120 can prevent infection (M. C. Gauduin et al., *Nat. Med.*, 3: 1389-93 (1997); P. W. Parren et al., *AIDS*, 9:F1-6 (1995)). It has been further shown that passive transfer of a bivalent CD4-Ig "immunoadhesin," a chimera made between CD4 and the human IgG2 heavy chain, can protect in the HIV-1 chimp challenge system (J. W. Eichberg et al., *AIDS Res. Hum. Retroviruses*, 8: 1515-19 (1992); R. H. Ward et al., *Nature*, 352:434-6 (1991)). Additionally, neutralizing antibodies correlate strongly with protective immunity against SIV (J. L. Heeney et al., *Proc. Natl. Acad. Sci. U.S.A.*, 95: 10803-8 (1998)). Still further, passive transfer studies in rhesus macaques showed that high-titered chimp antibodies specific for the HIV-1 $_{DH12}$ isolate, provided sterilizing immunity in rhesus macaques against SHIV$_{DH12}$ if a sufficient concentration of the antibodies was used (R. Shibata et al., *Nat. Med.*, 5:204-10 (1999)). Also, passive-transfer experiments in rhesus macaques using HIVIg, 2G12, and 2F5 demonstrated 50% better protection in recipient groups compared to non-recipient controls against challenge with SHIV-89.6P (Mascola et al., *J. Virol.*, 73:4009-18 (1999)). Thus, these studies support the idea that immunization strategies which elicit persistent, high-titered (or highly effective) neutralizing antibody responses of broad specificity may be protective. A successful strategy to reach this goal has been elusive. The subunit formulations of recombinant monomeric or oligomeric HIV envelope that have been tested elicit neutralizing responses against a narrow range of isolates (J. P. Moore et al., *AIDS*, 9:S117-136 (1995); Q. J. Sattentau, *Curr. Opin. Immunol.*, 8:540-5 (1996); R. Wyatt et al., *Science*, 280:1884-8 (1998)).

SUMMARY OF THE INVENTION

The present invention relates to chimeric polypeptides containing a virus coat polypeptide sequence and a viral receptor polypeptide sequence in which the coat polypeptide sequence and the receptor polypeptide sequence are linked by a spacer. The coat polypeptide and the viral receptor polypeptide sequences of the chimeric polypeptides can bind to each other. The chimeric polypeptides of the invention are useful for inducing an immune response and for producing antibodies. Further, the chimeric polypeptides are useful for preventing, inhibiting, or ameliorating a viral infection by passive protection against virus infection or by production of an immune response (i.e., antibodies or a CTL response) by administration to a subject.

In various embodiments, the virus coat polypeptide sequence of a chimeric polypeptide is an envelope polypeptide sequence (e.g., full-length gp120 or a fragment), a virus that binds a co-receptor polypeptide, an immunodeficiency virus, including HIV (e.g., HIV-1 or HIV-2), SIV, FIV, FeLV, FPV, and a herpes virus. In various additional embodiments, the viral receptor polypeptide sequence is a CD4 polypeptide sequence, full-length or a fragment thereof, such as the D1, D2 domains and mutations thereof. Introducing envelope genes derived from viruses that use alternative co-receptors could further expand the potential of these single chain molecules affording protection from viral infection of different cell types that express the different co-receptors.

Chimeric polypeptides having heterologous domains also are provided. Such heterologous domains impart a distinct functionality and include tags, adhesins and immunopotentiating agents. For example, heterologous domains can have an amino acid sequence, such as a c-myc polypeptide sequence or an immunoglobulin polypeptide sequence (e.g., a heavy chain polypeptide sequence).

In accordance with the present invention, there are provided polynucleotide sequences having a nucleic acid sequence encoding chimeric polypeptides. The polynucleotides can be included in an expression vector and are useful for expressing chimeric polypeptides.

In accordance with the present invention, there are provided antibodies and functional fragments thereof that bind to the chimeric polypeptides of the present invention. The antibodies are useful in treatment methods and in diagnostic methods. Such antibodies can neutralize the immunodeficiency virus in vitro or in vivo, and can also be useful in inhibiting immunodeficiency virus infection, for example, by passive protection. Such antibodies can bind to an epitope produced by the binding of the virus coat polypeptide sequence and viral receptor polypeptide sequence. For example, such an epitope can be present on an envelope polypeptide sequence.

The chimeric polypeptides, polynucleotides and antibodies of the present invention are useful for treating viral infection, or for inducing an immune response. Thus, in accordance with the present invention, there are provided chimeric polypeptides, polynucleotides and antibodies in a pharmaceutically acceptable carrier.

Methods for producing an antibody include administering a chimeric polypeptide of the present invention in an amount sufficient for the subject to produce antibodies to the chimeric polypeptide. Such methods also can be useful, for example, for inhibiting or ameliorating virus infection in a subject, or for passive protection, when the antibody is administered to a recipient subject.

Methods for inhibiting virus infection in a subject include administering an effective amount of a chimeric polypeptide of the invention, or a polynucleotide encoding same to inhibit virus infection of a cell. The administered chimeric polypeptide can prevent virus infection by binding to a viral co-receptor on the cells of the subject or produce a protective immune response. The chimeric polypeptide can be administered in an amount sufficient to ameliorate the virus infection in the subject.

A method that produces an immune response can produce an antibody response or a CTL response. The antibodies produced can neutralize the immunodeficiency virus in vitro. The antibodies also may bind to an epitope exposed by the binding of the two polypeptide sequences of the chimeric polypeptide.

Methods for identifying agents that modulate binding or interaction between a virus and a virus co-receptor, and a virus and a virus receptor, also are provided. In one embodiment, a method includes contacting a chimeric polypeptide having a coat protein of a virus that binds to a receptor with a co-receptor polypeptide (e.g., a CCR5 or CXCR4 polypeptide sequence) under conditions allowing the chimeric polypeptide and the co-receptor polypeptide to bind, in the presence and absence of a test agent, and detecting binding in the presence and absence of the test agent. Decreased binding in the presence of the test agent identifies an agent that inhibits binding between the virus and the virus co-receptor polypeptide.

In another embodiment, a method includes contacting a chimeric polypeptide under conditions allowing intramolecular binding within the chimeric polypeptide, in the presence and absence of a test agent, and detecting intramolecular binding or interaction within the chimeric polypeptide. Decreased binding in the presence of the test agent identifies an agent that inhibits intramolecular binding or interaction between the virus and the virus receptor polypeptide in the chimera. The agent can be added before or after contacting the chimeric polypeptide with the virus co-receptor polypeptide. The virus co-receptor or receptor polypeptide can be present on the surface of an intact cell, which can be present in an animal, such as a non-human primate. The methods can be performed using an immunodeficiency virus, such as HIV, SIV, and the like. Test agents include a library of agents, such as peptides, organic molecules, antibodies and fragments thereof, antivirals, virus co-receptors, functional fragments, and peptide mimetics thereof.

Methods for identifying a chimeric polypeptide sequence that modulate (inhibits or stimulates) virus infection of a cell also are provided. In one embodiment, a method includes contacting a cell susceptible to virus infection with an infectious virus particle in the presence and absence of the chimeric polypeptide sequence of the present invention and determining whether the chimeric polypeptide modulates (inhibits or stimulates) virus infection of the cell (in vitro or in vivo).

DETAILED DESCRIPTION OF THE INVENTION

Figure 1:
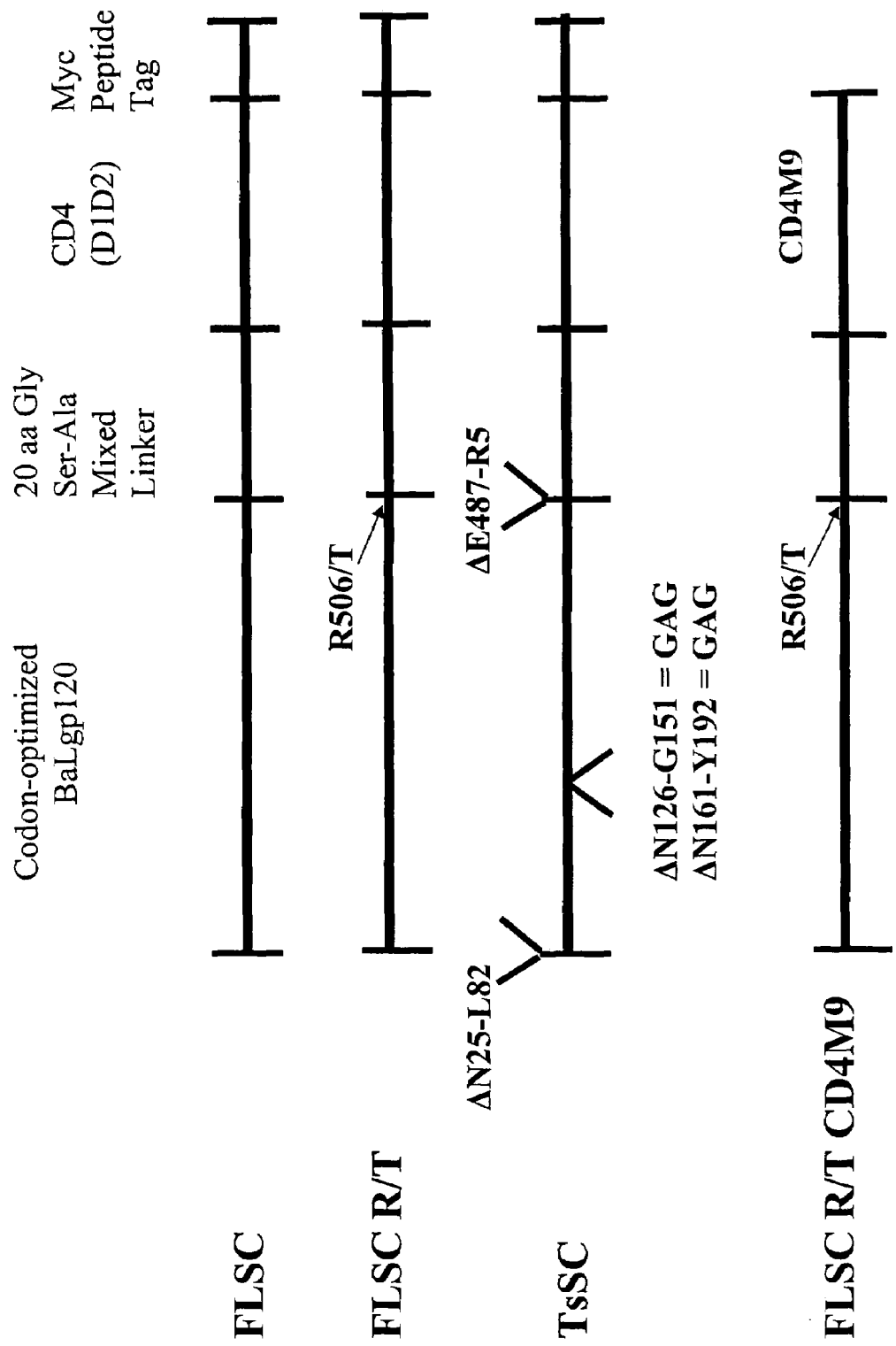
FIG. 1 is a diagram of a polynucleotide construct that encodes exemplary chimeric polypeptides. Full-length single chain (FLSC) chimeric polypeptide comprises an HIV gp120 (BaL strain), a 20 amino acid spacer polypeptide, a CD4 polypeptide sequence comprising the D1 and D2 domains (D1 D2), and a myc peptide "tag." A truncated single chain (TsSC) chimera contains deletions in the C1 (constant region 1), V1 (variable region 1), V2, and C5. The deletions indicated for TcSC are numbered according to the BaL gp120 sequence. A FLSC R/T chimera has a single mutation in the furin cleavage site, an R is changed to a T, at the c-terminus of gp120. A FLSC R/T CD4M9 chimera has a single mutation in the furin cleavage site of gp120, a 21 amino acid spacer polypeptide and a CD4M9 peptide sequence.

The present invention is based on the discovery that a chimeric polypeptide comprising an HIV envelope polypeptide and a CD4 receptor can form an interacting complex capable of binding to a co-receptor. In the chimeric polypeptides of the present invention, HIV gp120 binding to CD4 mimics the envelope protein-CD4 transition state that occurs when HIV binds CD4 present on cells; gp120 displays conserved epitopes exposed upon complex formation that interact directly with co-receptor, CCR5. Formation of the envelope-CD4 transition state and subsequent binding to cell co-receptor is a critical step in HIV infection of cells. Therefore, antibodies or other agents that prevent or inhibit gp120-CD4 binding to co-receptor, for example, by binding epitopes exposed upon gp120-CD4 complex formation could inhibit virus interaction with the co-receptor thereby mediating protection from HIV infection.

Accordingly, chimeric polypeptides or a nucleic acids encoding the chimeric polypeptides of the present invention can be used therapeutically for treating, inhibiting, preventing or ameliorating virus infection, for example, by inducing an immune response to the transition state complex formed upon binding of a virus coat protein to a receptor polypeptide. Such chimeric polypeptides, also referred to herein as "single chain" molecules, can be used to screen for agents that inhibit, prevent or disrupt the binding of the coat polypeptide sequence to the polypeptide receptor sequence within the chimeric sequence, or binding of the chimera to a co-receptor polypeptide sequence, thereby identifying potential therapeutics for treating the corresponding viral infection. For example, an agent that inhibits, prevents or disrupts immunodeficiency virus envelope polypeptide CD4 complex binding to CCR5 can be a therapeutic agent for treating a subject having or at risk of having HIV.

Chimeric polypeptides are also useful for producing antibodies specific for the interacting coat protein-receptor complex. Such specific antibodies can be used for passive protection against virus infection or proliferation, for diagnostic purposes and for identifying and characterizing epitopes exposed upon complex formation (e.g., a cryptic epitope). Even in the absence of intramolecular binding between virus coat protein and a receptor, a chimeric polypeptide may be more effective at eliciting an immune response than a virus coat polypeptide sequence alone. Accordingly, such non-interacting chimeric polypeptides also are valuable and are included herein.

Chimeric polypeptides containing a virus coat polypeptide that binds a receptor and co-receptor have the additional advantage of passively protecting against virus infection by inhibiting virus access to cell co-receptors in vivo. Moreover, such chimeric polypeptides can be used to screen for therapeutics by identifying agents that inhibit, prevent or disrupt the binding of the chimeric polypeptide to co-receptor. For example, an agent that inhibits, prevents or disrupts binding of the immunodeficiency virus envelope polyeptide-CD4 complex to CCR5 can be a therapeutic agent for treating a subject having or at risk of having HIV. As virus binding to cell receptors is required for virus infection of any cell, chimeric polypeptides comprising a polypeptide sequence of any virus coat protein and a corresponding receptor are included in the invention compositions and methods.

In accordance with the present invention, there are provided chimeric polypeptides comprising a virus coat polypeptide sequence and a viral receptor polypeptide sequence linked by a spacer. The coat polypeptide sequence and receptor polypeptide sequence of the chimeric polypeptide are linked by a spacer having a sufficient length of amino acids such that the two polypeptide sequences of the chimeric polypeptide preferably bind or interact. In one embodiment, the coat polypeptide sequence is an envelope polypeptide sequence of an immunodeficiency virus. In another embodiment, the coat polypeptide sequence is from a virus that binds a co-receptor polypeptide. In various other embodiments, the coat polypeptide sequence and the receptor polypeptide sequence are active fragments of a corresponding full-length native sequence.

As used herein, the term "coat" means a polypeptide sequence of virus origin that can bind to cells. Generally, virus coat proteins are present near the exterior surface of the virus particle and allow binding and subsequent penetration into the cell membrane. However, a coat polypeptide sequence includes any virus protein capable of binding to or interacting with a receptor polypeptide. Coat polypeptide sequences as defined herein may be non-covalently or covalently associated with other molecular entities, such as carbohydrates, fatty acids, lipids and the like. Coat polypeptide sequences may contain multiple virus polypeptide sequences. For example, a gag polypeptide sequence may also be included with an envelope polypeptide sequence in a chimeric polypeptide to maintain the envelope polypeptide sequence in a conformation that binds to a receptor polypeptide sequence.

Virus coat polypeptide sequences useful in the present invention can be of any origin including, for example, bacterial, plant, and animal viruses, so long as a corresponding cell receptor is known or can be identified. Examples of particular virus included are: Retroviridae (e.g human immunodeficiency viruses, such as HIV); Picornaviridae (e.g., polio viruses, hepatitis A virus; enteroviruses, human coxsackie viruses, rhinoviruses, echoviruses); Calciviridae (e.g., strains that cause gastroenteritis); Togaviradae (e.g., equine encephalitis viruses, rubella viruses); Flaviridae (e.g., dengue viruses, encephalitis viruses, yellow fever viruses); Coronaviridae (e.g., coronaviruses); Rhabdoriridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrahagic fever viruses); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 2 and 2, varicella zoster virus, cytomegalovirus (CMV), herpes viruses); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 132 internally transmitted; class 2=parenterally transmitted (i.e., Hepatitis C); Norwalk and related viruses, and astroviruses). (See also, Table 1).

As used herein, the term "receptor" means any polypeptide expressed by a cell that a virus can bind. Generally, such receptors are naturally present on the surface of a cell, but can be engineered. Receptor polypeptides may be non-covalently or covalently associated with other molecular entities, such as carbohydrates, fatty acids, lipids and the like. A receptor polypeptide may comprise one or multiple contiguous polypeptide segments that are covalently or non-covalently attached. Such molecular entities or other polypeptide sequences may be important for receptor conformation, for example, for binding to a coat polypeptide sequence. Thus, additional elements including molecules important for receptor conformation may therefore be included in the chimeric polypeptides of the present invention. The receptor polypeptide sequence can be either prokaryotic or eukaryotic in origin.

If eukaryotic, both plant and animal receptors are contemplated. Preferred animal receptors are mammalian, including human and primates, for example, chimps, apes, macaques, gibbons, orangutans and the like, as well as other animal species, including domestic animals and livestock. An example of a human receptor is CD4. Other examples of receptors include glycosaminoglycan and CD2, CR1. Additional receptors are known and are applicable in the compositions and methods of the invention (see, for example, Table 1 J see also "Cellular Receptors For Animal Viruses" Eckard Wimmer, ed; Cold Spring Harbor Press (1994)).

TABLE 1

| Receptor (binding subunit) | Virus (family) | References |
|---|---|---|
| Immunglobulin like Molecules | | |
| VCAM-1 | EMC-D (*Picornavaridae*) | Huber(1994) |
| [CAM-1] (first domain) | Major Group HRVs, CAV 13, 18 and 21 (*picornaviridae*) | Colonno et at. (1986) Greve et al. (1989) Staunton et al (1989) Tomassini et at. (1989) |
| PVR (first domain) | Polioviruses (*Picornaviridae*) (1989) | Koike et at. (1990) Mendelsotm et at. (1989) |
| CD4 (first domain) | HIV-1, 2; SIV (*Lentiviridae*) Human herpesvirus 7 | Daigleish et at. (1984); Klatzmaim et at. (1984) Lusso et at. (1994) |
| CEA, several member (first domain) | Mouse hepatitis virus (*Coronaviridae*) | Williams et al. (1978) |
| MHC 1 | Semliki Forest virus (*Togaviridae*) Factate dehydrogenuse virus Mouse cytomegatovirus (*Herpesviridae*) SV-40 | Hetenius et at. (1978) Otdstone et at. (1980) Inada and Mims (1984) Wykes et at. (1993) Breau et al. (1992) |
| MHCII | Visna virus (*Lentiviridae*) | Dalziel et at. (1991) |
| Integrins | | |
| VLA-2 (α-chain) | ECHO virus 1, 8 (*Picornaviridae*) | Bergelson et at. (1992, 1993) |
| (RGD-binding protein) | FMDV (*Picornaviridae*) | Fox et at. (1989) Mason et at. (1994) |

TABLE 1-continued

| Receptor (binding subunit) | Virus (family) | References |
|---|---|---|
| αvβ3 (vibronectin) | CAV 9, ECHO virus 1.8 (*Picornaviridae*) | Roivainen et at. (1994) |
| Transport proteins | | |
| Phosphate transporter | Gibbon ape leukemia virus (*Retroviridae*) | Johann et at. (1992) |
| Analogen | Amphotropic murine (*Retroviridae*) | Miller et al. (1994) |
| Cationic amino acid transporter | Ecotropic murine leukemia virus (*Retroviridae*) | Albritton et al. (1989) |
| Signaling Receptors | | |
| LDL Receptor protein family | Minor group HRVs (*Picornaviridae*) Subgroup A avian leucosis Sarcoma virus (family?) | Hofer et al. (1994) Bates et at. (1993) Connolly et at. (1994) |
| Acetylcholine receptor (α-1) | Rabies virus (*Rhabdoviridae*) | Leniz (1990) |
| EGF receptor | Vaccinia virus (*Poxviridae*) | Marsh and Eppstein (1987) |
| Leukocyte differentiation untigen [CD9] | Feline immunodeficiency Virus (*Lentiviridae*) | Willett et at. (1994) |
| Others | | |
| Aminopeptidase N | Human corona virus 229E (*Coronaviridae*) TGEV (*Coronaviridae*) | Yeager et at. (1992) Delmas et at. (1992) |
| Complement receptor CR2 | EBV (*Herpesviridae*) | McClure (1992) |
| High affinity laminin receptor | Sindbis virus (*Togaviridae*) | Wang et at. (1992) |
| Decay-accelerating factor [CD55] | ECHO viruses 7 (6, 11, 12, 20, 21) | Bergelson et at. (1994) |
| Membrane cofactor protein | Measles virus (*Morbilliviridae*) | Dorig et at. (1993) |
| Moesin | Measles virus (*Morbilliviridae*) | Dunster et at. (1994) |
| Glycophorin A | EMCV (*Picornaviridae*) Reovirus (*Reoviridae*) | Allaway and Barness (1986) Paul and Lee (1987) |
| Galactosylceramide | HIV-1 (*Lentiviridae*) | Bhat et al. (1991) |
| Erythrocyte P antigen | Parvovirus B19 (*Parvoviridae*) | Brown et al. (1993) |
| BLV Rcp. 1 | Bovine leukemia virus (*Retroviridae*) | Ban et al. (1993) |
| Sialoglycoprotein GP-2 | Sendai virus (*Paramyxoviridae*) | Suzuki et al. (1985) |
| Sialic acid | Influenza virus (*Orthomysoviridae*) Reoviridae (*Reoviridae*) Group A porcine rotavirus (*Rotaviridae*) Human coronavirus OC43, bovine coronavirus (*Coronaviridae*) | Herrler et al. (1985) Femandes et al. (1994) Roisma et al. (1994) Vlasak et al. (1988) |
| Heparan sulfate | Human cytomegalovirus (*Herpesviridae*) HSV | Compton et al. (1993) WuDunn and Spear (1989) |

As used herein, the term "co-receptor" means any receptor that is bound after or in conjunction with virus binding to receptor. Thus, co-receptors include any polypeptide or molecular entity present on a cell that facilitates virus entry, directly or indirectly, by binding to virus polypeptide-receptor complex. In addition to co-receptors that facilitate virus-entry into cells, also included are co-receptors that mediate cell attachment or tropism without directly or indirectly facilitating virus entry. Particular examples of co-receptors are the 7-transmembrane domain (7-TM) containing chemokine receptors, such as CCR5 and CXCR4, which can bind immunodeficiency virus. Additional co-receptors include CCR-2b, CCR3, CCR8, V28/CXCR1, US28, STRL 33/BOB/TYMSTR, GPR15/Bonzo and GPR1.

As used herein, the terms "polypeptide," "protein" and "peptide" are used interchangeably to denote a sequence polymer of at least two amino acids covalently linked by an amide bond, regardless of length or post-translational modification (e.g., glycosylation, phosphorylation, lipidation, myristilation, ubiquitination, etc.). D- and L-amino acids, and mixtures of D- and L-amino acids are also included.

Chimeric polypeptide refers to an amino acid sequence having two or more parts which generally are not found together in an amino acid sequence in nature.

As disclosed herein, a chimeric polypeptide having a CD4 polypeptide sequence and an HIV envelope gp120 polypeptide sequence that binds CD4 can bind to each other in the chimera when separated by an amino acid spacer sequence. The gp120-CD4 chimera is capable of binding a co-receptor, such as CCR5. Thus, in another embodiment, the chimeric polypeptide has a coat polypeptide sequence of a virus that binds a co-receptor.

CD4 appears to be the target for entry of a variety of viruses associated with immunodeficiency. For example, cells of the immune system, such as lymphocytes and macrophages express CD4, and are susceptible to infection by HIV, SIV, herpes virus 7 and many other viruses. As used herein, the term "immunodeficiency," when used in reference to a virus, means that the virus is capable of infecting cells of immune origin or cells that participate in immune responsiveness, and generally such infection can compromise an infected host's immune function. Thus, the invention is applicable to any virus coat polypeptide of any virus or virus strain that can bind CD4.

In accordance with the present invention, there are provided chimeric polypeptides having an immunodeficiency virus envelope polypeptide sequence. In various aspects, the envelope polypeptide sequence is a polypeptide sequence of HIV, HTLV, SIV, FeLV, FPV and Herpes virus. In other aspects, the virus is a macrophage tropic or a lymphocyte tropic HIV. In another aspect, the HIV is HIV-1 or HIV-2. In various other aspects, the envelope polypeptide sequence is gp120, gp160 or gp41.

Receptor and virus coat polypeptide sequences of the present chimeric polypeptide require a spacer region between them, for example, for forming an interacting complex between the two polypeptides. Although not wishing to be bound by theory, it is believed that the spacer allows the movement or flexibility between receptor and virus coat polypeptide sequences to form an interacting complex.

As used herein, the term "spacer" refers to a physical or chemical moiety, or covalent or non-covalent bond of any size or nature that connects the virus coat polypeptide sequence to the receptor polypeptide sequence while affording the needed flexibility or movement for forming an interacting complex. In the present invention, the spacer preferably links the two polypeptide sequences in an "end to end" orientation. "End to end" means that the amino or carboxyl terminal amino acid of the coat polypeptide is connected to the amino or carboxyl terminal amino acid of the receptor polypeptide sequence. Thus, a spacer can connect the carboxyl terminal amino acid of the coat polypeptide sequence to the amino terminal amino acid of the receptor polypeptide sequence, as exemplified herein for HIV gp120 and CD4, for example. Alternatively, the spacer can connect the amino terminal amino acid of the coat polypeptide to the carboxyl terminal amino acid of the receptor polypeptide or the carboxyl terminal amino acids of the polypeptide sequences or the two amino terminal amino acids of the polypeptide sequences.

Particular examples of spacers include one or more amino acids or a peptidomimetic. An amino acid spacer can essentially be any length, for example, as few as 5 or as many as 200 or more amino acids. Thus, an amino acid spacer can have from about 10 to about 100 amino acids, or have from about 15 to about 50 amino acids. Preferably, the spacer has from about 20 to about 40 amino acids. Other examples of spacers include a disulfide linkage between the termini of the polypeptide sequences. A carbohydrate spacer also is contemplated. Those skilled in the art will know or can readily ascertain other moieties that can function to allow formation of an interacting complex between the virus coat polypeptide sequence and receptor polypeptide sequence.

Figure 9:
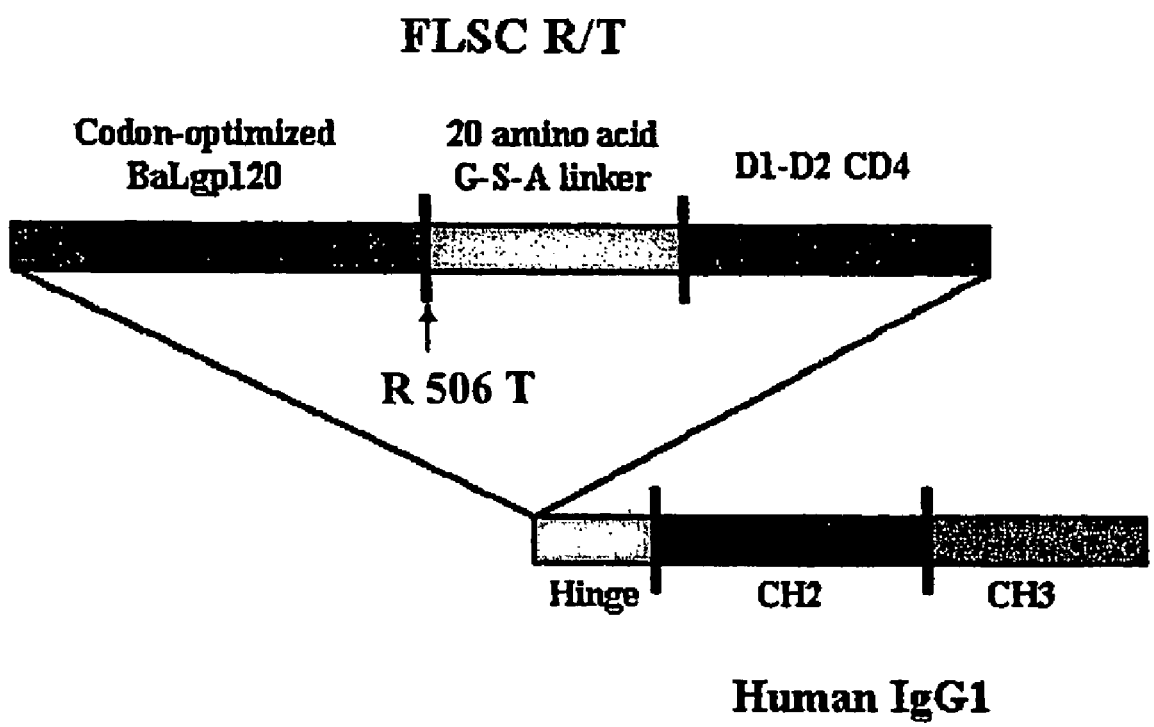
FIG. 9 is a diagram of chimeric gp120-CD4-IgG1 gene showing the coding domains. It is essentially the original gp120-CD4 subcloned into a plasmid that has the IgG1 heavy chain hinge CH2 and CH3 regions thereby permitting expression of chimeric gp120-CD4-IgG1 polypeptide.

Receptor and coat polypeptide sequences can be of any amino acid length. Preferably, they have a length that allows the polypeptide sequences to bind to each other when in a chimeric polypeptide. Thus, receptor and coat polypeptide sequences include native full-length receptor and full-length coat polypeptide sequences as well as parts of the polypeptide sequences. For example, amino acid truncations, internal deletions or subunits of receptor, and coat polypeptide sequences are included. Preferably, such modified forms are capable of interacting with each other. For example, it is preferable that a truncated or deleted coat polypeptide sequence is capable of interacting with a receptor polypeptide sequence. An example of a truncated receptor polypeptide sequence is the CD4 D1 and D2 domains, which are capable of interacting with HIV envelope polypeptide sequence (FIG. 9). An example of a truncated coat polypeptide sequence is a truncated HIV gp120 lacking the amino terminal 60 amino acids and carboxy terminal 20 amino acids (e.g., in TcSC).

Thus, in accordance with the present invention, chimeric polypeptides, including truncated or internally deleted sequences, are provided. In one embodiment, the virus coat polypeptide sequence or the receptor polypeptide sequence has one or more amino acids removed in comparison to their corresponding full-length polypeptide sequence. In one aspect, the truncated virus coat polypeptide sequence is an HIV envelope polypeptide sequence and, in another aspect, the truncated receptor polypeptide sequence is a CD4 sequence. As exemplified herein, the truncated HIV envelope polypeptide sequence is a gp120 lacking the amino terminal 60 amino acids or the carboxy terminal 20 amino acids, and a truncated CD4 polypeptide comprising the D1 and D2 domains. In various other aspects, the chimeric polypeptide comprises an internally deleted virus coat polypeptide sequence or an internally deleted CD4 polypeptide sequence.

In addition to the truncated, internally deleted and subunit polypeptide sequences, additional polypeptide sequence modifications are included. Such modifications include minor substitutions, variations, or derivitizations of the amino acid sequence of one or both of the polypeptide sequences that comprise the chimeric polypeptide, so long as the modified chimeric polypeptide has substantially the same activity or function as the unmodified chimeric polypeptide. For example, a virus coat or receptor polypeptide sequence may have carbohydrates, fatty acids (palmitate, myristate), lipids, be phosphorylated or have other post-translational modifications typically associated with polypeptide sequences.

Another example of a modification is the addition of a heterologous domain that imparts a distinct functionality upon either of the two polypeptides or the chimeric polypeptide. A heterologous domain can be any small organic or inorganic molecule or macromolecule, so long as it imparts an additional function. Heterologous domains may or may not affect interaction or affinity between virus coat polypeptide and receptor polypeptide. Particular examples of heterologous domains that impart a distinct function include an amino acid sequence that imparts targeting (e.g., receptor ligand, antibody, etc.), immunopotentiating function (e.g., immunoglobulin, an adjuvant), enable purification, isolation or detection (e.g., myc, T7 tag, polyhistidine, avidin, biotin, lectins, etc.).

Particular heterologous domains may include a c-myc polypeptide sequence and/or an IgG1 heavy chain polypeptide sequence. A heterologous domain can have multiple functions. For example, IgG1 can function as an immunopotentiator in vivo, as well as function as an adhesive molecule that can be purified, isolated, or detected (e.g., by reaction with a secondary antibody having an enzymatic activity, such as horseradish peroxidase or alkaline phosphatase). The skilled artisan will know of other heterologous domains and can select them as appropriate depending on the application and the function desired.

Thus, in accordance with the present invention, there are provided chimeric polypeptides having one or more heterologous domains. In one embodiment, the heterologous domain is a c-myc polypeptide sequence glu-gln-lys-leu-ile-ser-glu-glu-asp-leu; (SEQ ID NO: 14). In another embodiment, the heterologous domain is an immunoglobulin polypeptide sequence comprising a heavy chain (SEQ ID NO: 32).

Receptor and coat polypeptide sequences can be of any amino acid length. Preferably, they have a length that allows the polypeptide sequences to bind to each other when in a chimeric polypeptide. Thus, receptor and coat polypeptide sequences include native full-length receptor and full-length coat polypeptide sequences as well as parts of the polypeptide sequences.

In one aspect, the present invention comprises a full-length single chain (FLSC) chimeric polypeptide comprising a HIV gp120 (BaL strain), an amino acid spacer polypeptide, a CD4 polypeptide sequence comprising the D1D2 domain and a myc peptide "tag" (SEQ ID NO.: 2) or at least 95% sequence identity to SEQ ID NO: 2 that encodes the chimeric polypeptide.

In another aspect, the prevention invention comprises a FLSC polypeptide having single mutation in a furin cleavage site of the FLSC polypeptide, wherein an R is changed to a T, at the c-terminus of gp120 (FLSC-R/T) or at least 95% sequence identity to SEQ ID NO: 2 that encodes the chimeric polypeptide. Specifically, FLSC R/T contains an arginine to a threonine mutation at amino acid 506 (SEQ ID NO.: 4).

As exemplified herein, polypeptide sequence include substitutions, variations, or derivitizations of the amino acid sequence of one or both of the polypeptide sequences that comprise the chimeric polypeptide, so long as the modified chimeric polypeptide has substantially the same activity or function as the unmodified chimeric polypeptide. For example, a virus coat or receptor polypeptide sequence may have carbohydrates, fatty acids (palmitate, myristate), lipids, be phosphorylated or have other post-translational modifications typically associated with polypeptide sequences.

In yet another aspect, the virus coat polypeptide sequence or the receptor polypeptide sequence has one or more amino acid substitutions in comparison to their corresponding unmodified polypeptide sequences. For example, a nucleotide sequence (SEQ ID NO: 5) is provided that encodes for a polypeptide that includes a CD4 mimicking receptor that shows substantially the same activity or improved immune response. Specifically, the gene sequence encoding the amino acid sequence of KKVVLGKKGDTVELTCTASQKK-SIQFHW in CD4 DID2 domain of the chimeric polypeptide FLSC-R/T (SEQ ID NO: 4) is substituted with a nucleotide sequence (SEQ ID NO: 19) that encodes an amino acid sequence of CNLARCQLRCKSLGLLGKCAGSFCACGP (amino acids 528-556 (SEQ ID NO: 20)) which is referred to hereinafter as FLSC-R/T CD4M9. (SEQ ID NO.: 6).

As used herein, the term "substantially the same activity or function," when used in reference to a chimeric polypeptide so modified, means that the polypeptide retains most, all or more of the activity associated with the unmodified polypeptide, as described herein or known in the art. Similarly, modifications that do not affect the ability of chimeric polypeptide to interact with co-receptor are included herein. Likewise, chimeric polypeptide modifications that do not affect the ability to induce a more potent immune response than administration of the virus coat protein alone are included.

Modified chimeric polypeptides that are "active" or "functional" included herein can be identified through a routine functional assay. For example, by using antibody binding assays, co-receptor binding assays, or determining induction of epitopes exposed in a transition state complex normally hidden when the two polypeptide sequences do not bind, one can readily determine whether the modified chimeric polypeptide has activity.

Chimeric polypeptides that induce a more potent immune response can be identified by measuring antibody titers following administration of the chimera to a subject, for example. Modifications that destroy the interaction between the virus coat polypeptide sequence and the receptor polypeptide sequence, or the ability of a chimeric polypeptide having a virus coat polypeptide sequence and receptor sequence which do not interact to induce a more potent immune response, do not have substantially the same activity or function as the corresponding, unmodified chimeric polypeptide and, as such, are not included.

As used herein, the terms "homology" or "homologous," used in reference to polypeptides, refers to amino acid sequence similarity between two polypeptides. When an amino acid position in both of the polypeptides is occupied by identical amino acids, they are homologous at that position. Thus, by "substantially homologous" means an amino acid sequence that is largely, but not entirely, homologous, and which retains most or all of the activity as the sequence to which it is homologous.

As the modified chimeric polypeptides will retain activity or function associated with unmodified chimeric polypeptide, modified chimeric polypeptides will generally have an amino acid sequence "substantially identical" or "substantially homologous" with the amino acid sequence of the unmodified polypeptide. As used herein, the term "substantially identical" or "substantially homologous," when used in reference to a polypeptide sequence, means that a sequence of the polypeptide is at least 50% identical to a reference sequence. Modified polypeptides and substantially identical polypeptides will typically have at least 70%, alternatively 85%, more likely 90%, and most likely 95% homology to a reference polypeptide. For polypeptides, the length of comparison to obtain the above-described percent homologies between sequences will generally be at least 25 amino acids, alternatively at least 50 amino acids, more likely at least 100 amino acids, and most likely 200 amino acids or more.

As set forth herein, substantially identical or homologous polypeptides include additions, truncations, internal deletions or insertions, conservative and non-conservative substitutions, or other modifications located at positions of the amino acid sequence which do not destroy the function of the chimeric polypeptide (as determined by functional assays, e.g., as described herein). A particular example of a substitution is where one or more amino acids is replaced by another, chemically or biologically similar residue. As used herein, the term "conservative substitution" refers to a substitution of one residue with a chemically or biologically similar residue. Examples of conservative substitutions include the replacement of a hydrophobic residue, such as isoleucine, valine, leucine, or methionine for another, the replacement of a polar residue for another, such as the substitution of arginine for lysine, glutamic for aspartic acids, or glutamine for asparagine, and the like. Those of skill in the art will recognize the numerous amino acids that can be modified or substituted with other chemically similar residues without substantially altering activity.

Substantially identical or homologous polypeptides also include those having modifications that improve or confer an additional function or activity. For example, FLSC R/T has a mutated furin site which increases stability of the modified FLSC (see, e.g., FIG. 13).

Modified polypeptides further include "chemical derivatives," in which one or more of the amino acids therein have a side chain chemically altered or derivatized. Such derivatized polypeptides include, for example, amino acids in which free amino groups form amine hydrochlorides, p-toluene sulfonyl groups, carobenzoxy groups; the free carboxy groups form salts, methyl and ethyl esters; free hydroxyl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, and so forth. Also included are D-amino acids and amino acid derivatives that can alter covalent bonding, for example, the disulfide linkage that forms between two cysteine residues that produces a cyclized polypeptide.

As used herein, the terms "isolated" or "substantially pure," when used as a modifier of invention chimeric polypeptides, sequence fragments thereof, and polynucleotides, means that they are produced by human intervention and are separated from their native in vivo-cellular environment. Generally, polypeptides and polynucleotides so separated are substantially free of other proteins, nucleic acids, lipids, carbohydrates or other materials with which they are naturally associated.

Typically, a polypeptide is substantially pure when it is at least 60%, by weight, free from the proteins and other molecules with which it is naturally associated. The preparation is likely at least 75%, more likely at least 90%, and most likely at least 95%, by weight pure. Substantially pure chimeric polypeptide can be obtained, for example, by expressing a polynucleotide encoding the polypeptide in cells and isolating the polypeptide produced. For example, as set forth in the examples, expression of a recombinant polynucleotide encoding a gp120-CD4 polypeptide in mammalian cells allows isolating the chimerical polypeptide from the culture media using an immunoaffinity column. Alternatively, the chimeric polypeptide can be chemically synthesized. Purity can be measured by any appropriate method, e.g., polyacrylamide gel electrophoresis, and subsequent staining of the gel (e.g., silver stain) or by HPLC analysis.

The chimeric polypeptides of the present invention and modifications thereof can be prepared by a variety of methods known in the art. The polypeptide modifications can be introduced by site-directed (e.g., PCR based) or random mutagenesis (e.g., EMS) by exonuclease deletion, by chemical modification, or by fusion of polynucleotide sequences encoding heterologous domain, for example. Chimeric polypeptides can be obtained by expression of a polynucleotide encoding the polypeptide in a host cell, such as a bacteria, yeast or mammalian cell, and purifying the expressed chimeric polypeptide by purification using typical biochemical methods (e.g., immunoaffinity purification, gel purification, expression screening etc). Other well-known methods are described in Deutscher et al., (*Guide to Protein Purification: Methods in Enzymology*, Vol. 182, Academic Press (1990), which is incorporated herein by reference).

The present invention further provides polynucleotide sequences encoding chimeric polypeptides, fragments thereof, and complementary sequences. In one embodiment, nucleic acids encode the chimeric gp120-CD4 polypeptide exemplified herein. For example, SEQ ID NO.: 1 defines the sequence encoding FLSC described hereinabove comprising a nucleotide sequence encoding gp120 (SEQ ID 23) and CD4 D1D2 (SEQ ID NO: 25). SEQ. ID NO: 3 defines a sequence encoding FLSC R/T wherein an arginine amino acid is substituted for a threonine at the c-terminal of the gp120, a suspect furin cleavage site in gp120, thereby improving the stability of the FLSC-R/T over FLSC. The nucleotide sequence of FLSC-RT comprises a modified gp120 encoded by SEQ ID NO: 29 and CD4D1D2 (SEQ ID NO: 25). Still further, the present invention provides for polynucleotide sequence SEQ ID NO.: 5 that encodes for a chimeric polypeptide FLSC R/T CD4M9 comprising a substituted furin cleavage site and further provides for replacement of gene sequence encoding the CD4 D1D2 region with a sequence that encodes for an amino acid sequence that mimics a CD4 receptor, thereby providing for an improved immune response and additional stability relative to FLSC or FLSC-R/T. The FLSC R/T CD4M9 is encoded by nucleotide sequences comprising SEQ ID NO: 29 that encodes for a modified gp120 and SEQ ID NO: 19 encoding for CD4M9. The FLSC R/T CD4M9 chimeric polypeptide may additionally comprise SEQ ID NOs: 23 and 19.

In yet another embodiment, TsSC (SEQ ID NO: 12) encode a gp120-CD4 polypeptide (SEQ ID NO: 13) in which the gp120 has amino acid sequences truncated from the amino and carboxy terminus. The nucleotide sequence of TsSC comprises a sequence (SEQ ID NO: 27) that encodes for a truncated gp120 and CD4D1D2 (SEQ ID NO: 25). In another embodiment, a chimeric polypeptide gp120-CD4-IgG1 is encoded by nucleotide SEQ ID NO: 1 with an additional tag (SEQ ID NO: 31).

As used herein, the terms "nucleic acid," "polynucleotide," "oligonucleotide," and "primer" are used interchangeably to refer to deoxyribonucleic acid (DNA) or ribonucleic (RNA), either double- or single-stranded, linear or circular. RNA can be unspliced or spliced mRNA, rRNA, tRNA, or antisense RNAi. DNA can be complementary DNA (cDNA), genomic DNA, or an antisense. Specifically included are nucleotide analogues and derivatives, such as those that are resistant to nuclease degradation, which can function to encode an invention chimeric polypeptide. Nuclease resistant oligonucleotides and polynucleotides are particularly useful for the present nucleic acid vaccines described herein.

An "isolated" or "substantially pure" polynucleotide means that the nucleic acid is not immediately contiguous with the coding sequences with either the 5' end or the 3' end with which it is immediately contiguous in the naturally occurring genome of the organism from which it is derived. The term therefore includes, for example, a recombinant DNA (e.g., a cDNA or a genomic DNA fragment produced by PCR or restriction endonuclease treatment produced during cloning), as well as a recombinant DNA incorporated into a vector, an autonomously replicating plasmid or virus, or a genomic DNA of a prokaryote or eukaryote. It also includes a recombinant DNA part of a chimera or fusion, for example. The term therefore does not include nucleic acids present but uncharacterized among millions of sequences in a genomic or cDNA library, or in a restriction digest of a library fractionated on a gel.

The polynucleotides of the invention also include nucleic acids that are degenerate as a result of the genetic code. There are 20 natural amino acids, most of which are specified by more than one codon. All degenerate polynucleotide sequences are included that encode invention chimeric polypeptides.

The polynucleotides sequences of the present invention can be obtained using standard techniques known in the art (e.g., molecular cloning, chemical synthesis) and the purity can be determined by polyacrylamide or agarose gel electrophoresis, sequencing analysis, and the like. Polynucleotides also can be isolated using hybridization or computer-based techniques that are well known in the art. Such techniques include, but are not limited to: (1) hybridization of genomic DNA or cDNA libraries with probes to detect homologous nucleotide sequences; (2) antibody screening of polypeptides expressed by DNA sequences (e.g., using an expression library); (3) polymerase chain reaction (PCR) of genomic DNA or cDNA using primers capable of annealing to a nucleic acid sequence of interest; (4) computer searches of sequence databases for related sequences; and (5) differential screening of a subtracted nucleic acid library. Thus, to obtain other receptor encoding polynucleotides, such as those encoding CD4, for example, libraries can be screened for the presence of homologous sequences.

The invention also includes substantially homologous polynucleotides. As used herein, the term "homologous," when used in reference to nucleic acid molecule, refers to similarity between two nucleotide sequences. When a nucleotide position in both of the molecules is occupied by identical nucleotides, then they are homologous at that position. "Substantially homologous" nucleic acid sequences are at least 50% homologous, more likely at least 75% homologous, and most likely 90% or more homologous. As with substantially homologous invention chimeric polypeptides, polynucleotides substantially homologous to invention polynucleotides encoding chimeric polypeptides encode polypeptides that retain most or all of the activity or function associated with the sequence to which it is homologous. For polynucleotides, the length of comparison between sequences will generally be at least 30 nucleotides, alternatively at least 50 nucleotides, more likely at least 75 nucleotides, and most likely 110 nucleotides or more. Algorithms for identifying homologous sequences that account for polynucleotide sequence gaps and mismatched oligonucleotides are known in the art, such as BLAST (see, e.g., Altschul et al., *J. Mol. Biol.* 15:403-10 (1990)).

In addition, polynucleotides are useful as hybridization probes in order to identify the presence or amount of a polynucleotide encoding a chimeric polypeptide, for example, mRNA (Sambrook et al., *Molecular Cloning: A Laboratory Manual*, Cold Spring Harbor Laboratory, N.Y. (1989)). Typically such probes are designed to be specific for the desired sequence in order to decrease the probability of hybridizing to unrelated sequences. Such probes can be modified so as to be detectable using radionuclides, luminescent moieties, and so forth. Hybridization conditions also can be modified in order to achieve the desired specificity. For example, a moderately stringent hybridization condition may include: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash). An example of moderately-high stringency hybridization conditions is as follows: 0.1×SSC/0.1% SDS at about 52° C. (moderately-high stringency wash). An example of high stringency hybridization conditions is as follows: 0.1×SSC/0.1% SDS at about 65° C. (high stringency wash).

The polynucleotides of the present invention can, if desired: be naked or be in a carrier suitable for passing through a cell membrane (e.g., polynucleotide-liposome complex or a colloidal dispersion system), contained in a vector (e.g., retrovirus vector, adenoviral vectors, and the like), linked to inert beads or other heterologous domains (e.g., antibodies, ligands, biotin, streptavidin, lectins, and the like), or other appropriate compositions disclosed herein or known in the art. Thus, viral and non-viral means of polynucleotide delivery can be achieved and are contemplated. The polynucleotides of the present invention can also contain additional nucleic acid sequences linked thereto that encode a polypeptide having a distinct functionality, such as the various heterologous domains set forth herein.

The polynucleotides of the present invention can also be modified, for example, to be resistant to nucleases to enhance their stability in a pharmaceutical formulation. The described polynucleotides are useful for encoding chimeric polypeptides of the present invention, especially when such polynucleotides are incorporated into expression systems disclosed herein or known in the art. Accordingly, polynucleotides including an expression vector are also included.

For propagation or expression in cells, polynucleotides described herein can be inserted into a vector. The term "vector" refers to a plasmid, virus, or other vehicle known in the art that can be manipulated by insertion or incorporation of a nucleic acid. Such vectors can be used for genetic manipulation (i.e., "cloning vectors") or can be used to transcribe or translate the inserted polynucleotide (i.e., "expression vectors"). A vector generally contains at least an origin of replication for propagation in a cell and a promoter. Control elements, including promoters present within an expression vector, are included to facilitate proper transcription and translation (e.g., splicing signal for introns, maintenance of the correct reading frame of the gene to permit in-frame translation of mRNA and stop codons). In vivo or in vitro expression of the polynucleotides described herein can be conferred by a promoter operably linked to the nucleic acid. "Promoter" refers to a minimal nucleic acid sequence sufficient to direct transcription of the nucleic acid to which the promoter is operably linked (see, e.g., Bitter et al., *Methods in Enzymology*, 153:5 16-544 (1987)). Promoters can constitutively direct transcription, can be tissue-specific, or can render inducible or repressible transcription; such elements are generally located in the 5' or 3' regions of the gene so regulated.

In the present invention, for viruses that bind a co-receptor, it is advantageous to introduce and express a polynucleotide encoding a chimeric polypeptide into the cells that are susceptible to viral infection (e.g., cells that express the co-receptor). In this way, the expressed chimeric polypeptide will be secreted by the transformed susceptible cell in close proximity to the co-receptor, thereby inhibiting or preventing access of the virus to the co-receptor which, in turn, inhibits or prevents viral infection of cells. To this end, a tissue-specific promoter can be operably linked to the polynucleotide sequence to confer expression of the chimeric polypeptide in an appropriate target cell.

As used herein, the phrase "tissue-specific promoter" means a promoter that is active in particular cells or tissues that confers expression of the operably linked polynucleotide in the particular cells, e.g., liver cells, hematopoietic cells, or cells of a specific tissue within an animal. The term also covers so-called "leaky" promoters, which regulate expression of a selected DNA primarily in one tissue, but cause expression in one or more other tissues as well. An inducible promoter can also be used to modulate expression in cells. "Inducible promoter" means a promoter whose activity level increases in response to treatment with an external signal or agent (e.g., metallothionein IIA promoter, heat shock promoter). A "repressible promoter" or "conditional promoter" means a promoter whose activity level decreases in response to a repressor or an equivalent compound. When the repressor is no longer present, transcription is activated or derepressed. Such promoters may be used in combination and also may include additional DNA sequences that are necessary for transcription and expression, such as introns and enhancer sequences.

As used herein, the term "operably linked" means that a selected polynucleotide (e.g., encoding a chimeric polypeptide) and regulatory sequence(s) are connected in such a way as to permit transcription when the appropriate molecules (e.g., transcriptional activator proteins) are bound to the regulatory sequence(s). Typically, a promoter is located at the 5' end of the polynucleotide and may be in close proximity of the transcription initiation site to allow the promoter to regulate expression of the polynucleotide. However, indirect operable linkage is also possible when a promoter on a first vector controls expression of a protein that, in turn, regulates a promoter controlling expression of the polynucleotide on a second vector.

When cloning in bacterial systems, constitutive promoters, such as T7 and the like, as well as inducible promoters, such as pL of bacteriophage gamma, plac, ptrp, ptac, may be used. When cloning in mammalian cell systems, constitutive promoters, such as SV40, RSV and the like, or inducible promoters derived from the genome of mammalian cells (e.g., the metallothionein promoter) or from mammalian viruses (e.g., the mouse mammary tumor virus long terminal repeat, the adenovirus late promoter), may be used. Promoters produced by recombinant DNA or synthetic techniques may also be used to provide for transcription of the nucleic acid sequences of the invention.

Mammalian expression systems that utilize recombinant viruses or viral elements to direct expression may be engineered. For example, when using adenovirus expression vectors, the nucleic acid sequence may be ligated to an adenovirus transcription/translation control complex, e.g., the late promoter and tripartite leader sequence. Alternatively, the vaccinia virus 7.5K promoter may be used (see, e.g., Mackett et al., *Proc. Natl. Acad. Sci. USA*, 79:7415-7419 (1982); Mackett et al., *J. Virol.*, 49:857-864 (1984); Panicali et al., *Proc. Natl. Acad. Sci. USA*, 79:4927-4931 (1982)).

Mammalian expression systems further include vectors specifically designed for "gene therapy" methods, including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), and retroviral vectors (U.S. Pat. Nos. 5,624,820, 5,693,508 and 5,674,703 and WIPO publications WO92/05266 and WO92/14829). The chimeric polypeptide encoding gene can be introduced into vaccine delivery vehicles, such as attenuated vaccinia (M. Girard et al., *C R Acad Sci III.*, 322:959-66 (1999); B. Moss et al., AIDS, 2 Suppl 1:S103-5 (1988)), Semiliki-forest virus (M. Girard et al., *C R Acad Sci III.*, 322:959-66 (1999); S. P. Mossman et al., *J Virol.*, 70: 19.53-60 (1996)), or Salmonella (R. Powell et al., In: *Molecular Approaches to the control of infectious diseases*, pp. 183-187, F. Bran, E. Norrby, D. Burton, and J. Meckalanos (eds), Cold Spring Harbor Press, Cold Spring Harbor, N.Y. (1996); M. T. Shata et al., *Mol Med Today*, 6:66-71 (2000)) to provide an efficient and reliable means for the expression of properly associated and folded virus coat protein and receptor sequences, for example, gp120 and CD4.

Vectors based on bovine papilloma virus (BPV) have the ability to replicate as extra-chromosomal elements (Sarver et al., *Mol. Cell. Biol.*, 1:486 (1981)). Shortly after entry of an extra-chromosomal vector into mouse cells, the vector replicates to about 100 to 200 copies per cell. Because transcription of the inserted cDNA does not require integration of the plasmid into the host's chromosome, a high level of expression occurs. Such vectors also have been employed in gene therapy (U.S. Pat. No. 5,719,054). CMV-based vectors also are included (U.S. Pat. No. 5,561,063).

For yeast expression, a number of vectors containing constitutive or inducible promoters may be used (see, e.g., *Current Protocols in Molecular Biology*, Vol. 2, Ch. 13, ed. Ausubel et al., Greene Publish. Assoc. & Wiley Interscience (1988); Grant et al., "Expression and Secretion Vectors for Yeast," in *Methods in Enzymology*, Vol. 153, pp. 516-544, eds. Wu & Grossman, 3 1987, Acad. Press, N.Y. (1987); Glover, *DNA Cloning, Vol. II*, Ch. 3, IRL Press, Wash., D.C. (1986); Bitter, "Heterologous Gene Expression in Yeast," *Methods in Enzymology*, Vol. 152, pp. 673-684, eds. Berger & Kimmel, Acad. Press, N.Y. (1987); and *The Molecular Biology of the Yeast Saccharomyces*, eds. Strathem et al., Cold Spring Harbor Press, Vols. I and II (1982)). A constitutive yeast promoter, such as ADH or LEU2, or an inducible promoter, such as GAL, may be used ("Cloning in Yeast," R. Rothstein, In: *DNA Cloning, A Practical Approach*, Vol. 11, Ch. 3, ed. D. M. Glover, IRL Press, Wash., D.C. (1986)). Alternatively, vectors that facilitate integration of foreign nucleic acid sequences into a yeast chromosome, via homologous recombination, for example, are known in the art and can be used. Yeast artificial chromosomes (YAC) are typically used when the inserted polynucleotides are too large for more conventional yeast expression vectors (e.g., greater than about 12 kb). The polynucleotides may be inserted into an expression vector for expression in vitro (e.g., using in vitro transcription/translation kits, which are available commercially), or may be inserted into an expression vector that contains a promoter sequence that facilitates expression in either prokaryotes or eukaryotes by transfer of an appropriate nucleic acid into a suitable cell, organ, tissue, or organism in vivo.

As used herein, a "transgene" is any piece of a polynucleotide inserted by artifice into a host cell, and becomes part of the organism that develops from that cell. A transgene can include one or more promoters and any other DNA, such as introns, necessary for expression of the selected DNA, all operably linked to the selected DNA, and may include an enhancer sequence. A transgene may include a polynucleotide that is partly or entirely heterologous (i.e., foreign) to the transgenic organism, or may represent a gene homologous to an endogenous gene of the organism. Transgenes may integrate into the host cell's genome or be maintained as a self-replicating plasmid.

As used herein, a "host cell" is a cell into which a polynucleotide is introduced that can be propagated, transcribed, or encoded polypeptide expressed. The term also includes any progeny of the subject host cell. It is understood that all progeny may not be identical to the parental cell, since there may be mutations that occur during replication. Host cells include but are not limited to bacteria, yeast, insect, and mammalian cells. For example, bacteria transformed with recombinant bacteriophage polynucleotide, plasmid nucleic acid, or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV), or transformed with recombinant plasmid expression vectors (e.g., Ti plasmid), insect cell systems infected with recombinant virus expression vectors (e.g., baculovirus), or animal cell systems infected with recombinant virus expression vectors (e.g., retroviruses, adenovirus, vaccinia virus), or transformed animal cell systems engineered for stable expression.

For long-term expression of invention polypeptides, stable expression is preferred. Thus, using expression vectors containing viral origins of replication cells can be transformed with a nucleic acid controlled by appropriate control elements (e.g., promoter/enhancer sequences, transcription terminators, polyadenylation sites, etc.). Although not wishing to be bound or so limited by any particular theory, stable maintenance of expression vectors in mammalian cells is believed to occur by integration of the vector into a chromosome of the host cell. Optionally, the expression vector also can contain a nucleic acid encoding a selectable marker conferring resistance to a selective pressure or reporter indicating the cells into which the gene has been introduced, thereby allowing cells having the vector to be identified, grown, and expanded. As used herein, "reporter gene" means a gene whose expression may be assayed; such genes include, without limitation, lacZ, amino acid biosynthetic genes, e.g. the yeast LEI2 gene, luciferase, or the mammalian chloramphenicol transacetylase (CAT) gene. Reporter genes may be integrated into the chromosome or may be carried on autonomously replicating plasmids (e.g., yeast 2 micron plasmids). Alternatively, the selectable marker can be on a second vector cotransfected into a host cell with a first vector containing an invention polynucleotide.

A number of selection systems may be used, including, but not limited to the neomycin gene, which confers resistance to the aminoglycoside G418 (Colberre-Garapin et al., *J Mol. Biol.*, 150: 1 (1981)) and the hygromycin gene, which confers resistance to hygromycin (Santerre et al, *Gene*, 30: 147 (1984)). Recently, additional selectable genes have been described, namely trpB, which allows cells to utilize indole in place of tryptophan; hisD, which allows cells to utilize histinol in place of histidine (Hartman et al., *Proc. Natl. Acad. Sci. USA*, 85:8047 (1988)); and ODC (ornithine decarboxylase), which confers resistance to the ornithine decarboxylase inhibitor, 2-(difluoromethyl)-DL-ornithine, DFMO (McConlogue, In: *Current Communications in Molecular Biology*, Cold Spring Harbor Laboratory, ed. (1987)).

As used herein, the term "transformation" means a genetic change in a cell following incorporation of a polynucleotide (e.g., a transgene) exogenous to the cell. Thus, a "transformed cell" is a cell into which, or a progeny of which, a polynucleotide has been introduced by means of recombinant techniques. Transformed cells do not include an entire human being. Transformation of a host cell may be carried out by conventional techniques known to those skilled in the art. When the host cell is a eukaryote, methods of DNA transformation include, for example, calcium phosphate, microinjection, electroporation, liposomes, and viral vectors. Eukaryotic cells also can be co-transformed with invention polynucleotide sequences or fragments thereof, and a second DNA molecule encoding a selectable marker, as described herein or otherwise known in the art. Another method is to use a eukaryotic viral vector, such as simian virus 40 (SV40) or bovine papilloma virus, to transiently infect or transform eukaryotic cells, and express the protein (see, e.g., *Eukaryotic Viral Vectors*, Cold Spring Harbor Laboratory, Gluzman ed. (1982)). When the host is prokaryotic (e.g., *E. coli*), competent cells that are capable of DNA uptake can be prepared from cells harvested after exponential growth phase and subsequently treated by the $CaCl_2$ method using procedures well-known in the art. Transformation of prokaryotes also can be performed by protoplast fusion of the host cell.

Chimeric polypeptides, polynucleotides, and expression vectors containing same of the present invention can be encapsulated within liposomes using standard techniques and introduced into cells or whole organisms. Cationic liposomes are preferred for delivery of polynucleotides. The use of liposomes for introducing various compositions in vitro or in vivo, including proteins and polynucleotides, is known to those of skill in the art (see, for example, U.S. Pat. Nos. 4,844,904, 5,000,959, 4,863,740 and 4,975,282).

Liposomes can be targeted to a cell type or tissue of interest by the addition to the liposome preparation of a ligand, such as a polypeptide, for which a corresponding cellular receptor has been identified. For example, in the case of a virus that infects a CD4+ cell, CD4+ cells are an appropriate target and HIV gp120 could be an appropriate ligand for intracellular introduction of a liposome containing a chimeric polypeptide or polynucleotide sequence as described herein. Monoclonal antibodies can also be used for targeting; many such antibodies specific for a wide variety of cell surface proteins are known to those skilled in the art and are available. The selected ligand is covalently conjugated to a lipid anchor in either preformed liposomes or are incorporated during liposome preparation (see Lee & Low, *J Biol. Chem.*, 269:3 198 (1994); Lee & Low *Biochem. Biophys. Actu*, 1233: 134 (1995)).

The chimeric polypeptides and polynucleotides encoding same of the present invention can be introduced into a whole organism. In particular, for chimeric polypeptides that contain a virus coat polypeptide that binds to co-receptor, transgenic animals expressing invention chimeric polypeptides would be useful for studying the long-term effects of chimeric expression, as well as determining whether the expressed chimeric polypeptide could protect or inhibit infection by a corresponding virus.

Thus, in another embodiment, the invention provides non-human transgenic animals that express chimeric polypeptides. Preferred animals are susceptible to viral infection for which a corresponding receptor polypeptide sequence is known. Preferred animals are those susceptible to immunodeficiency virus infection, including mammals, such as non-human primates (e.g., macaques, chimpanzees, apes, gibbons, orangutans, etc.), domestic animals, and livestock, as described herein.

The term "transgenic animal" refers to any animal whose somatic or germ line cells bear genetic information received, directly or indirectly, by deliberate genetic manipulation at the subcellular level, such as by microinjection or infection with recombinant virus. The term "transgenic" further includes cells or tissues (i.e., "transgenic cell," "transgenic tissue") obtained from a transgenic animal genetically manipulated, as described herein. In the present context, a "transgenic animal" does not encompass animals produced by classical crossbreeding or in vitro fertilization, but rather denotes animals in which one or more cells receive a recombinant DNA molecule. Transgenic animals can be either heterozygous or homozygous with respect to the transgene. Methods for producing transgenic animals are well known in the art (see, for example, U.S. Pat. Nos. 5,721,367, 5,695,977, 5650,298, and 5614,396).

The chimeric polypeptides described herein can be used to generate additional reagents, such as antibodies. Invention antibodies are useful in the various treatment methods set forth herein. For example, the antibody produced in an immunized subject can protect the subject against virus infection or, alternatively, be transferred to a recipient subject, thereby passively protecting the second subject against infection. Antibodies that bind to an epitope exposed upon complex formation between a virus coat polypeptide sequence and a receptor polypeptide sequence also can be generated. In addition, invention antibodies are useful in diagnostic methods, purification methods, and in screening methods (e.g., identifying cryptic epitopes, co-receptors, etc.), as disclosed herein.

Thus, in accordance with the present invention, antibodies that bind to chimeric polypeptides, including antibodies specific for cryptic epitopes exposed upon complex formation as set forth herein, are provided. In one embodiment, the antibody neutralizes multiple viral isolates and viruses from different geographic clades (termed "broadly neutralizing") in vitro. In another embodiment, the antibody inhibits, prevents, or blocks virus infection in vitro or in vivo. In various aspects of these embodiments, the virus neutralized is an immunodeficiency virus, including the HIV-1 and HIV-2 immunodeficiency viruses set forth herein. Antibody comprising polyclonal antibodies, pooled monoclonal antibodies with different epotopic specificities, and distinct monoclonal antibody preparations, also are provided.

Antibodies to chimeric polypeptide are produced by administering a chimeric polypeptide to an animal. The antibodies can be produced, isolated, and purified using methods well-known in the art. Thus, in another embodiment, the invention provides methods for producing an antibody to a chimeric polypeptide. A method of the invention includes administering a chimeric polypeptide to a subject and isolating the antibodies that bind to the chimeric polypeptide. In one embodiment, the antibody produced binds to a cryptic epitope exposed upon the binding between a virus coat polypeptide sequence and a receptor polypeptide sequence.

Preferably, antibodies bind to cryptic epitopes exposed when the virus coat polypeptide sequence (e.g., envelope polypeptide sequence) and the receptor polypeptide sequence bind to each other. For example, the HIV envelope polypeptide sequence gp120 exposes a cryptic epitope upon binding to CD4 receptor polypeptide sequence, and antibodies to the exposed epitope can lead to broad neutralization of HIV. Such epitopes may be shared among different viral isolates and geographic clades accounting for broad-spectrum neutralizing activity of the antibodies directed to these epitopes.

Although not wishing to be bound by theory, it appears that in the absence of CD4 binding, the cryptic epitope is not exposed or is not antigenic. As used herein, the term "epitope" refers to an antigenic determinant on an antigen to which the paratope of an antibody binds. Epitopic determinants usually consist of chemically active surface groupings of molecules, such as amino acids or carbohydrate side chains, and usually have specific three-dimensional structural characteristics, as well as specific charge characteristics. As used herein, the term "cryptic" refers to a property or feature that requires a structural or conformational change for the feature or property to become apparent; in the absence of the change, the feature or property is "hidden." Cryptic epitopes may be present on either virus coat proteins or receptor polypeptide sequences.

The term "antibody" includes intact molecules, as well as fragments thereof, such as Fab, F(ab')$_2$, and Fv, which are capable of binding to an epitopic determinant present in a chimeric polypeptide described herein. Other antibody fragments are included, so long as the fragment retains the ability to selectively bind with its antigen. Antibody fragments (e.g., Fab, F(ab')$_2$, and Fv) of the present invention can be prepared by proteolytic hydrolysis of the antibody, for example, by pepsin digestion of whole antibodies. Antibodies which bind to disclosed chimeric polypeptides can be prepared using intact chimeric polypeptide or fragments thereof as the immunizing antigen. In the case of chimeric polypeptide fragments, it is preferred that the virus coat polypeptide sequence and the receptor polypeptide sequence maintain the ability to bind each other so that any cryptic epitopes present will be exposed. The chimeric polypeptide used to immunize an animal is derived from translated polynucleotide or is chemically synthesized and, if desired, can be conjugated to a carrier. Such commonly used carriers chemically coupled to the immunizing peptide include, for example, keyhole limpet hemocyanin (KLH), thyroglobulin, bovine serum albumin (BSA), and tetanus toxoid.

Monoclonal antibodies are made by methods well-known to those skilled in the art (Kohler et al., *Nature*, 256:495 (1975); and Harlow et al., *Antibodies: A Laboratory Manual*, p. 726, eds. Cold Spring Harbor Pub. (1988), which are incorporated herein by reference). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques, which include, for example, affinity chromatography with Protein-A Sepharose, size-exclusion chromatography, and ion-exchange chromatography (see, e.g., Coligan et al., "Production of Polyclonal Antisera in Rabbits, Rats, Mice and Hamsters," In: *Current Protocols in Immunology*, §§ 2.7.1-2.7.12 and §§ 2.9.1-2.9.3; and Barnes et al., "Purification of Immunoglobulin G (IgG)," In: *Methods in Molecular Biology*, Vol. 10, pp. 79-104, Humana Press (1992)). The preparation of polyclonal antibodies is well-known to those skilled in the art (see, e.g., Green et al., "Production of Polyclonal Antisera," In: *Immunochemical Protocols*, pp. 1-5, Manson, ed., Humana Press (1992); Harlow et al. (1988), supra; and Coligan et al. (1992), supra §2.4.1, which are incorporated herein by reference).

For therapeutic purposes, antibodies to a chimeric polypeptide produced in one species can be humanized so that the antibody does not induce an immune response when administered to the host, for example, for passive immunization. Generally, humanized antibodies are produced by replacing a non-human constant region with a human constant region. Such antibody humanization methods are known in the art and are particularly useful in the methods of the invention (Morrsion et al., *Proc. Natl. Acad. Sci. USA*, 81:685 1 (1984); Takeda et al., *Nature*, 314:452 (1985); Singer et al., *J. Immunol.*, 150:2844 (1993)).

Antibodies that bind a chimeric polypeptide, particularly, antibodies that bind a cryptic epitope, can neutralize the virus in vitro or in vivo (i.e., in a subject). Such antibodies can therefore prevent or inhibit virus infection in vitro or in vivo, and may ameliorate some or all of the symptoms associated with the infection. Such antibodies can be produced in one subject and then introduced into another, i.e., for passive immunotherapy. Alternatively, antibodies that bind chimeric polypeptides, when produced in a subject, can protect that subject from infection or ameliorate some or all of the symptoms associated with the infection.

Thus, in accordance with the present invention, there are provided methods for inhibiting, preventing, and ameliorating a viral infection in a subject. In one embodiment, a method of the invention includes administering an effective amount of an antibody that binds to a chimeric polypeptide to a subject, thereby preventing or inhibiting virus infection in the subject. In another embodiment, a method of the invention includes administering an effective amount of a chimeric polypeptide to a subject, thereby producing an immune response sufficient for preventing or inhibiting virus infection in the subject. In yet another embodiment, a method of the invention includes administering to a subject an effective amount of a polynucleotide encoding an invention chimeric polypeptide. In various aspects, the chimeric polypeptide contains an immunodeficiency virus envelope polypeptide, as disclosed herein.

In the methods for inhibiting, preventing, and ameliorating a viral infection in a subject in which a chimeric polypeptide or a polynucleotide encoding a chimeric polypeptide are administered, an immune response also can be produced. The immune response will likely be humoral in nature, although a administering a polynucleotide encoding a chimeric polypeptide may induce a CTL response. It is also understood that the methods of the invention can also be used in combination with other viral therapies, as appropriate.

The "effective amount" will be sufficient to inhibit, prevent, or ameliorate a viral infection in a subject, or will be sufficient to produce an immune response in a subject. Thus, an effective amount of chimeric polypeptide can be that which elicits an immune response to the polypeptide or a virus upon which the coat protein is based. An effective amount administered to a subject already infected with the virus can also be that which decreases viral load, or increases the number of CD4 + cells. An effective amount can be that which inhibits transmission of the virus from an infected subject to another (uninfected or infected).

In the methods of the invention in which a polynucleotide sequence encoding a chimeric polypeptide is administered to a subject, a CTL response to the chimeric polypeptide can be produced against a virus that contains the corresponding coat polypeptide sequence.

As the chimeric polypeptides, polynucleotides, and antibodies of the present invention will be administered to subjects, including humans, the present invention also provides pharmaceutical formulations comprising the disclosed chimeric polypeptides, polynucleotides, and antibodies. The compositions administered to a subject will therefore be in a "pharmaceutically acceptable" or "physiologically acceptable" formulation.

As used herein, the terms "pharmaceutically acceptable" and "physiologically acceptable" refer to carriers, diluents, excipients, and the like that can be administered to a subject, preferably without excessive adverse side effects (e.g., nausea, headaches, etc.). Such preparations for administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions, or suspensions, including saline and buffered media. Vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present, such as, for example, antimicrobial, anti-oxidants, chelating agents, and inert gases and the like. Various pharmaceutical formulations appropriate for administration to a subject known in the art are applicable in the methods of the invention (e.g., *Remington's Pharmaceutical Sciences*, 18$^{th}$ ed., Mack Publishing Co., Easton, Pa. (1990); and *The Merck Index*, 12$^{th}$ ed., Merck Publishing Group, Whitehouse, N.J. (1996)).

Controlling the duration of action or controlled delivery of an administered composition can be achieved by incorporating the composition into particles or a polymeric substance, such as polyesters, polyamine acids, hydrogel, polyvinyl pyrrolidone, ethylene-vinylacetate, methylcellulose, carboxymethylcellulose, protamine sulfate or lactide/glycolide copolymers, polylactide/glycolide copolymers, or ethylenevinylacetate copolymers. The rate of release of the composition may be controlled by altering the concentration or composition of such macromolecules. Colloidal dispersion systems include macromolecule complexes, nano-capsules, microspheres, beads, and lipid-based systems, including oil-in-water emulsions, micelles, mixed micelles, and liposomes.

The compositions administered by a method of the present invention can be administered parenterally by injection, by gradual perfusion over time, or by bolus administration (for example, in the case of passive protection against HIV infection resulting from a needlestick injury) or by a microfabricated implantable device. The composition can be administered via inhalation, intravenously, intraperitoneally, intramuscularly, subcutaneously, intracavity (e.g., vaginal or anal), transdermally, topically, or intravascularly. The compositions can be administered in multiple doses. The doses or "effective amount" needed for treating, inhibiting, or preventing viral infection or transmission, or for inducing an immune response, preferably will be sufficient to ameliorate some or all of the symptoms of the infection, although preventing progression or worsening of the infection also is a satisfactory outcome for many viral infections, including HIV. An effective amount can readily be determined by those skilled in the art (see, for example, Ansel et al., *Pharmaceutical Drug Delivery Systems*, 5$^{th}$ ed. (Lea and Febiger (1990), Gennaro ed.)).

The chimeric polypeptides, polynucleotides, and antibodies of the invention are also useful for diagnostic purposes. For example, a chimeric polypeptide having a virus coat polypeptide sequence derived from a virus that utilizes co-receptor for infection can be used to identify subjects that express co-receptors having decreased binding affinity for the chimeric polypeptide. Subjects which have a decreased binding affinity will likely have a decreased risk of infection by the virus. Alternatively, subjects expressing co-receptors having an increased binding affinity for the chimeric polypeptide will likely be at increased risk of virus infection. In this way, subjects having decreased or increased risk to virus infection can be identified. For example, subjects expressing a CCR5 or CXCR4 co-receptor having increased or decreased affinity for a chimeric polypeptide comprised of HIV gp120-CD4 will be at increased or decreased risk of HIV infection, respectively. Accordingly, such methods also are useful for assessing prognosis; subjects expressing a high affinity binding co-receptor likely having a poorer prognosis.

In the case of the chimeric polypeptides disclosed herein that have a virus coat polypeptide sequence of a virus that utilizes a co-receptor, such chimeric polypeptides are useful for identifying agents that modulate binding of the virus to the co-receptor. Such chimeric polypeptides also are useful for identifying agents that modulate the intramolecular interaction/binding of the virus coat polypeptide sequence to the receptor sequence within the chimeric polypeptide. Thus, described chimeric polypeptides that contain coat polypeptide of virus that may not utilize co-receptor can be used to identify agents that modulate binding of the coat sequence to the receptor sequence within the chimeric molecule.

Thus, in accordance with the present invention, there are provided methods for identifying an agent that modulates binding between a virus and a virus co-receptor, and methods for identifying an agent that modulates binding between a virus and a virus receptor.

In one embodiment, a method of the invention includes contacting a chimeric polypeptide with a co-receptor polypeptide under conditions allowing the chimeric polypeptide and the co-receptor polypeptide to bind, in the presence and absence of a test agent, and detecting binding in the presence and absence of the test agent. In another embodiment, a method of the invention includes contacting a chimeric polypeptide that forms an intramolecular complex with a test agent, and detecting binding between the virus coat polypeptide sequence and the receptor polypeptide sequence within the chimera. A decreased amount of binding in the presence of the test agent thereby identifies an agent that inhibits interaction/binding between the virus and the virus co-receptor or receptor. Increased binding in the presence of the test agent thereby identifies an agent that stimulates interaction/binding between the virus and the virus co-receptor or receptor.

The contacting can occur in solution, solid phase, on intact cells, or in an organism, such as a non-human primate. In various embodiments, the virus is an immunodeficiency virus, such as HIV and the co-receptor is a chemokine, such as CCR5 or CXCR4. The binding of viruses that utilize co-receptors for cell penetration is a critical step for subsequent infection, viral proliferation, and the ultimate pathological symptoms resulting therefrom. Thus, in another embodiment, methods for identifying agents that inhibit virus cell penetration, infection, and proliferation, as well as agents that ameliorate the symptoms associated with the virus infection, are provided. In a method of the present invention for identifying such agents, the test agent can be added after contacting the chimeric polypeptide with the co-receptor polypeptide or, alternatively, before contacting the chimeric polypeptide with the co-receptor polypeptide.

Candidate agents include antibodies, antivirals, a co-receptor polypeptide sequence (e.g., from CCR5 or CXCR4), peptidomimetics or active fragments thereof. Candidate agents also encompass numerous chemical classes, including organic molecules, like small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl, or carboxyl group, preferably at least two of the functional chemical groups. The candidate agents often comprise cyclical carbon or heterocyclic structures, and/or aromatic or polyaromatic structures substituted with one or more of the above functional groups. Candidate agents are also found among biomolecules, including, but not limited to, peptides, saccharides, fatty acids steroids, purines, pyrimidines, derivatives, structural analogs, or combinations thereof.

Candidate agents are obtained from a wide variety of sources, including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant, and animal extracts are available or readily produced. Additionally, natural or synthetically produced libraries and compounds are readily modified through conventional chemical, physical, and biochemical means, and may be used to produce combinatorial libraries. Known pharmacological agents may be subjected to directed or random chemical modifications, such as acylation, alkylation, esterification, amidification, etc., to produce structural analogs. Where the method detects binding, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the assay. These include reagents, like salts, neutral proteins, e.g. albumin, detergents, etc., that are used to facilitate optimal protein-protein binding and/or reduce non-specific or background interactions. Reagents that improve the efficiency of the assay, such as protease inhibitors, nuclease inhibitors, anti-microbial agents, etc., may be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically, between 0.1 and 1 hour will be sufficient.

In various embodiments, the virus is an immunodeficiency virus, as described herein, such as HIV, HTLV, SIV, FeLV, FPV, or herpes virus. In additional embodiments, the co-receptor is a CCR5, CXCR4, CCR-2b, CCR3, CCR8, V28/CX3CR1, US28 (herpes virus encoded chemokine like receptor), STRL33/BOB/TYMSTR, GPR15/Bonzo, or GPR1 polypeptide sequence.

An agent identified by a method of the invention described herein can be further tested for its ability to inhibit virus binding or infection of a cell in vitro or in vivo. Thus, in accordance with the present invention, there are provided methods for identifying an agent that inhibits virus infection of a cell. A method of the invention includes contacting a cell susceptible to virus infection with an infectious virus particle in the presence and absence of a test agent, and determining whether the test agent inhibits virus binding or infection of the cell, thereby identifying an agent that inhibits virus infection. In various embodiments, the test agent is added before or after contacting the cell with the infectious virus particle. The method also can be performed in any suitable animal, such as a non-human primate.

The chimeric polypeptides described herein are also useful for identifying novel co-receptors or characterizing proteins as co-receptors. In this way, viral infection and subsequent pathogenesis for any virus can be better understood, thereby enabling improved treatment of the infection. For example, one method for identifying a novel co-receptor or characterizing co-receptor function is the two-hybrid system, which can detect protein-protein interactions through the activation of a reporter whose expression is induced by interacting polypeptides. Thus, an appropriate chimeric polypeptide can be used as a bait sequence in a yeast or mammalian two-hybrid system to screen a library for the purpose of identifying interacting proteins, including novel co-receptors. Well established biochemical methods of detecting protein-protein interactions (e.g., column chromatography, gradient centrifugation, co-immunoprecipitation analysis, etc.) also are applicable in identifying co-receptors or in characterizing proteins as having potential co-receptor function.

The chimeric polypeptides that bind co-receptors also are useful for identifying a co-receptor binding site. For example, by producing co-receptor polypeptide fragments and contacting the fragments with an appropriate chimeric polypeptide. The contacting can be done in solution, (e.g., co-precipitation), solid phase (e.g., affinity column), or on an intact cell (e.g., contacting co-receptor fragments on a cell surface and detecting whether the co-receptor fragment inhibits chimeric polypeptide binding to the cell). A co-receptor binding site, once identified, can be used as an antiviral agent to treat infection, for example.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting. Other features and advantages of the invention will be apparent from the following detailed description, and from the claims. The invention is further described in the following examples, which do not limit the scope of the invention(s) described in the claims.

EXAMPLE I

This Example describes the construction of polynucleotides encoding a single chain gp120-CD4 chimeric polypeptide FLSC, TsSC, FLSC-R/T and RLSC-R/T CD4M9. The strategy for building a single chain complex is based on the placement of a 20 to 30 amino acid linker sequence between the C terminus of gp120 and the N terminus of CD4. Analyses of the crystal structure of modified gp120 bound to soluble CD4 and 17b Fab (Dwong, P. D. et al., Nature, 393:648-59 (1998)) using Swiss PDB Viewer suggested that a chimeric molecule should be capable of intramolecular interactions leading to formation of a gp120-CD4 complex. A single chain nucleic acid encoding a gp120-CD4 chimeric polypeptide (SEQ ID NO: 1) was constructed by arranging the respective coding sequences in the following order: (1) at the 5' end, a synthetic, codon encoding gp120 of the macrophage-tropic HIVs, BaL; (2) a sequence encoding a 20 amino acid linker consisting of glycines, alanine, and serines; (3) sequences for soluble CD4 domains 1 and 2 (D1D2); and (4) at the 3' end, sequences encoding a short polypeptide derived from the c-myc oncogene for FLSC. The FLSC-R/T nucleotide sequence (SEQ ID NO: 3) encodes for a protein having a mutation at the c-terminal end of gp120 wherein the arginine is replaced with a threonine (SEQ ID NO: 4). FLSC-R/T CD4M9 (SEQ ID NO: 5) includes further changes in the nucleotide sequence of a chimera polypeptide (SEQ ID NO: 6) of the present invention wherein the CD4 D1D2 region is replaced with a sequence coding for CD4M9 that encodes for a peptide that mimics the functional activity of the CD4 D1D2 region. The codon optimized gp120 sequence was used as it permits high-level expression in a rev-independent manner (Haas, J., et al., Curr. Biol., 6:3 15-24 (1996)). The human CD4 sequence used was derived from T4-pMV7 (Maddon, P. J., et al., Cell, 47:333-48 (1986); NIH AIDS Reagent Repository, Bethesda, Md.). The myc polypeptide sequence allows convenient analyses, purification, and other manipulation of the chimeric polypeptide.

Complete polynucleotides comprising these different sequences were generated by PCR and inserted into pEF6 (Invitrogen) using the strong elongation factor promoter (EF 1) to drive expression. Restriction enzyme sites were introduced into this construct (designated pEF6-SCBa1) to permit convenient exchange with other envelope genes of other immunodeficiency viruses.

Briefly, FLSC molecule was constructed via PCR using the plasmids pMR1W1-9 and T4-pMV7 as templates. The gp120 forward primer was GGG-GGT-ACC-ATG-CCC-ATG-GGG-TCT-CTG-CAA-CCG-CTG-GCC (SEQ ID NO:7) and the reverse primer was GGG-TCC-GGA-GCC-CGA-GCC-ACC-GCC-ACC-AGA-GGA-TCC-ACG-CTT-CTC-GCG-CTG-CAC-CAC-GCG-GCG-CTT (SEQ ID NO:8). The CD4 forward primer was GGG-TCC-GGA-GGA-GGT-GGG-TCG-GGT-GGC-GGC-GCG-GCC-GCT-AAG-AAA-GTG-GTG-CTG-GGC-AAA-AAA-GGG-GAT (SEQ ID NO:9) and the reverse primer was GGG-GTT-TAA-ACT-TAT-TAC-AGA-TCC-TCT-TCT-GAG-ATG-AGT-TTT-GTT-CAG-CTA-GCA-CCA-CGA-TGT-CTA-TTT-TGA- ACT-C (SEQ ID NO: 10). The PCR product was subcloned into pEF6 (Invitrogen, Carlsbad, Calif.) using Kpn1 and Pme1 restriction sites.

To construct the pEF6-TcSC plasmid, the full-length gp120 expressing sequence in pEF6-FLSC was exchanged for a truncated version of the gp120 sequence (DC1DC5DV1V2). The truncated gp120 was generated using GGG-GGT-ACC-ATG-CCC-ATG-GGG-TCT-CTG-CAA-CCG-CTG-GCC-ACC-TTG-TAC-CTG-CTG-GGG-ATG-CTG-GTC-GCT-TCC-TGC-CTC-GGA-AAG-AAC-GTG-ACC-GAG-AAC-TTC-AAC -ATG-TCC (SEQ ID NO: 15) as a forward primer and GGG-GGA-TCC-GAT-CTT-CAC-CAC-CTT-GAT-CTT-GTA-CAG-CTC (SEQ ID NO: 16) as a reverse primer. The V1 and V2 regions were deleted using CTG-TGC-GTG-ACC-CTG-GGC-GCG-GCC-GAG-ATG-AAG-AAC-TGC-AGC-TTC-AAC-ATC-GGC-GCG-GGC-CGC-CTG-ATC-AGC-TGC (SEQ ID NO:17) as a forward primer and GCA-GCT-GAT-CAG-GCG-GCC-CGC-GCC-GAT-GTT-GAA-GCT-GCA-GTT-CTT-CAT-CTC-GCC-CGC-GCC-CAG-GGT-CAC-GCA-CAG (SEQ ID NO: 18) as a reverse primer.

The CD4M9 sequence (SEQ ID NO: 19) used to clone into FLSC R/T CD4M9 was generated by using the 5' to 3' primers GCG-GCC-GCT-TGC-AAC-CTG-GCC-CGC-TGC-CAG-CTG-CGC-TGC-AAG-AGC-CTG-GGC-CTG-CTG-GGC-AAG-TGC-GCC-GGC-AGC-TTC-TGC-GCC-TGC-GGC-CCC-TAA-GAA-TTC (SEQ ID NO: 21) as a forward primer and GAA-TTC-TTA-GGG-GCC-GCA-GGC-GCA-GAA-GCT-GCC-GGC-GCA-CTT-GCC-CAG-CAG-GCC-CAG-GCT-CTT-GCA-GCG-CAG-CTG-GCA-GCG-GGC-CAG-GTT-GCA-AGC-GGC-CGC (SEQ ID NO: 22) as a reverse primer and annealing together. Fragments were cut with Not1 & BamH1, then subcloned into pEF6-FLSC R/T that had been prepared by cutting with Not1 & BamH1 and gel purified to remove the relieved hD1D2 from the FLSC R/T sequence. Clones were confirmed by sequencing.

The recombinant constructs are shown in FIG. 1. The chimeric recombinant which contained the BaL gp120 (SEQ ID NO: 24) sequence with a spacer region (SEQ ID NO: 11) and CD4D1D2 region (SEQ ID NO: 26) was designated full-length single chain (FLSC). A second construct was designed to produce complexes more closely resembling the molecules used to solve the gp120 crystal structure. This construct was designated truncated single chain (TcSC) and constructed as with FLSC except that a sequence encoding ΔC1ΔC5ΔV1V2 gp120 was used in place of the full length coding sequence (SEQ ID NO: 28). Also shown are constructs designated FLSC-R/T wherein the BaL gp120 is mutated at amino acid 506 (SEQ ID NO: 30) and FLSC-R/T CD4M9 comprising sequences SEQ ID NO: 30 and 20. The amino acid sequence of the spacer region shown in this example is GSSGGGSGSGGGGSGGGAAA (SEQ ID NO: 11)

EXAMPLE II

This Example describes the transfection of cells with the polynucleotide encoding the gp120-CD4 chimeric polypeptide and the characterization of the expressed soluble polypeptide. Recombinant pEF6-FLSC or pEF6-TcSC was transfected into 293 cells using Fugene, according to the manufacturer's protocol (Boehringer-Manheim). Stable transfectants were obtained by selection with 5 ug/ml blasticidin. A stable cell line (293-SC) was cultured under different conditions, and the production of chimeric polypeptide evaluated by immunoblot analysis using a mixture of anti-gp120 monoclonal antibodies (Y. H. Abacioglu et al., AIDS Res. Hum. Retroviruses, 10:371-81 (1994)) or anti- human CD4 polyclonal sera (T4-4) (K. C. Deen et al., *Nature*, 331:824 (1998); R. L. Willey et al., *J. Viral.*, 66:226-34 (1992); NIH AIDS Reagent Repository).

Figure 2:
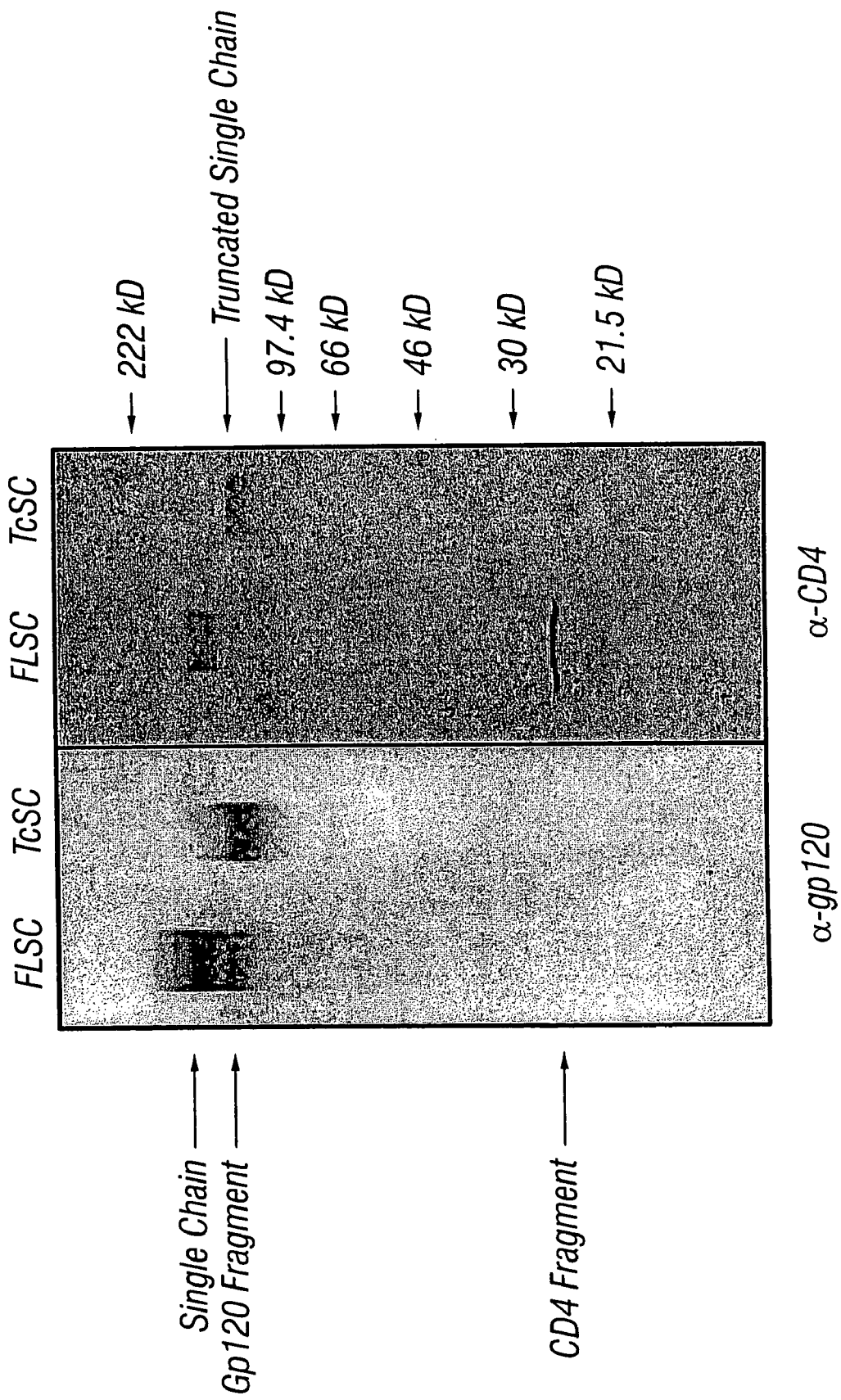
FIG. 2 is a Western blot analysis of cell culture supernatant containing FLSC and TcSC soluble chimeric polypeptide expressed by 293-SC cells. Immunoblotting was performed with gp120 (lanes 1 to 4) and CD4 (lanes 5 to 8) and the arrows indicate, in order of decreasing gel mobility, gp120-CD4 single chain (single chain), cleaved gp120 (gp120 fragment) and cleaved CD4 (CD4 fragment).

Briefly, cell culture supernatants containing the chimeric polypeptide were collected and boiled in SDS-PAGE loading buffer (75 mM Tris, 2% SDS, 10% glycerol, 0.001% bromphenol blue, pH 8.3). The samples were then electrophoresed in a 4-20% SDS-polyacrylamide gradient gel. The gel-fractionated proteins were then transferred to a nitrocellulose membrane. Non-specific binding sites on the membrane were then blocked for 30 minutes with 2% non-fat dry milk in tris-buffered saline, pH 7. The membrane was then probed with either anti-CD4 polyclonal rabbit sera (T4-4; NIH AIDS Reagent Repository, Bethesda, Md.) or a mixture of murine monoclonal antibody against HIV gp120. As shown in FIG. 2, the transfected cells expressed a soluble protein of the expected size (150 kD). This polypeptide was reactive with both anti-gp120 and anti-CD4 antibodies and, thus, represented intact chimeric polypeptide.

In other studies, reactivity with anti-myc antibody was detected further confirming the identity of the 150 kD species as the chimeric polypeptide. In addition to this polypeptide, bands matching the expected sizes for gp120 and CD4 D1D2/myc tag were observed indicating that a portion of the chimeric polypeptide had been cleaved at the spacer. Addition of a biologically compatible protease inhibitor (Pefabloc; Boerhinger-Mannhiem) yielded essentially uncleaved chimeric polypeptide molecules. This suggests that cleavage of gp120-CD4 occurs by a serine protease. The amount of gp120-CD4 chimeric polypeptide produced by the 293-SC cell line was determined using an anti-gp120 capture ELISA with sheep anti-gp120 antibody D7324 (International Enzymes), a sheep polyclonal IgG against a highly conserved epitope in the gp120 C5 region (J. P. Moore, *AIDS*, 4:297-305 (1990); J. P. Moore et ul., *J. Virol.*, 67:863-75 (1992); J. P. Moore et al., *AIDS*, 4:307-15 (1990)), and a gp120 standard curve.

Briefly, 2 ug/ml of D7324 in phosphate-buffered saline was absorbed onto a plastic plate. Non-specific binding sites were blocked with 2% non-fat dry milk in buffered saline. Saturating concentrations of cell culture supernatant from the 293-SC line were then added to the plate. Captured chimeric polypeptides were detected using inactivated human sera from HIV-infected patients and anti-human IgG conjugated to horse-radish peroxidase. The 293-SC cell line is estimated to secrete approximately 3 ug/ml of gp120-CD4 chimeric polypeptide. The 293-SC cell line has been adapted to grow in serum-free conditions. Because the immunoblotting studies indicated that there was some cleavage of the gp120-CD4 chimeric polypeptide a sample of purified single chain was crosslinked and the crosslinked sample analyzed to determine if the gp120 and CD4 molecules remained associated. Briefly, single chain gp120-CD4 from supernatants produced by 293-SC cell line was purified using an immunoaffinity column. The column was constructed by linking anti-gp120 human monoclonal antibody A32 to CNBr-activated sepharose 4B (Amersham-Pharmacia Biotech, Piscataway, N.J.). A32 is specific for a highly discontinuous epitope on gp120, and preferentially recognizes envelope bound to CD4. Bound gp120-CD4 was eluted with 0.1 M acetic acid pH 2.5, lyophilized, and dialyzed against PBS. Protein concentration was determined by a BCA assay (Bio-Rad, Hercules, Calif.) using the manufacturer's protocol. A 20 ul aliquot of purified gp 120-CD4 was then crosslinked with 1 mM solution of the homo-bifunctional crosslinker, BS3, and electrophoresed along with uncrosslinked gp 120-CD4 on a 4-20% polyacrylamide gel. The fractionated proteins were transferred to nitrocellulose, immunoblotted with a mixture of anti-gp120 monoclonal antibodies followed by an alkaline-phosphatase labeled anti-mouse IgG, and visualized with a commercial mixture of BCIP/NBT (KPL).

Figure 3:
FIG. 3 is an analysis of gp120-CD4 expressed by 293-SC cells; uncrosslinked gp120- CD4 is in lane 1 and the crosslinked gp120-CD4 is in lane 2.
Figure 4:
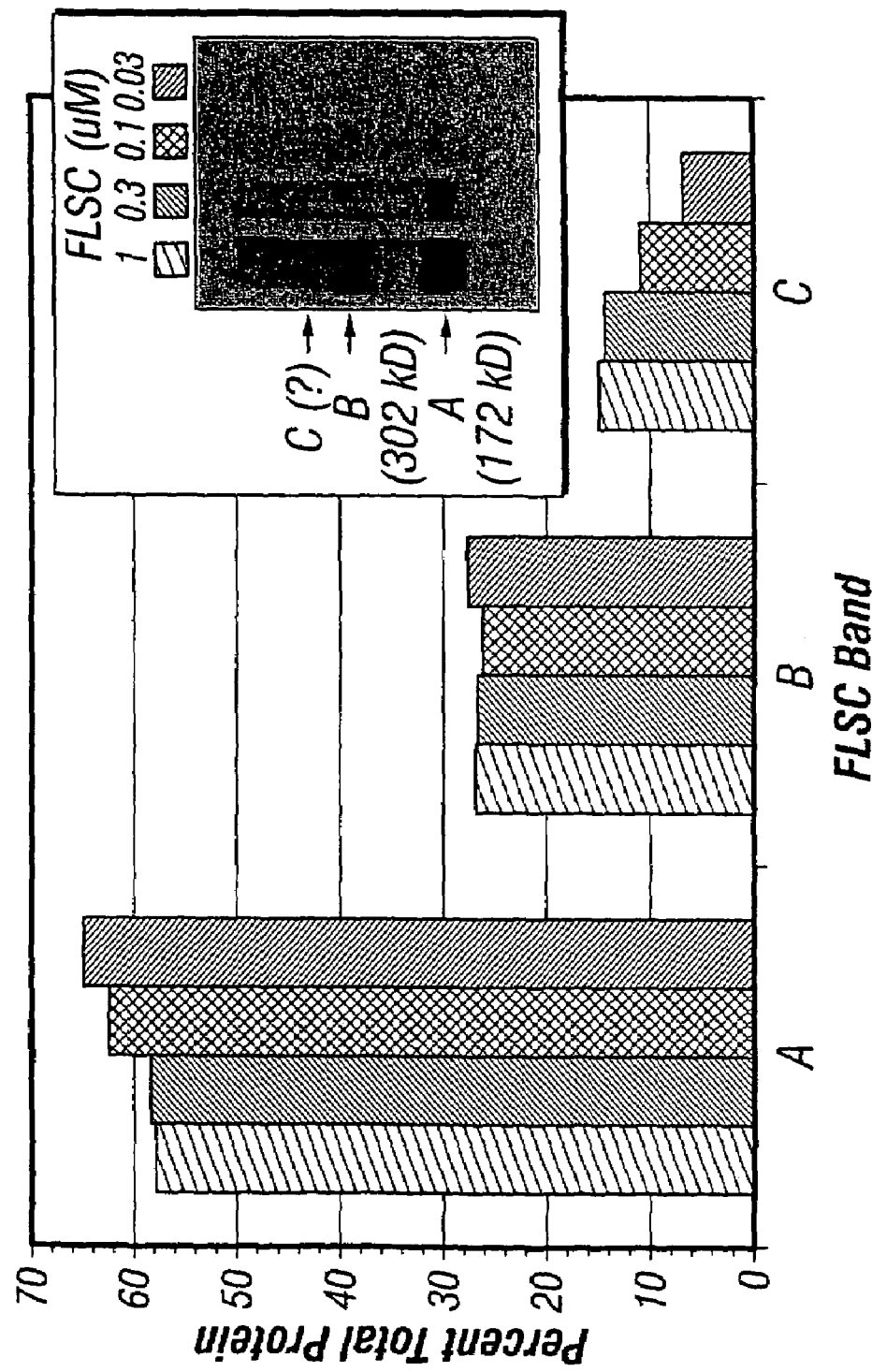
FIG. 4 is an immunoblot analysis of FLSC after crosslinking. The relative percent (%) total protein for each of the different FLSC concentrations (1-0.03 uM) are shown in the bar graph: (A), 45% 172 kD; (B), 25% 302 kD; and (C), 10% higher order oligomer.

FIG. 3 shows the results of these studies; uncrosslinked gp120-CD4 is in lane 1, and the crosslinked gp120-CD4 is in lane 2. Lane 1 shows that the immunoaffinity column purifies both cleaved and uncleaved single-chain gp120-CD4. Crosslinking, as shown in lane 2, generates two broad bands at 150 kDa and 300 kDa, a pattern suggesting that the single chain gp120-CD4 in solution exists as an associated 150 kDa molecule. The gp120 and CD4 subunits remain associated, even after the cleavage event. The 300 kDa band indicates that a portion of gp120-CD4 is dimeric in solution and may represent single chain molecules that associate through intermolecular interactions between the envelope and CD4 domains on separate molecules. The apparent cleavage of the single-chain molecules into gp120 and CD4 moieties under certain conditions (FIG. 2) might be a concern for DNA vaccines, since such processing could potentially occur in vivo. However, these studies show that despite cleavage the single-chain molecules remained associated as gp120-CD4 complexes (FIG. 3). To examine the structural properties of the native FLSC in greater detail, different concentrations (1 uM-0.03 uM) of the same protein preparation examined above were covalently crosslinked in PBS in order to fix any multimeric structures existing in solution. Crosslinked material was then analyzed by immunoblot assay with anti-CD4 antibody. As shown in FIG. 4, a major protein band (inset; band A) of 172 kD was consistently visible along with two minor bands of higher molecular weight. One of the minor bands (inset; band B) had an apparent size of approximately 302 kD, while the other (inset; band C) failed to migrate far enough into the gel to allow an accurate assessment of size by SDS-PAGE. The appearance and proportions of the different protein bands were not dependent on the FLSC concentration prior to crosslinking. Thus, densitometric analyses indicated that bands A, B and C consistently represented approximately 65%, 25% and 10% of the total protein, respectively.

In comparison to the FLSC, the chromatographic profile of the crosslinked TcSC was more complex. Under non-denaturing conditions TcSC eluted as a broad series of peaks ranging from 166 kD to 353 kD. Such a profile indicated that the shorter TcSC polypeptide forms multiple higher order structures upon expression and/or purification. This behavior indicates that the TcSC exists primarily as variably sized chains of polypeptides joined by interactions between gp 120 sequences and CD4 sequences in separate molecules. Since the TcSC was created by deleting 20 C-terminal amino acids from gp120, the distance between the CD4 core structure and the CD4bd of gp120 was shortened which may hinder the ability of the TcSC to achieve an intramolecular gp120-CD4 interaction thereby favoring formation of interchain complexes. Nevertheless, TcSC also exhibited the antigenic and functional features of a gp120-CD4 complex. It is possible that because of intermolecular interactions involving multiple TcSC molecules, a smaller proportion of the total protein expressed a co-receptor binding site capable of interacting with surface co-receptors. Alternatively, deletion of the VI/V2 regions in the TcSC may decrease the relative affinity of the BaL envelope for CCR5. Further modification of the TcSC to elongate the linker between the gp120 and CD4 moieties might allow formation of a higher proportion of intrachain complexes. Whether the multimeric nature of the TcSC puts this molecule at a disadvantage to FLSC remains an open question, since studies with other multimeric molecules suggest they are more potent immunogens than their monomeric counterparts (A. L. DeVico et al., *AIDS Rev.*, I:4-14 (1999); S. A. Jeffs et al., *J. Gen Virol*, 77:1403-1410 (1996); R. A. LaCasse et al., *Science*, 283:357-62 (1999)).

EXAMPLE III

This Example describes data demonstrating the binding of gp120-CD4 chimeric polypeptide to several different antibodies reactive with gp120 and CD4. The binding of gp120 to CD4 causes conformational changes in the molecule leading to the exposure of the co-receptor-binding domain. Therefore, antibodies directed against epitopes in this domain should react strongly with properly folded single-chain molecules. In order to determine exposed epitopes in chimeric molecules, antigenic properties of FLSC and TcSC molecules were compared. Purified FLSC and TcSC were subjected to immunochemical analyses by antigen capture ELISA. In brief, BaLgp120, gp120-rsCD4 complexes or single chain chimeric molecules were captured using a purified polyclonal sheep antibody (International Enzymes, Fallbrook, Calif.) raised against a peptide derived from the C-terminal 15 amino acids of gp120, D7324 (J. P. Moore et al., *AIDS Res. Hum. Retroviruses*, 4:369-79 (198X)), adsorbed to the matrix. The D7324 was diluted in PBS to 2 ug/ml and adsorbed to 96-well plates (Maxisorb plates, VWR Scientific, St. Louis, Mo.) by incubating overnight at room temperature. Plates were treated BLOTTO (5% non-fat dried milk in tris-buffered saline) in order to prevent nonspecific binding to the wells. After washing the plates with TBS samples were diluted in BLOTTO and 200 ul aliquots incubated in duplicate D7324-coated wells for 1 hour at room temperature. Bound antigen was detected using a pool of inactivated HIV-I+ sera diluted 1:1000 in BLOTTO followed by goat anti-human IgG labeled with horseradish peroxidase (KPL, Gaithersburg, Md.).

Detection was also accomplished using monoclonal antibodies (MAbs A32, 17b and 48d) previously shown to preferentially bind gp120 after engagement of CD4 (M. Thali et al., *J. Virol.*, 67:3978-86 (1993)), followed by the appropriate-labeled second antibody. Two of the antibodies, 17b and 48d, bind within the co-receptor attachment site that is induced by CD4 binding (N. Sullivan et al., *J. Virol.*, 72:4694-703 (1998); A. Trkola et al, *Nature*, 384: 184-6 (1996); L. Wu et al., *Nature*, 384: 179-183 (1996)). Antibody C 11, which recognizes a conserved epitope in the C1-C5 region of free gp120, was also tested. Antibodies were diluted in BLOTTO and incubated for 1 hour at room temperature. Plate were washed three times with TBS between each incubation step. The amounts of gp120 sequences present in samples were determined based on a standard curve generated with commercial recombinant HIV IIIB gp120 (Bartels, Issaquah, Wash.). In comparative studies involving BaLgp120-rsCD4 complexes, D7324-coated plates were treated with saturating concentrations of gp120. After washing the wells, an excess concentration of rsCD4 (1 ug/ml) was then added to the wells and incubated for 1 hour to form the complexes. In order to evaluate the TcSC antigen which lacks the D7324 epitope, an alternate ELISA format using anti-CD4 MAb 45 (Bartels, Issaquah, Wash.) for capture was developed. The antibody was adsorbed to plastic at 1 ug/ml and wells blocked with BLOTTO. Assays were then carried out as above using the indicated human sera or human monoclonal antibodies.

Figure 5A:
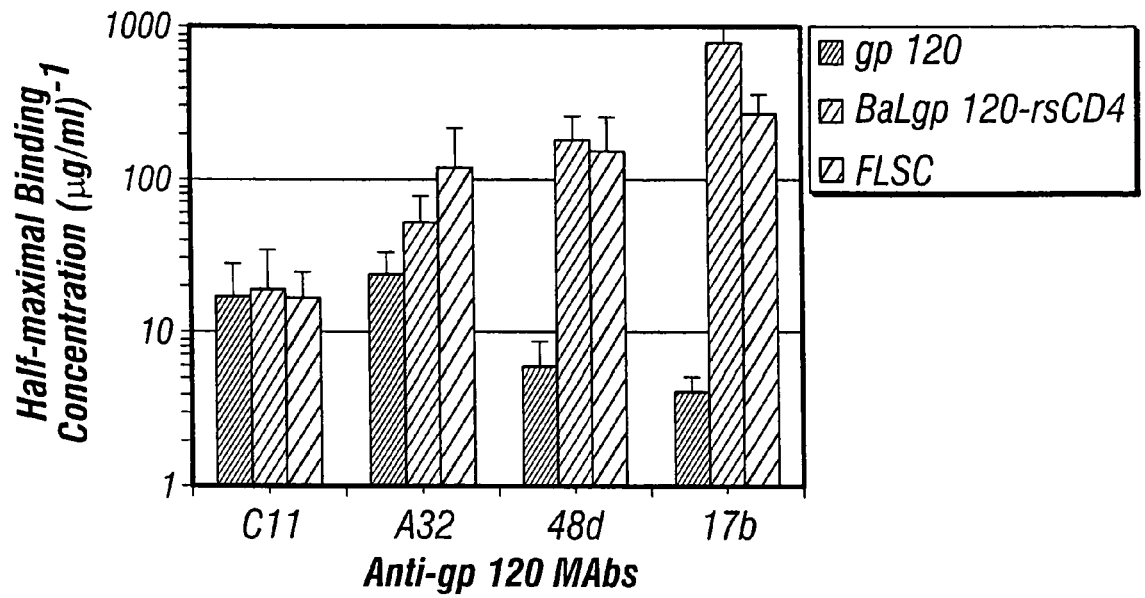
FIG. 5A-5C is a binding analysis of gp120-CD4 chimera. (A), Full length single chain (FLSC) incubated with anti-gp120 antibodies (17b, 48d, A32 and Cl 1) in comparison to crosslinked gp120/rsCD4 and uncomplexed gp120. 17b, 48d and A32 have preferential affinity for complexed gp120 (gp120). Bars are shown with standard error. (B), Reciprocal half-maximal binding concentration of human anti-gp120 monoclonal antibodies in FLSC and TcSC (ELISA). (C), Reciprocal half-maximal binding of monoclonal antibodies IgG1b12, F91 and 205-469, which react with the gp 120 CD4 binding domain.

As shown in FIG. 5A, all of the antibodies reacted strongly with the FLSC. However, the half-maximal binding concentrations of antibodies 17b, 48d, and A32 were consistently higher with FLSC versus gp120 alone, and equivalent to what was observed with soluble, non-covalent BaLgp120-rsCD4 complexes. The higher immunoreactivity of FLSC was specific to the antibodies directed against the CD4-induced epitopes, as there was no significant difference in the half-maximal binding concentrations of antibody C11 with FLSC versus free gp120.

Figure 5B:
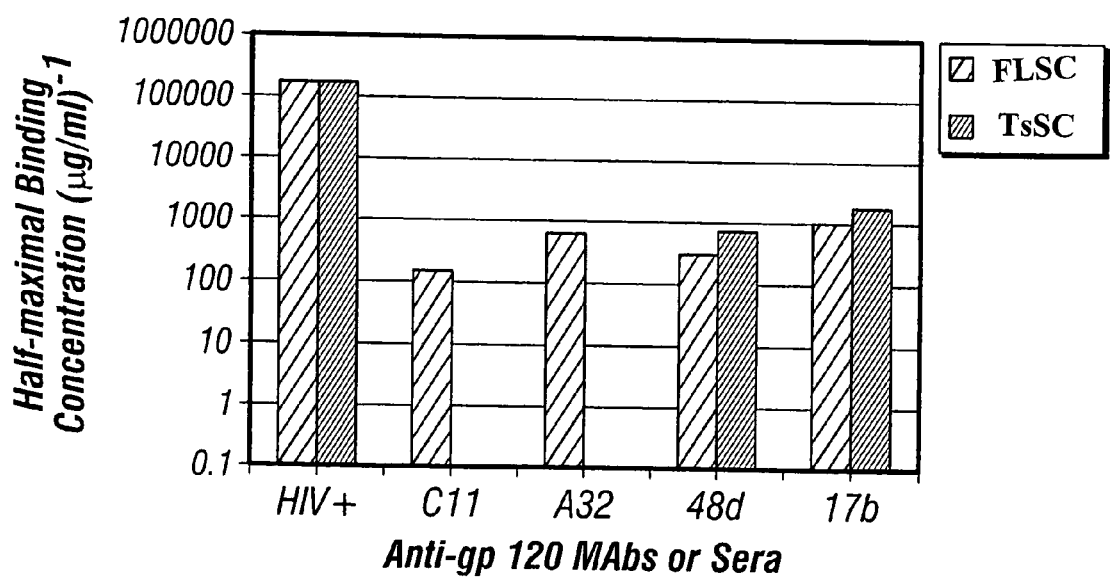

As shown in FIG. 5B, the level of 17b and 48d reactivity with TcSC was equivalent to what was observed with FLSC analyzed in parallel. As expected, antibodies C11 and A32 did not react with TcSC as the bulk of their respective epitopes were deleted from the TcSC construct.

The binding of gp120 and CD4 sequences in the single-chain molecules should also block exposure of epitopes in the CD4 binding site on gp120. To confirm that such binding had occurred, that the CD4 binding site of gp120 was no longer available for binding, FLSC and TcSC were evaluated using the Mab45 capture format and a series of monoclonal antibodies (IgG1b12, F91, and 205-469) directed against the CD4 binding domain (CD4bd) on gp120.

Figure 5C:
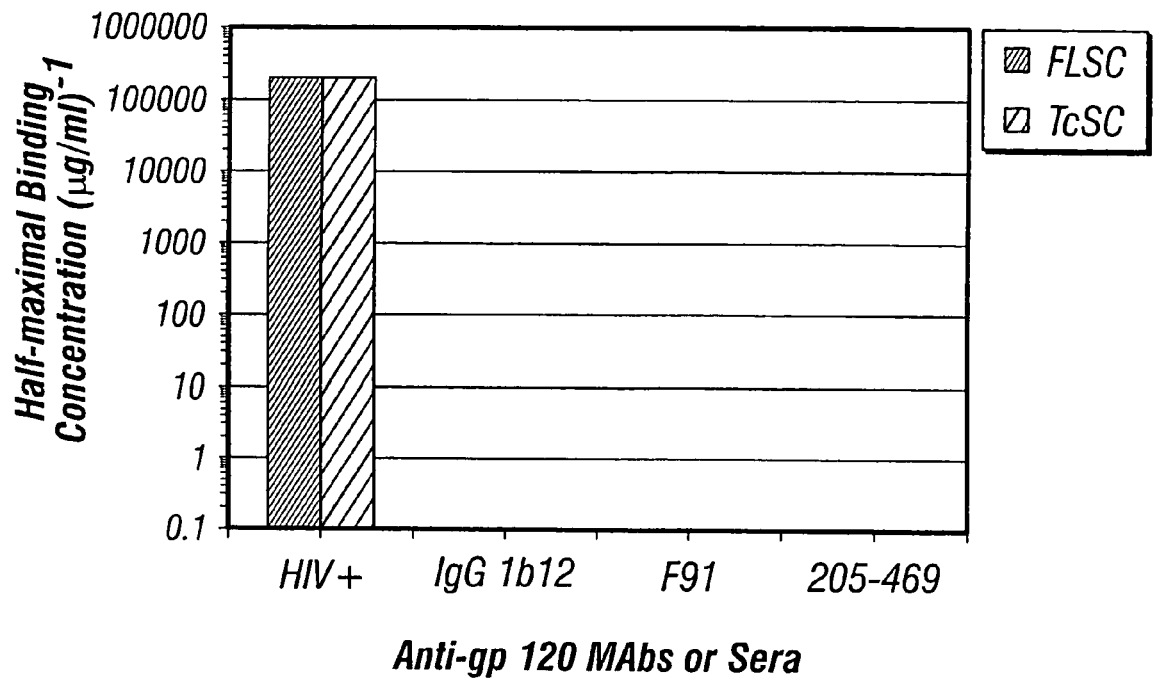

As shown in FIG. 5C, none of these antibodies reacted with either FLSC or TcSC, although positive reactivity was observed with pooled HIV+ sera tested in parallel. This data indicates an interaction between CD4 sequences and the gp120 CD4 binding domain present within FLSC and TcSC molecules.

In sum, these results demonstrate that gp120-CD4 chimeric polypeptide reactivity was comparable to that observed with complexes made by combining soluble gp120 and CD4 (uncrosslinked), and higher than with gp120 alone. These data indicate that the single-chain gp120-CD4 molecules formed interacting complexes similar to the transition state HIV envelope-CD4 complex. The captured gp120-CD4 was also reactive with anti-CD4 antiserum and anti-myc antibody in other ELISA studies, consistent with the western blot analyses. Taken together, these data indicate that a majority of the single-chain gp120-CD4 molecules represent properly folded gp120-CD4 complexes.

EXAMPLE IV

This Example describes data demonstrating the binding of gp120-CD4 chimeric molecules, containing a CCR5-specific HIV envelope sequence, to CCR5 expressing cells.

The formation of the gp120-CD4 complex normally exposes the envelope domains that interact with an appropriate co-receptor (M. Thali et al., *J. Virol.*, 67:3978-86 (1993); M. A. Vodicka et al., *Virol*., 233: 193-8 (1997)). Therefore, another measure of properly folded gp120-CD4 complexes and its ability to inhibit virus infection of a cell is the ability to bind to a CCR5 co-receptor.

To evaluate the ability of the single-chain complexes to bind co-receptor, purified single-chain gp120-CD4 molecules were allowed to interact with cells that express either CCR5 or CXCR4. Briefly, supernatants containing gp120-CD4 single-chain were generated by transient transfection of 293 cells with pEF6-SC. Supernatants were then added to an immunoaffinity column of A32 and the purified single-chain eluted with 0.2 M Acetic Acid pH 2.5, and analyzed by D7324-capture ELISA and by immunoblot, as described. Fractions containing single chain were collected, equilibrated to pH 7, and concentrated.

For the binding, the purified single-chain preparation was allowed to interact with L1.2 cells that express CCR5 (L. Wu et ul., *Nature*, 384: 179-183 (1996); L. Wu et al., *J. Exp. Med*., 186: 1373-8 1 (1997)). L1.2, L1.2/X4, and L 1.2/R5 cells, murine B-cells lines that express no co-receptor, CXCR4, or CCR5 were mixed with decreasing concentrations of purified single-chain protein. After incubation at 37° C. for 1 hour, the cells were washed. Bound single-chain molecules were detected with 1 ug/ml of MAb C11 (J. E. Robinson et al., *J.*

Cell. Biochem. Suppl., 16E:71 (1992); M. Thali et al., J. Virol., 67:3978-86 (1993), an anti-gp 120 MAb, followed by an anti-human IgG that was labeled with a fluorescent molecule, phycoerythrin. C11 recognizes a conformational determinant formed by the C1-C4 regions. The level of bound fluorescence was determined by fluorescence activated cell sorting (FACS) analysis with a FACS Calibur instrument (Becton Dickinson). The mean fluorescence intensity for each sample was calculated using the Cell Quest 3.1.3 program (Becton Dickinson).

Figure 6:
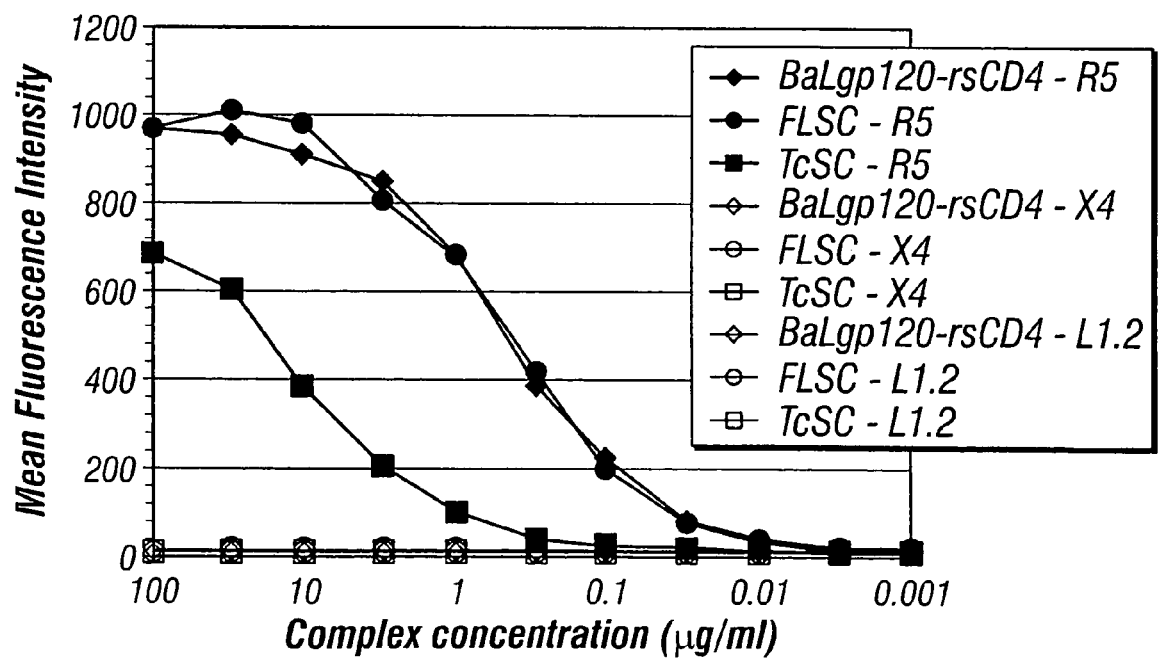
FIG. 6 is an analysis of gp120-CD4 chimera (FLSC, TcSC) binding to CCR5 (R5) or CXCR4 (X4) co-receptor expressing L1.2 cells. Control cells that do not express CCR5 or CXCR4 are denoted L1.2. Bound complexes were detected by flow cytometry using 5 ug/ml of anti-CD4 Mab45. The values shown are of a representative study performed three times.
Figure 7:
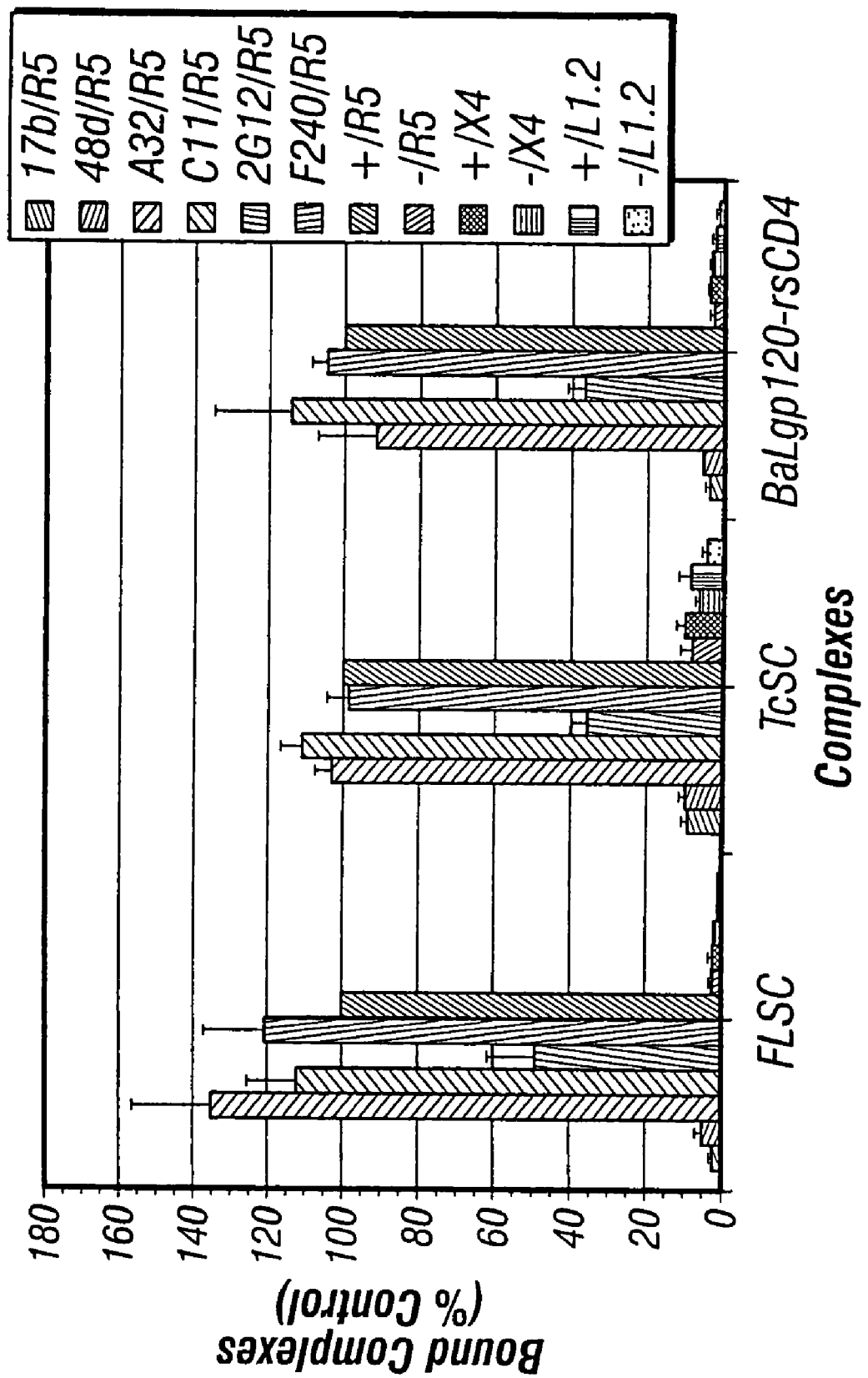
FIG. 7 is an analysis of gp120-CD4 (FLSC, TcSC) binding to co-receptor in the presence of gp120 binding antibodies (17b, 48d, A32, C11 and 2G12), and a gp41 antibody (F240). L1.2 cells expressed co-receptor CCR5 (R5), CXCR4 (X4), or no co-receptor (L1.2), as indicated. Antibody-free controls are denoted "+." Background measurements obtained with untreated cells are denoted "−." Bound complexes were detected by flow cytometry using 5 ug/ml Mab45. Results are presented as percent binding relative to the mean fluorescence intensity obtained in the matched control assay. Average values derived from three separate studies are shown. Standard errors are shown with bars.
Figure 8:
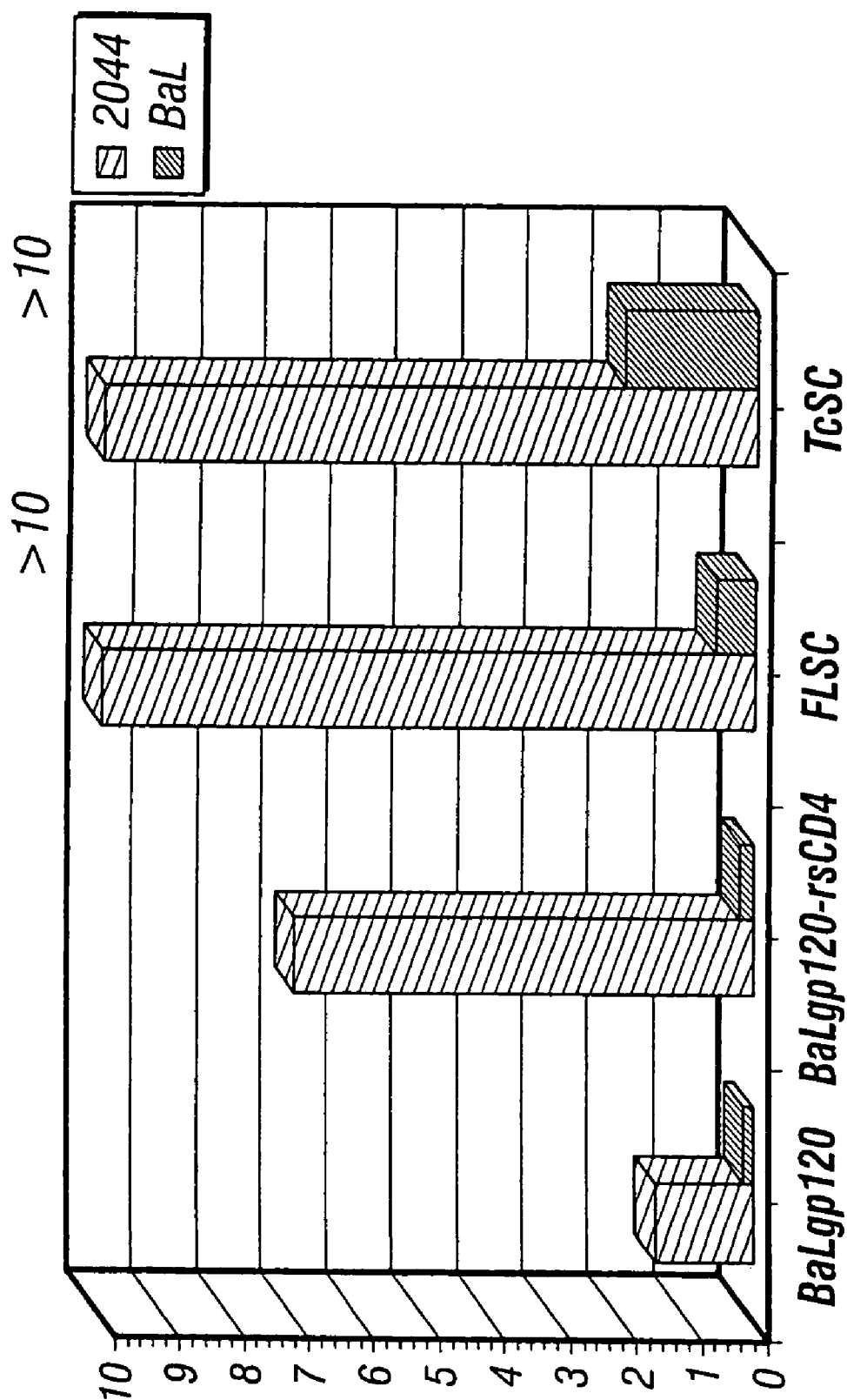
FIG. 8 is an analysis of HIV-$1_{2044}$ (an X4-specific isolate) and HIV-$_{Ba1}$, (an R5-specific isolate) virus neutralization by FLSC, TcSC, BaLgp120 and BaLgp120-rsCD4 complexes. U373 cells expressed CD4, either R5 or X4, and P-galactosidase regulated by the HIV-1LTR promoter. An $ID_{90}$ for FLSC and TcSC against HIV-1$_{2044}$ was not achieved with the maximum concentrations tested and is therefore presented as >10 ug/ml.

As shown in FIG. 6, both single chain gp120-CD4 complexes (FLSC and TcSC) bound to the CCR5-expressing, but not CXCR4-expressing, L1.2 cells. Maximal binding was observed with FLSC at concentrations (10 ug/ml) equivalent to what was observed with soluble BaL gp120-rsCD4 complexes tested as controls. In comparison, approximately 10-fold higher concentrations of the TcSC were required to approach saturation binding. Thus, gp120-CD4 chimeric polypeptide presents functional co-receptor binding site(s) for CCR5, as expected for a molecule containing a macrophage tropic gp120.

The absence of binding to CXCR4 in these studies was not entirely unexpected in view of the apparent specificity of the HIV envelope polypeptide in the gp120-CD4 chimera for CD4. Thus, by constructing polypeptide chimeras that bind to CXCR4 or other co-receptors, or by modifying a virus coat polypeptide, as described herein, to obtain a chimeric polypeptide that binds to another co-receptor, other virus coat polypeptide-receptor polypeptide chimeras can be obtained that bind to other co-receptors.

To demonstrate that single-chain gp120-CD4 is binding to CCR5 through its co-receptor binding site, competition binding studies with 17b and 48d antibodies, which have been shown to interact with the co-receptor binding site of gp120 and prevent gp120/sCD4 complexes from interacting with co-receptor expressing cells, were performed. For controls, another gp120 antibody, C11, and a gp41 antibody F240, was used. All of these antibodies are derived from HIV-1 infected patients . Each antibody was used at 10 ug/ml and added together with 3 ug/ml of purified single-chain molecule to L1.2 cells that express either CCR5 or CXCR4. Bound gp120-CD4 was detected with C11, followed by anti-human IgG labeled with PE. The amount of gp120-CD4 was determined by FACS and expressed as a percentage of the total bound in control wells without competing antibody.

As shown in FIG. 7, 17b and 48d strongly inhibited the binding of both single-chain complexes to the cells. In the presence of these antibodies, the binding signal on CCR5-expressing cells was the same as the background binding seen with L 1.2/CXCR4 and L1.2 parental cells. Interestingly, 2G12, a potent neutralizing antibody, also reduced the interaction of all complex forms with CCR5. In comparison, anti-gp120 antibodies recognizing epitopes outside the co-receptor binding domain, C 11, A32, and an anti-gp41 antibody, F240, all failed to reduce the binding of FLSC or TcSC to the CCRS-expressing L1.2 cells.

These results indicate that the gp120 co-receptor binding site is important for binding to co-receptor. These results also indicate that agents that inhibit binding/interaction between gp 120-CD4 and co-receptor can be identified using such an assay. Such agents may have potential value as therapeutics.

In sum, the data demonstrate the successful expression of a soluble, chimeric polypeptide which duplicates the transition state conformation of a virus coat-receptor complex. Given this accomplishment, it is now possible to employ the chimeric polypeptide or polynucleotides encoding the polypeptide for immunization of a subject to produce an immune response to virus or virus having similar coat polypeptide epitopes. The immune response produced can be an antibody (humoral) or CTL response. In addition, given the fact that the chimeric polypeptide binds to an appropriate co-receptor on the surface of living cells, the polypeptide can be administered to subjects acutely exposed to an immunodeficiency virus in order to passively protect cells expressing the co-receptor from virus infection.

EXAMPLE V

This example describes data demonstrating that a gp 120-CD4 chimeric molecule can neutralize infection by HIV strains using the same co-receptor. The single-chain molecules were further examined for their ability to neutralize R5 and X4 viruses. A total of $10^4$ U373/CD4/MAGI cells (M. A. Vodicka et al., *Virology*, 233: 193-8 (1997)) expressing either CCR5 or CXCR4 were allowed to attach overnight to flat-bottom tissue culture wells. Culture medium was then removed and replaced with 100 ul of fresh media containing various concentrations of chimeric protein. An additional 100 ul of media containing 50 $TCID_{50}$ of virus was then added to the culture. The entire mixture was then incubated at 37° C. until syncytia were visible, typically within 3-5 days. Culture wells were then treated with a P-galactosidase chemiluminescent reagent, Galatostar (Tropix, Bedford, Mass.), according to the manufacturer's protocol. Virus infection was determined as a function of chemiluminescence, quantified using a Victor$^2$ fluorescence plate reader (EG&G Wallac, Gaithersburg, Md.). Background signal was determined in assays carried out in the absence of virus. Signals obtained for the test assays were then corrected by subtracting the background value. Percent infection was calculated by dividing the corrected relative light units for each experimental well by the corrected light units for control wells containing only cells and virus. The 90% inhibitory dose ($ID_{90}$) values were determined from plots of test protein concentration versus percent inhibition of infection. All test conditions were carried out in triplicate.

As shown in FIG. 8, both FLSC and TcSC potently and selectively neutralized the R5 HIV-1 BaL isolate, while there was only a slight inhibition ($ID_{90}$>10 ug/ml) of 2044 isolate. In comparison, uncomplexed BaLgp120 inhibited entry of both HIV-1BaL and X4 (HIV-12044) viruses as expected due to its direct interactions with CD4. Thus, the data demonstrate that a virus coat polypeptide-receptor chimeric molecule can bind to a cellular co-receptor thereby blocking binding or infection of the cells by virus that utilize the co-receptor for binding or infection.

EXAMPLE VI

This Example describes the construction and expression of a modified gp120-CD4 chimeric polypeptide having an immunoglobulin polypeptide sequence, gp120-CD4-IgG1. This exemplary heterologous domain adds functionality to the gp120-CD4 chimeric polypeptide, including adhesin and immunopotentiating functions, prolonging stability, increasing circulating half-life and ability to cross the placental barrier. This example also shows that the gp120-CD4-IgG1 chimera binds to co-receptor expressed on the surface of intact cells and neutralizes HIV virus. Gp120, a subunit of the envelope protein of HIV-I binds to CD4 and undergoes a conformational change that permits the complex to interact with a co-receptor, such as CCR5. This interaction permits the infection of HIV-1 into target CD4+ cells. Antibodies or other agents that interfere with the interaction of HIV-1 with the co-receptor can prevent infection.

To identify such agents, single-chain gp120-CD4 was modified by fusion to the constant regions that form the IgG1 heavy chain, hinge CH2 and CH3 (FIG. 9). Gp120-CD4-IgG1 can be used to identify agents that block, inhibit, or disrupt HW-1 interaction with the co-receptor, thereby identifying agents that inhibit HIV infection. The gp120-CD4-IgG1 polypeptide comprising SEQ ID NOs: 24, 11, 26 and 32 could also be used as a passive immunotherapeutic to prevent HIV infection after an acute exposure, such as a needlestick injury.

Figure 10:
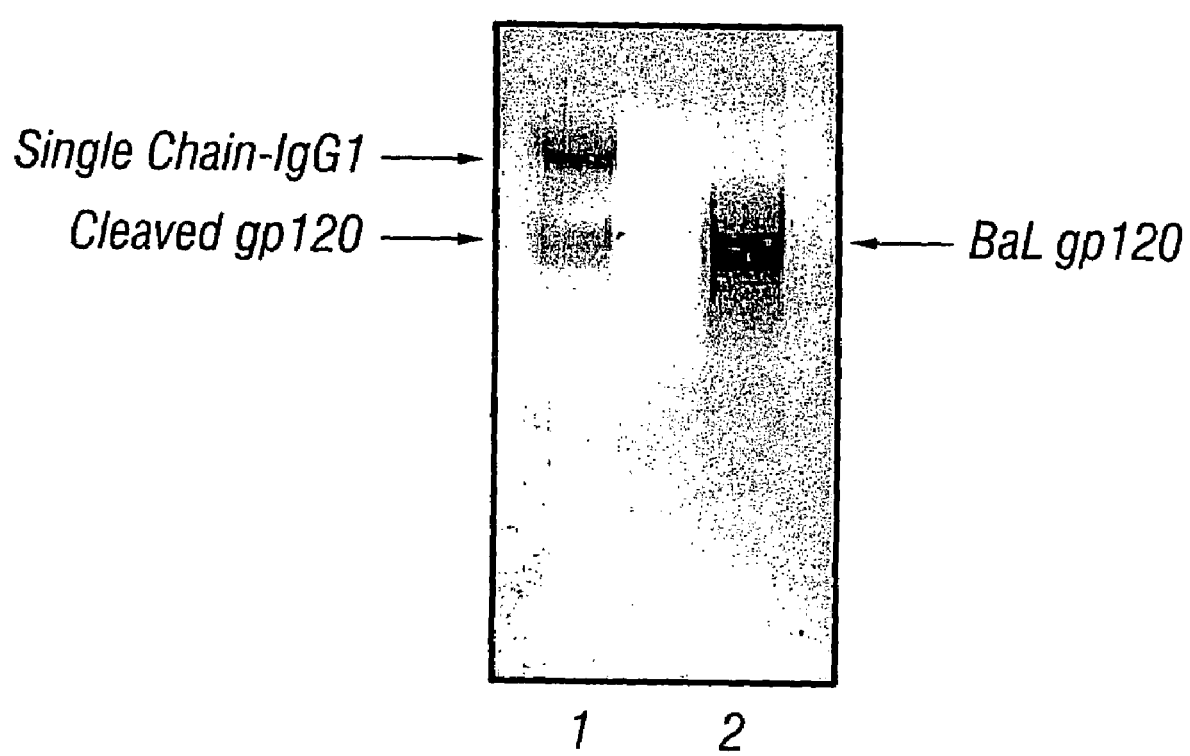
FIG. 10 is an immunoblot analysis of a gp120-CD4-IgG1 chimeric polypeptide expressed in 293 cells. The chimeric gp120-CD4-IgG1 was isolated from culture supernatant (lane 1) and is shown in comparison to purified HIV strain BaL gp120 polypeptide (lane 2). Cleaved gp120 is indicated by the arrow and co-migrates with purified gp120.

Two hundred ninety-three cells were transiently transfected with the plasmid containing gp120-CD4-IgG1 comprising at least SEQ ID NOs: 23, 25 and 31, and the expressed protein was characterized by immunoblotting of the culture supernatants. Briefly, collected supernatant samples were electrophoresed onto a 4-20% gradient PAGE gel. Fractionated proteins were transferred to nitrocellulose and detected with a mixture of anti-gp120 monoclonal antibodies. As shown in FIG. 10, the transiently transfected cells expressed gp 120-CD4-IgG1 (lane 1). Supernatant from cells expressing purified gp120 derived from HIV-1 BaL (lane 2) was electrophoresed for relative size comparison. The gp120-CD4-IgG1 polynucleotide encodes a protein having the predicted size for a gp120-CD4-IgG1 heavy-chain chimera. Like the original gp120-CD4, a portion of gp120-CD4-IgG1 is cleaved producing a 120 kDa protein fragment that is most likely gp120 ("Cleaved gp120"). The size of this fragment suggests that gp120-CD4-IgG1 is being cleaved within the spacer. To assure that the gp120-CD4-IgG1 is folded into a conformation permissive for binding co-receptor, dilutions of the supernatant were added to L 1.2 cells that express either CCR5 or CXCR4 co-receptors. Bound gp120-CD4-IgG1 was detected with anti-human IgG that was labeled with Europium, a fluorescent reagent. The amount of fluorescence is directly related to the amount of bound material.

Figure 11:
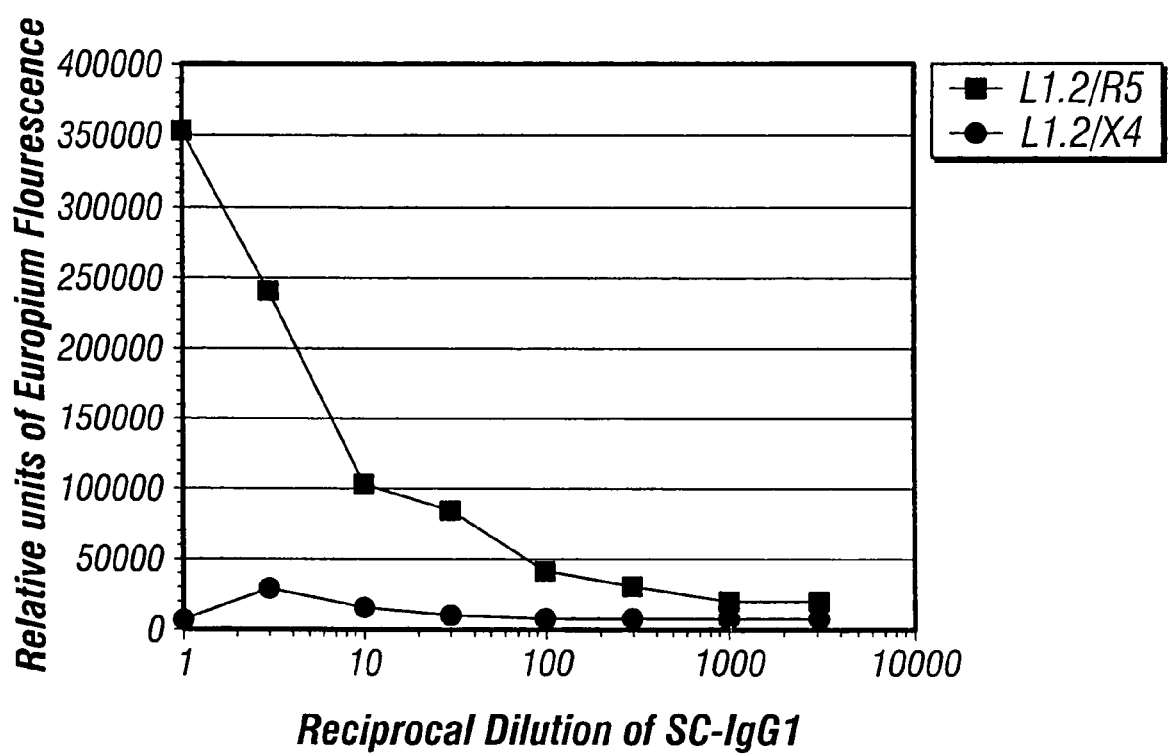
FIG. 11 is a reciprocal dilution analysis of gp120-CD4-IgG1 chimeric polypeptide binding to co-receptor expressing L1.2 cells. CCR5 and CXCR4 expressing L1.2 cells are as indicated.

As shown in FIG. 11, gp120-CD4-IgG1 binds specifically to L 1.2 cells that express CCR5. Again, little binding to CXCR4 was detected using this assay, which is consistent with the results for gp120-CD4. These studies indicate that heterologous domains conferring additional or enhanced functionality can be added to chimeric molecules without affecting their ability to form a complex that binds to cell co-receptor. To confirm that binding of chimeric gp120-CD4-IgG1 heavy chain to CCR5 expressing cells was mediated by co-receptor binding site of gp120, binding was studied in the presence of blocking antibody 17b. Briefly, for the MAb/FLSC-IgG1 competition studies, sodium butyrate activated L1.2 cells expressing co-receptor were added to V-bottom plates at $10^5$/well. 10 ug/ml FLSC-IgG1 and 1 ug/ml MAbs were added to the cells.

Cells and protein were incubated together for 1 hour at 37° C. Cells were pelleted and washed with TBS three times. Bound material was detected with phytoerytherin-labeled anti-human IgG at 5 ug/ml for 1 hour at 4° C. The cells were washed three times with TBS then analyzed by fluorescence-activated cell sorting (FACS).

Figure 12:
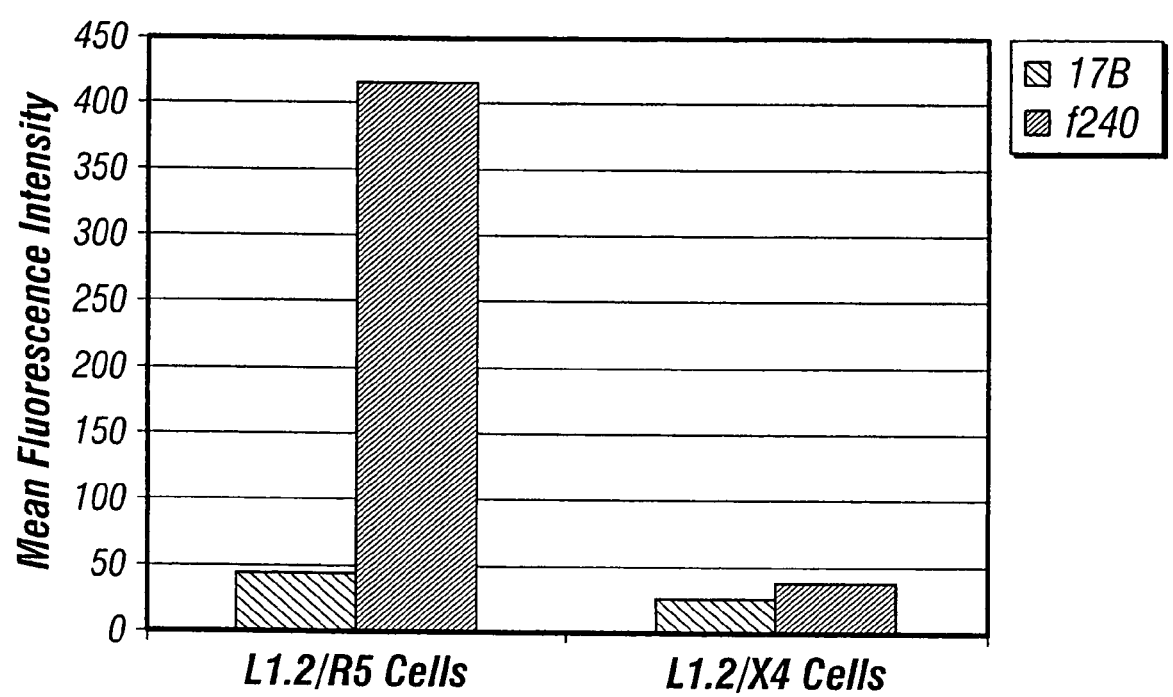
FIG. 12 is an analysis of a blocking MAb (17b) on FLSC-IgG1 binding to CCR5 expressing cells showing that FLSC-IgG1 interacts with the R5 co-receptor via the R5-binding domain on gp120.

As shown in FIG. 12, 17b, an antibody that recognizes the CCR5-binding domain on gp120, blocks FLSC-IgG1 interaction with L1.2R.5 cells while control antibody, F240, does not. These data demonstrate that the FLSC-IgG1 interacts with the R5 co-receptor via the R5-binding domain on gp120. To confirm that chimeric gp120-CD4-IgG1 heavy chaicould block virus entry into cells, neutralization assays were then performed. In brief, U373/CD4/MAGI cells that xpress either CCR5 or CXCR4 were allowed to attach to flat-bottom tissue culture trays overnight at $10^4$ cells/well. The medium was removed and varying concentrations of MAbs and immunoadhesins were then added to cells in 100 ul of media. Virus (50 $TCID_{50}$/well of in 100 ul of media) was then added and the mixture incubated at 37° C. until syncytia were visible, typically 3-5 days. Plates were read using a P-galactosidase chemiluminescent reagent, Galatostar, according to the manufacturer's protocol and the chemiluminescence produced was quantified using a $Victor^2$ as previously described. Percent virus growth was calculated by using the relative light units for (experimental well)—background wells with no virus)/(wells with virus but no protein)—(background wells) (Table 2). $ID_{50}$ and $ID_{90}$ were determined graphically.

TABLE 2

Neutralization of X4, R5, and X4/R5 HIV by FLSC-IgGl

| | U373/CD4/CCR5 | | | | |
|---|---|---|---|---|---|
| | FLSC-IgGl | 2G12 | 2F5 | 1 IgGlbl2 | Control 1gG |
| | | ID90 (ug/mL) | | | |
| BaL | 3.1 | >10 | >10 | 1.57 | >10 |
| ADA | 4.58 | >10 | >10 | >10 | >10 |
| 89.6 | 3.56 | 8.07 | >10 | 3.39 | >10 |
| | U373/CD4/CXCR4 | | | | |
| | SClg | 2G12 | 2F5 | IgGlbl2 | Control 1gG |
| | | ID90 (ug/mL) | | | |
| 2044 | >10 | >10 | >10 | 1.57 | >10 |
| 2005 | >10 | >10 | >10 | >10 | >10 |
| 89.6 | >10 | >10 | >10 | 5.34 | >10 |

The data in Table 2 indicate that FLSC-IgG blocks viruses that use R5 for cell entry.

FLSC-IgG neutralizes virus as effective as 2G12, 2F5, and IgG1b12, antibodies that are currently being evaluated in passive immunotherapy trials. These data therefore further affirm the usefulness of gp120-CD4 chimeras to inhibit HIV infection in particular, and the applicability of virus coat protein-receptor chimeras as inhibitors of other viruses that utilize co-receptor for binding or cell penetration in general.

EXAMPLE VII

This Example describes data demonstrating that mutation of the furin cleavage site improves the stability of the FLSC complex. The position of the cleavage site that separates the FLSC fragments is probably located within the C terminal gp 120 sequences present only in FLSC, since the shorter TcSC did not exhibit degradation. Notably, these sequences encompass the gp120 gp41 junction normally cleaved by the furin protease (M. Girard et al., *C R Acad Sci III.*, 322:959-66) (1999)). Cleavage of the FLSC at the natural furin site would be consistent with the behavior of the FLSC fragments, as it would have minimal impact on the structures of the gp120 and CD4 moieties and their capacity to interact.

Figure 13:
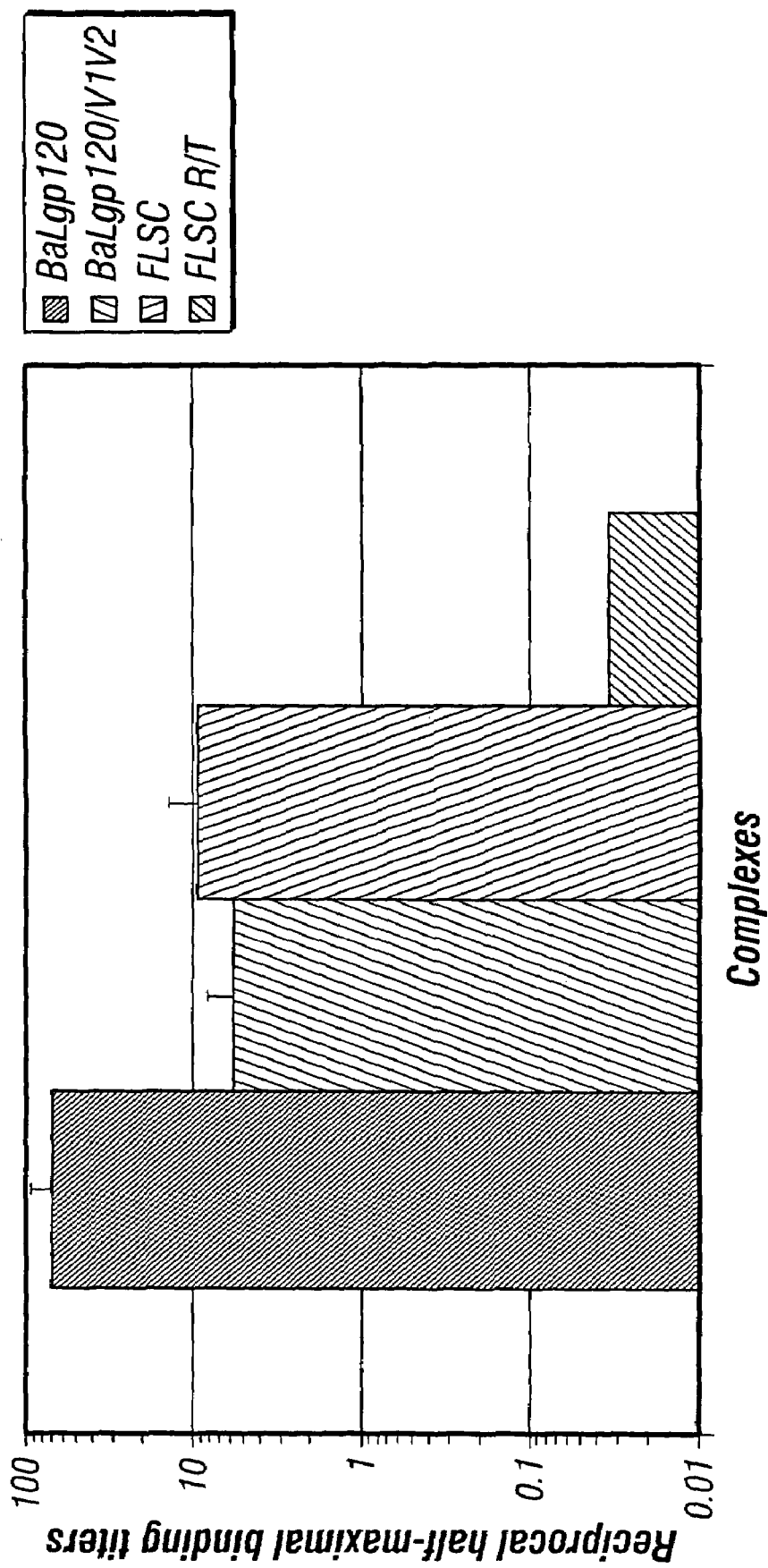
FIG. 13 shows the improved stability of gp120-CD4 (FLSC) molecules following mutation of furin cleavage site (R-T).

In order to determine if this putative furin site accounts for cleavage, BaLgp120, BaLgp120 complexed with an sCD4 molecule consisting of the first two domains (V1V2) of CD4, FLSC, and FLSC R/T were captured onto plastic via an antibody specific for the C-terminus of gp120 (antibody binding was unaffected by the R/T mutation). Four domain V1-V4 sCD4 were titrated onto the captured complexes starting at 30 ug/ml. Four domain sCD4 has a higher affinity for gp120 than the two domain V1V2 and, therefore, would compete off the smaller unit from complexes. Bound four domain CD4 was detected with antibody OKT4, which only binds the four domain CD4. The results in FIG. 13 show that mutation of the furin cleavage site prevents the V1 V2 found on the FLSC R/T from dissociating as readily as the cleaved FLSC, thus improving its stability of the FLSC R/T complex. Introduction of the R?T mutation into the BaLgp 120 c-terminus eliminates the furin mediated cleavage observed with the FLSC. Reducing this cleavage improves the continuity of the linker sequence and improves the stability of the FLSC construct (see FIG. 13) by increasing the local concentration of the gp120 and CD4 moieties. The experimental result of this increase is the reduction in the ability of the soluble four domain CD4 to compete with the two domain CD4 found on the FLSC R/T.

EXAMPLE VIII

This Example describes the transfection of cells with the polynucleotide encoding the gp120-CD4 modified chimeric polypeptide and the characterization of the expressed soluble polypeptide. Recombinant pEF6-FLSC, pEF6-RLSC-R/T, pEF6-FLSC-R/T CD4M9 and pEF6-BaLgp120 were transfected into 293 cells using Fugene, according to the manufacturer's protocol (Boehringer-Manheim). Stable transfectants were obtained by selection with 5 ug/ml blasticidin. Briefly, cell culture supernatants containing the chimeric polypeptides were collected and boiled in SDS-PAGE loading buffer (75 mM Tris, 2% SDS, 10% glycerol, 0.001% bromphenol blue, pH 8.3). The samples were then electrophoresed in a 4-20% SDS-polyacrylamide gradient gel. The gel-fractionated proteins were then transferred to a nitrocellulose membrane. Non-specific binding sites on the membrane were then blocked for 30 minutes with 2% non-fat dry milk in tris-buffered saline, pH 7. The membrane was then probed with a mixture of murine monoclonal antibody against HIV gp120 and bound antibodies were detected with alkaline phosphatase labeled goat anti-mouse IgG.

Figure 14:
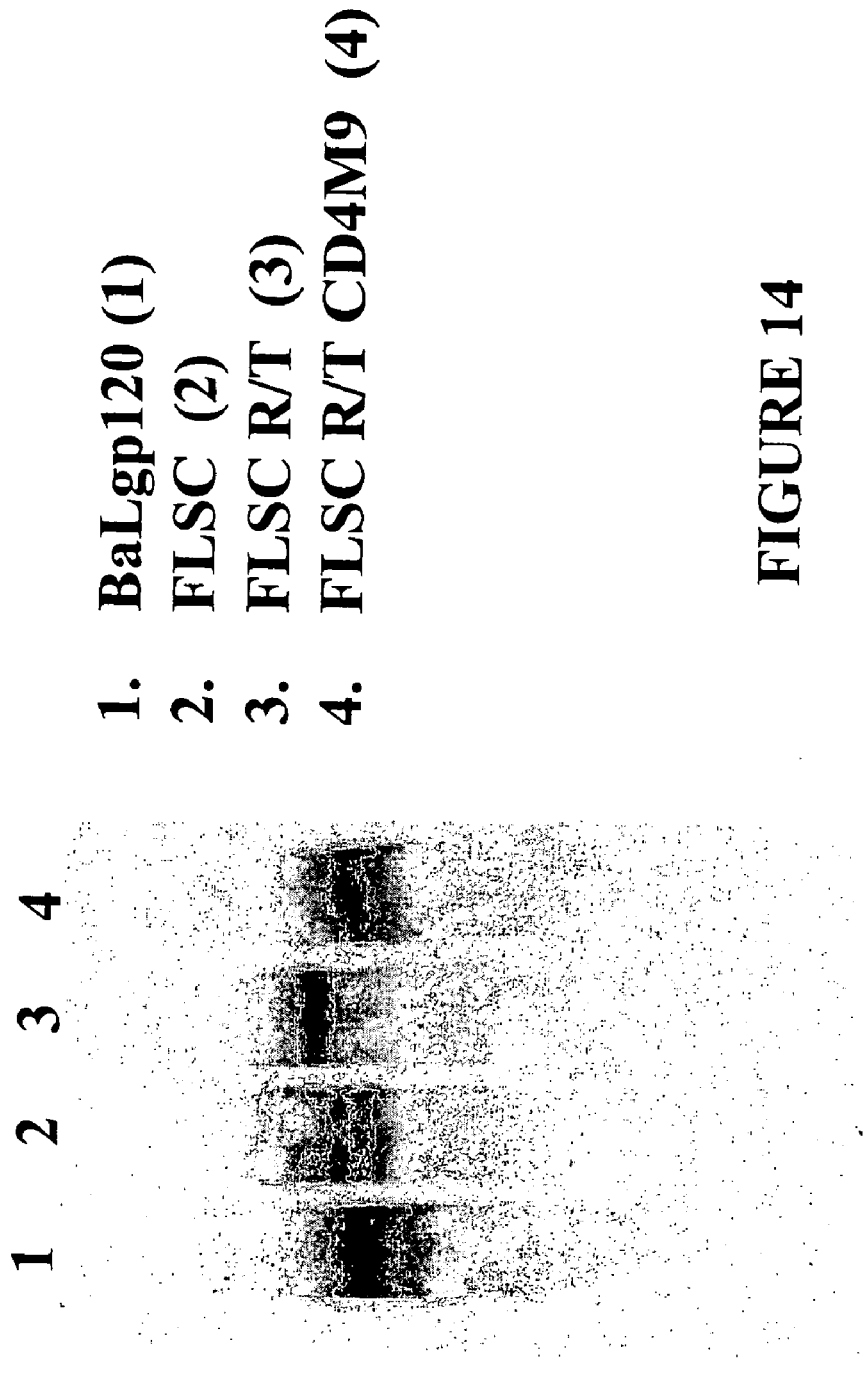
FIG. 14 shows an immunoblot comparing FLSC R/T CD4M9 with BaLgp120, FLSC, and FLSC R/T. The FLSC R/T CD4M9 was constructed by switching the CD4 D1D2 sequence in FLSC R/T for a CD4M9 gene sequence.

As shown in FIG. 14, the BaLgp120 (Lane 1) and the FLSC-R/T CD4M9 (Lane 4) migrated with an approximate molecular weight of 120 kDa. While the FLSC R/T CD4M9 is predicted to be approximately 130 kDa, the difference of 10 kDa is difficult to see on this blot. The FLSC (lane 2) is a 150 kDa protein that is cleaved at the furin site at the c-terminus of the protein. This cleavage separates the gp120 and CD4 components of the FLSC. The lower 120 kDa band is the result of this cleavage. The released CD4 component is not visible on this blot because the antibodies used to detect the proteins were specific for gp120. The apparent cleavage of the single-chain molecules into gp120 and CD4 moieties under certain conditions might be a concern for DNA vaccines, since such processing could potentially occur in vivo.

This Example describes data demonstrating that mutation of the furin cleavage site improves the stability of the FLSC complex. The position of the cleavage site that separates the FLSC fragments is probably located within the C terminal gp12O sequences present only in FLSC. Notably, these sequences encompass the gp120/gp41 junction normally cleaved by the furin protease (M. Girard et al., C R Acad Sci III., 322:959-66 (1999)). Cleavage of the FLSC at the natural furin site would be consistent with the behavior of the FLSC fragments, as it would have minimal impact on the structures of the gp120 and CD4 moieties and their capacity to interact. The results show that mutation of the furin cleavage site prevents the V1 V2 found on the FLSC R/T from dissociating as readily as the cleaved FLSC, thus improving the stability of the FLSC R/T complex. As a result, the R/T mutation used to create FLSC R/T minimizes this cleavage and stabilizes the protein.

EXAMPLE IX

This Example describes data demonstrating the binding of gp120-CD4 chimeric polypeptide to an antibodies reactive with gp120 and CD4. The binding of gp120 to CD4 causes conformational changes in the molecule leading to the exposure of the co-receptor-binding domain. Therefore, antibodies directed against epitopes in this domain should react strongly with properly folded single-chain molecules. In order to determine exposed epitopes in chimeric molecules, antigenic properties of BaLgp120, FLSC, FLSC-R/T and FLSC-R/T CDM9 molecules were compared. Detection was accomplished using monoclonal antibodies 17b previously shown to preferentially bind gp120 after engagement of CD4 (M. Thali et al., J. Virol., 67:3978-86 (1993)), followed by the appropriate-labeled second antibody. The antibody 17b, a human monoclonal antibody that recognizes an epitope that becomes increasingly exposed when gp120 interacts with CD4 and binds within the co-receptor attachment site (CCR5). (N. Sullivan et al., J. Virol., 72:4694-703 (1998); A. Trkola et al, Nature, 384: 184-6 (1996); L. Wu et al., Nature, 384: 179-183 (1996)). Antibodies were diluted in BLOTTO and incubated for 1 hour at room temperature. Plate were washed three times with TBS between each incubation step. The amounts of gp120 sequences present in samples were determined based on a standard curve generated with commercial recombinant HIV gp120 (Bartels, Issaquah, Wash.). The antibody was adsorbed to plastic at 1 ug/ml and wells blocked with BLOTTO. Assays were then carried out as above using the indicated human monoclonal antibodies.

Figure 16:
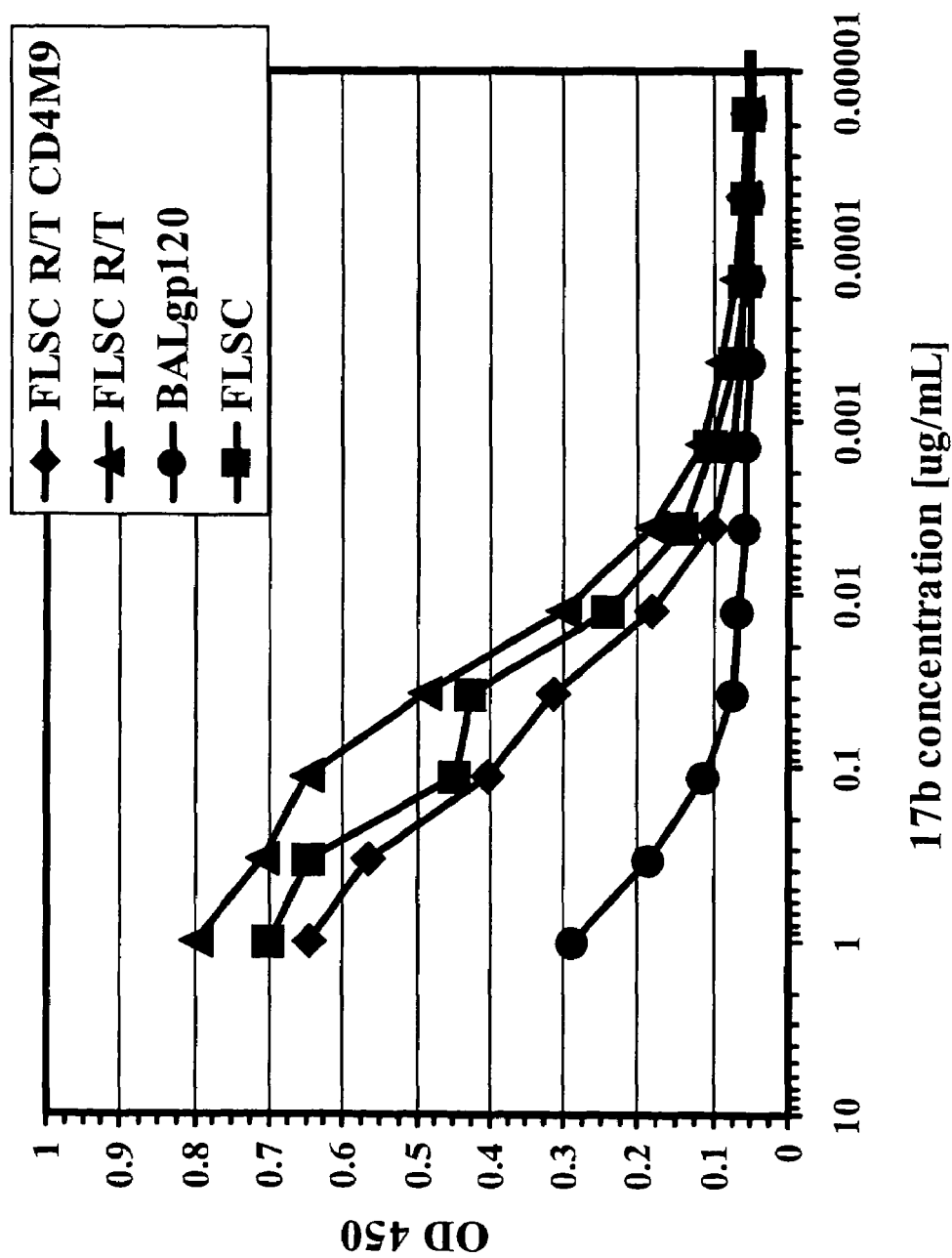
FIG. 16 shows the binding of an epitope that becomes increasing exposed when gp120 interacts with CD4 and that the 17b epitope that is exposed is FLSC R/T CD4M9 and equivalent to that of FLSC R/T.

As shown in FIG. 16, the binding curves of 17b with BaLgp120, FLSC, FLSC-R/T and FLSC-R/T CDM9 molecules were enhanced by binding of 17b to FLSC-R/T or FLSC chimeric proteins both of which contain both gp120 and CD4. 17b also binds to FLSC-R/T CD4M9 with the efficiency equivalent to that of FLSC-R/T indicating that the 17b epitope is exposed in the FLSC-R/T CD4M9 protein. Taken together, these data indicate that the single chain gp120-CD4 molecules FLSC, FLSC-R/T and FLSC-R/T CDM9 represent properly folded gp120-CD4 complexes.

EXAMPLE X

This Example describes data demonstrating the binding of gp120-CD4 chimeric molecules, containing a CCR5-specific HIV envelope sequence, to CCR5 expressing cells. The formation of the gp120-CD4 complex normally exposes the envelope domains that interact with an appropriate co-receptor (M. Thali et al., J. Virol., 67:3978-86 (1993); M. A. Vodicka et al., Virol., 233: 193-8 (1997)). Therefore, another measure of properly folded gp120-CD4 complexes and its ability to inhibit virus infection of a cell is the ability to bind to a CCR5 co-receptor.

To evaluate the ability of the single-chain complexes to bind co-receptor, purified single-chain gp120-CD4 molecules were allowed to interact with canine thymocytes, Cf2Th, that either express CCR5 or have no co-receptor. Briefly, supernatants containing gp120-CD4 single-chains chimeric polypeptides FLSC-R/T and FLSC-R/T CDM9 molecules were generated by transient transfection of 293 cells with pEF6.

Figure 15:
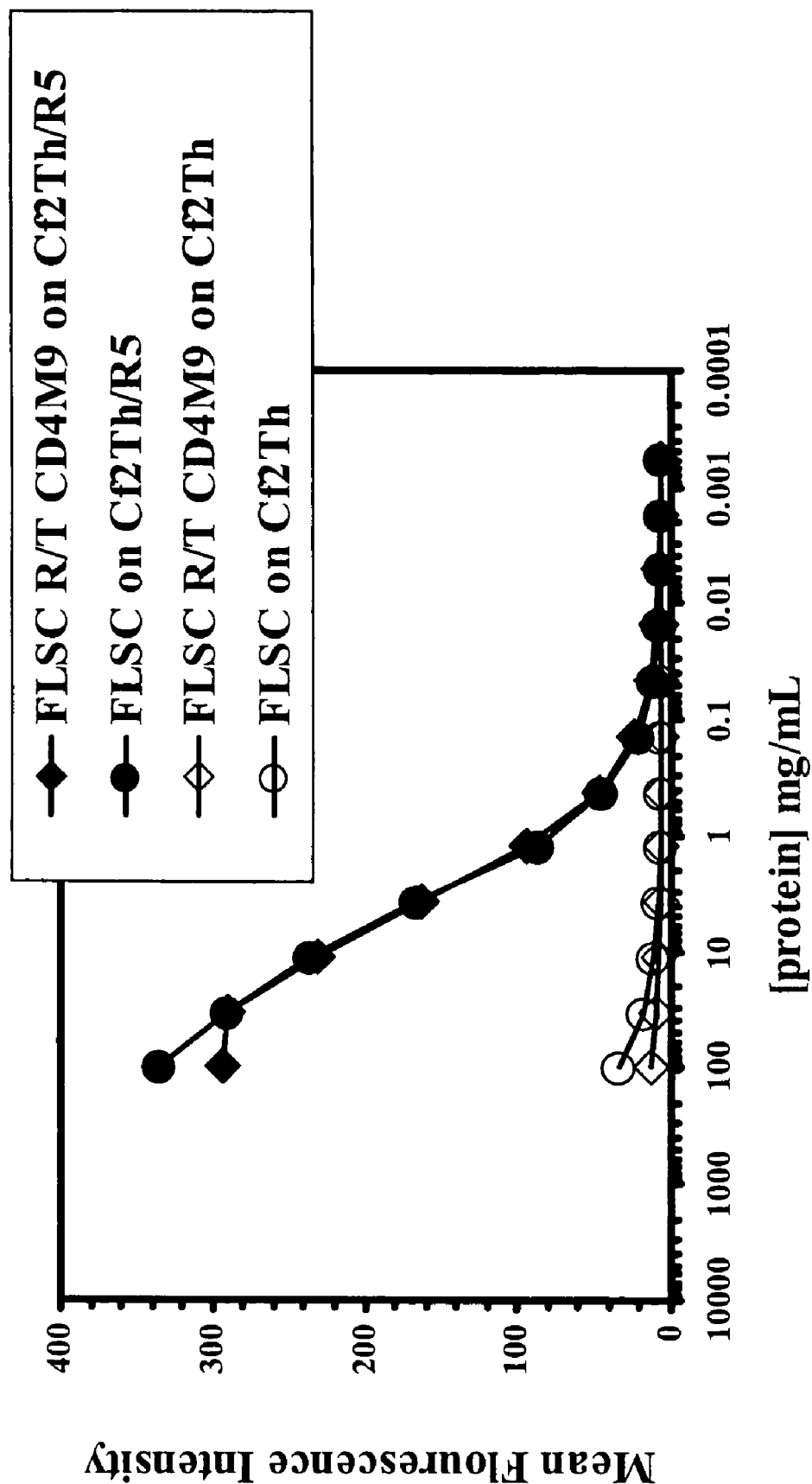
FIG. 15 is an analysis of FLSC R/T CD4M9 binding to CCR5 (R5). Results of the analysis are shown as mean fluorescence intensity. The figure shows that the FLSC R/T CD4M9 binds to R5 expressing cells with an efficiency equivalent to that of FLSC R/T.

For the binding, the purified single-chain preparation was allowed to interact with canine thymocytes that express CCR5 or have no co-receptor. Bound single-chain molecules were detected with anti-gp120 MAb, A32, followed by PE-labeled goat anti-human IgG that was labeled with a fluorescent molecule, phycoerythrin. The level of bound fluorescence was determined by fluorescence activated cell sorting (FACS) analysis with a FACS Calibur Instrument (Becton Dickinson). The amount of fluorescence is directly related to the amount of bound material. The mean fluorescence intensity for each sample was calculated using the Cell Quest 3.1.3 program (Becton Dickinson). The results shown in FIG. 15 show that the FLSC-R/T CD4M9 bind to the CCR5 expressing cells but not to cells without a co-receptor with the efficiency equivalent to that of FLSC-R/T.

EXAMPLE XI

This example describes neutralization of primary R5 HIV-1 (92BR020) by sera from FLSC-inoculated mice. C587B1/6 mice were inoculated four times with 25 ug of FLSC per mouse mixed with 10 ug cholera toxin (CT). Inoculation occurred at two week intervals. 14 days after the last inoculation, sera from the individual mice were collected and assayed for neutralizing activity against primary R5 HIV-1 isolate 92BR020. Serial dilutions of sera starting at 1:2 were mixed with 50 $TCID_{50}$ infection doses of virus/well and $10^4$ U373/CD4/R5/MaGI cells/well. After 24 hours, the sera, virus and media were replaced with 200 ul of fresh media. The assay was allowed to incubate for 5 days until syncytia were visible. Growth of HIV-1 was indicated by production of b-galactosidase in cell lysates as measured using a chemiluminescent reagent, Galactostar (Tropix) according to manufacture's protocol. Virus infection was determined as a function of chemiluminescence, quantified using a $Victor^2$ (EG&G Wallac, Gaithersburg, Md.) fluorescence plate reader. Background signal was determined with assays carried out in the absence of virus and sera. Signal obtained for the test assays were then corrected by subtracting the background value. The percent invention was calculated by dividing the corrected relative light units for each experimental well by the corrected light units for control wells containing only cells and virus. Sera from the FLSC inoculated mice are labeled #0, #1, #2, #3, #4, and naive mouse is labeled "C".

Figure 17:
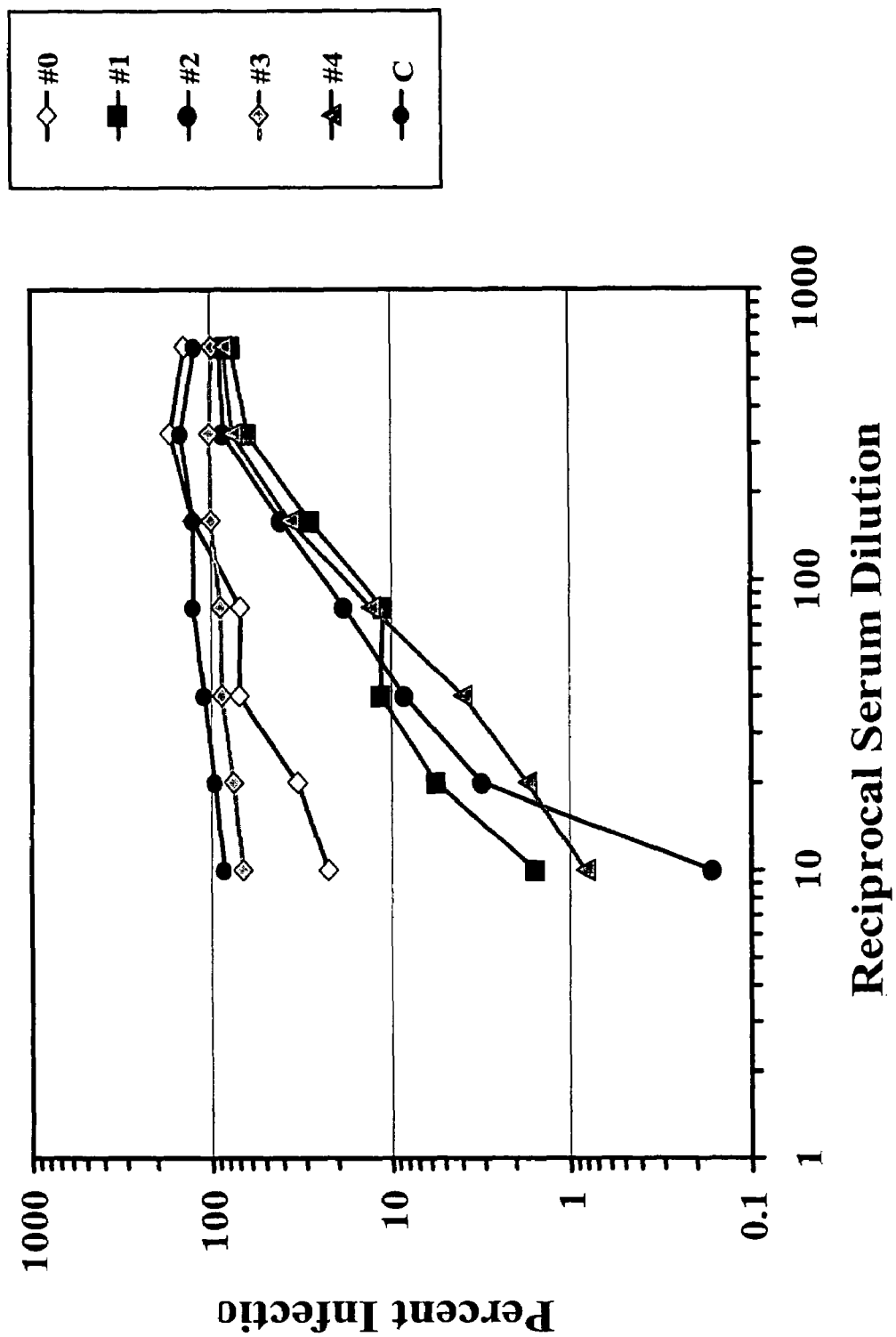
FIG. 17 shows neutralization of primary R5 HIV-1 (92BR020) by sera from FLSC inoculated mice.

As shown in FIG. 17, as the dilution factor is increased there is also an increase in virus infection. Additionally, the sera isolated from control mouse showed no effect on virus infection, while high concentrations of sera from mouse #2 showed a minimal amount of virus infection.

In sum, the data demonstrate the successful expression of a soluble, chimeric polypeptide which duplicates the transition state conformation of a virus coat-receptor complex. Given this accomplishment, it is now possible to employ the chimeric polypeptide or polynucleotides encoding the polypeptide for immunization of a subject to produce an immune response to virus or virus having similar coat polypeptide epitopes. The immune response produced can be an antibody (humoral) or CTL response. In addition, given the fact that the chimeric polypeptide binds to an appropriate co-receptor on the surface of living cells, the polypeptide can be administered to subjects acutely exposed to an immunodeficiency virus in order to passively protect cells expressing the co-receptor from virus infection.

EXAMPLE XII

Figure 18:
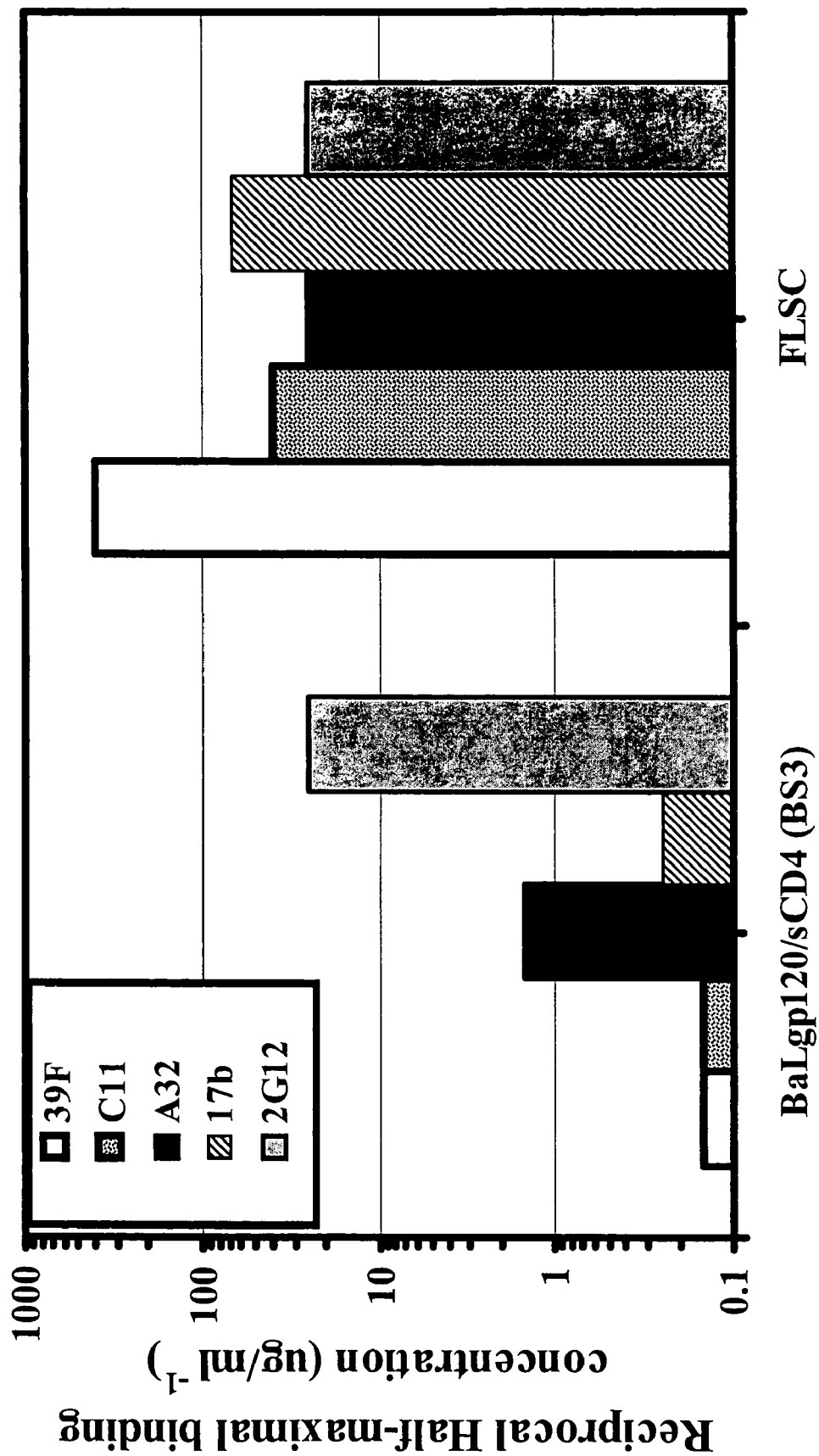
FIG. 18 shows covalent crosslinking of BaLgp120/sCD4 complexes occludes epitopes that are exposed on FLSC.

FLSC and complexes of BaLgp120 and sCD4 were captured onto D7324-coated ELISA plates. D7324 is a sheep polyclonal IgG that is reactive to the C-terminal region of gp120 and is an antibody that is commonly used to examine the antigenicity of HIV-1 envelope proteins by capture-ELISA. BaLgp120/sCD4 complexes were then crosslinked for 30 mins with 0.5 mM Bis(sulfosuccinimidyl)suberate (Pierce), then treated with 10 mM Tris-HCL to stop the reaction. BaLgp120/sCD4 & FLSC plates were then washed with TBS. Monoclonal antibodies against the V3 loop (39F), C1-C5 (C11), C1-C4 (A32), coreceptor binding domain (17b), and C3-V4 (2G12) regions of BaLgp120 were titrated onto the captured antigens. Bound antibodies were detected with goat-anti-human IgG labeled with horse-radish peroxidase. FIG. 18 shows that the crosslinking reaction alters the structure of the BaLgp120/sCD4 complex and reduces the antigenicity of the 39F, C11, A32 and 17b epitopes. In contrast, these epitopes are not occluded on the FLSC. This antigenic alteration would impact the function of these epitopes. For instance, the epitope recognized by 17b interacts with the R5 coreceptor. Occlusion of this epitope by the crosslinker would reduce the ability of the crosslinked complex to interact with the coreceptor. This observation would also suggest that that crosslinked complex could not be used to screen for reagents that may potentially block HIV-1 via its coreceptor.

EXAMPLE XIII

Figure 19:
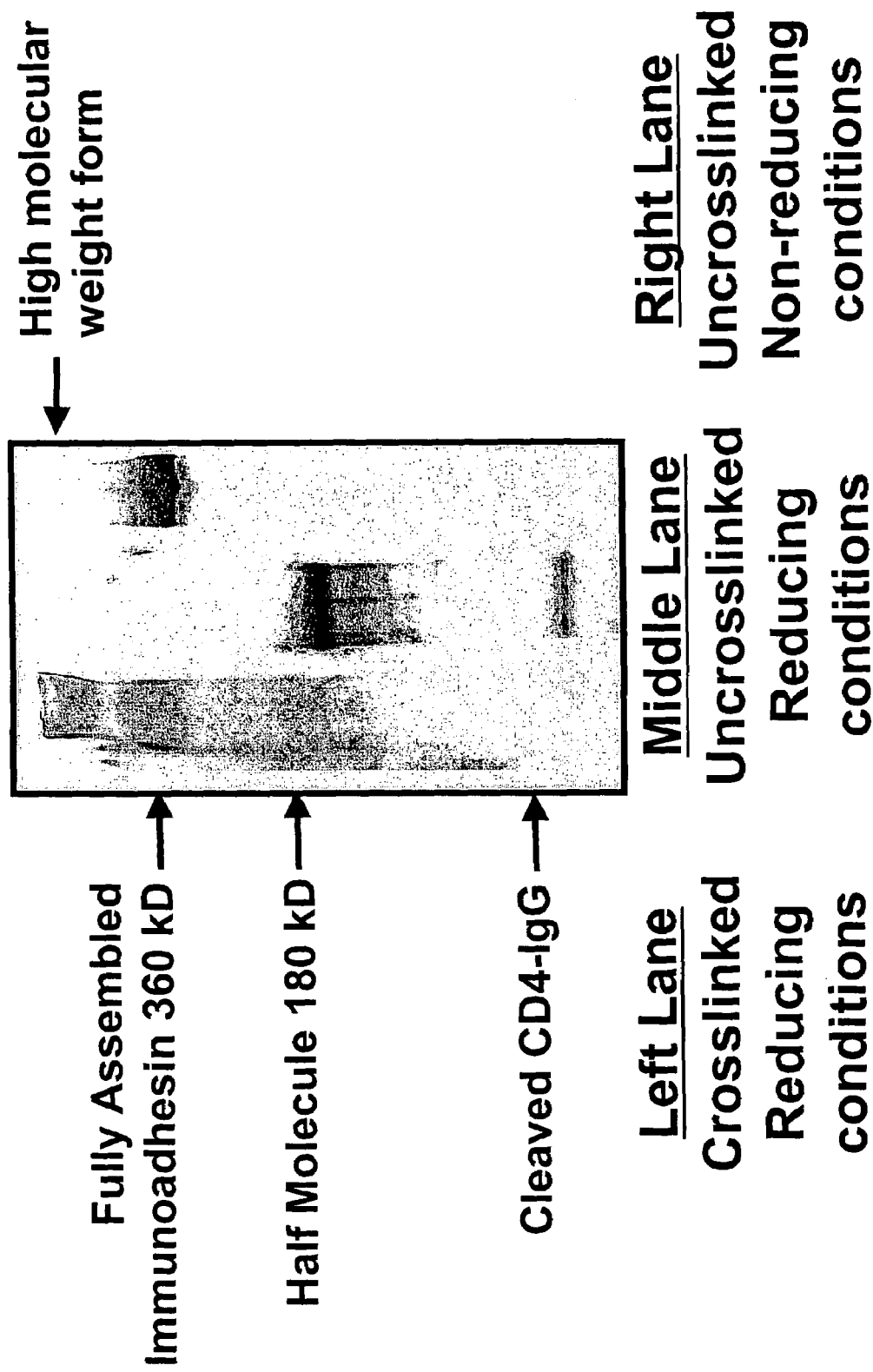
FIG. 19 shows an immunoblot comparing purified R/T FLSC-IgG1 in reducing and non-reducing conditions.

Purified R/T FLSC-IgG1 was crosslinked for 30 mins with 0.5 mM Bis(sulfosuccinimidyl)suberate (Pierce), then treated with 10 mM Tris-HCL to stop the reaction. Crosslinked material was then compared to uncrosslinked material run in reducing and non-reducing SDS-PAGE conditions. As shown in FIG. 19, the uncrosslinked material on the reducing gel (middle lane) runs at 180 kDa, the expected size of the BaLgp120-CD4-IgG1 chimera. The smaller band is the appropriate size of CD4-IgG indicating that the chimera is cleaved between the BaLgp120 and the CD4-IgG portion of the molecule. This observation suggests that although the R/T mutation eliminates the cleavage due to furin-protease, another protease can act on the c-terminus of gp120. The uncrosslinked material in non-reducing conditions (right lane) runs at 360 kDa, the predicted size of the fully assembled immunoadhesin. This observation indicates that while a portion of the material is cleaved (see middle lane) immunoadhesin remains associated. Crosslinking of the material, which stabilizes the assemble structure, confirms this observation (left lane). Here the material runs approximately 360 kDa as expected. A higher molecular weight form is also visible suggesting that a portion of purified preparation is aggregated.

Figure 20:
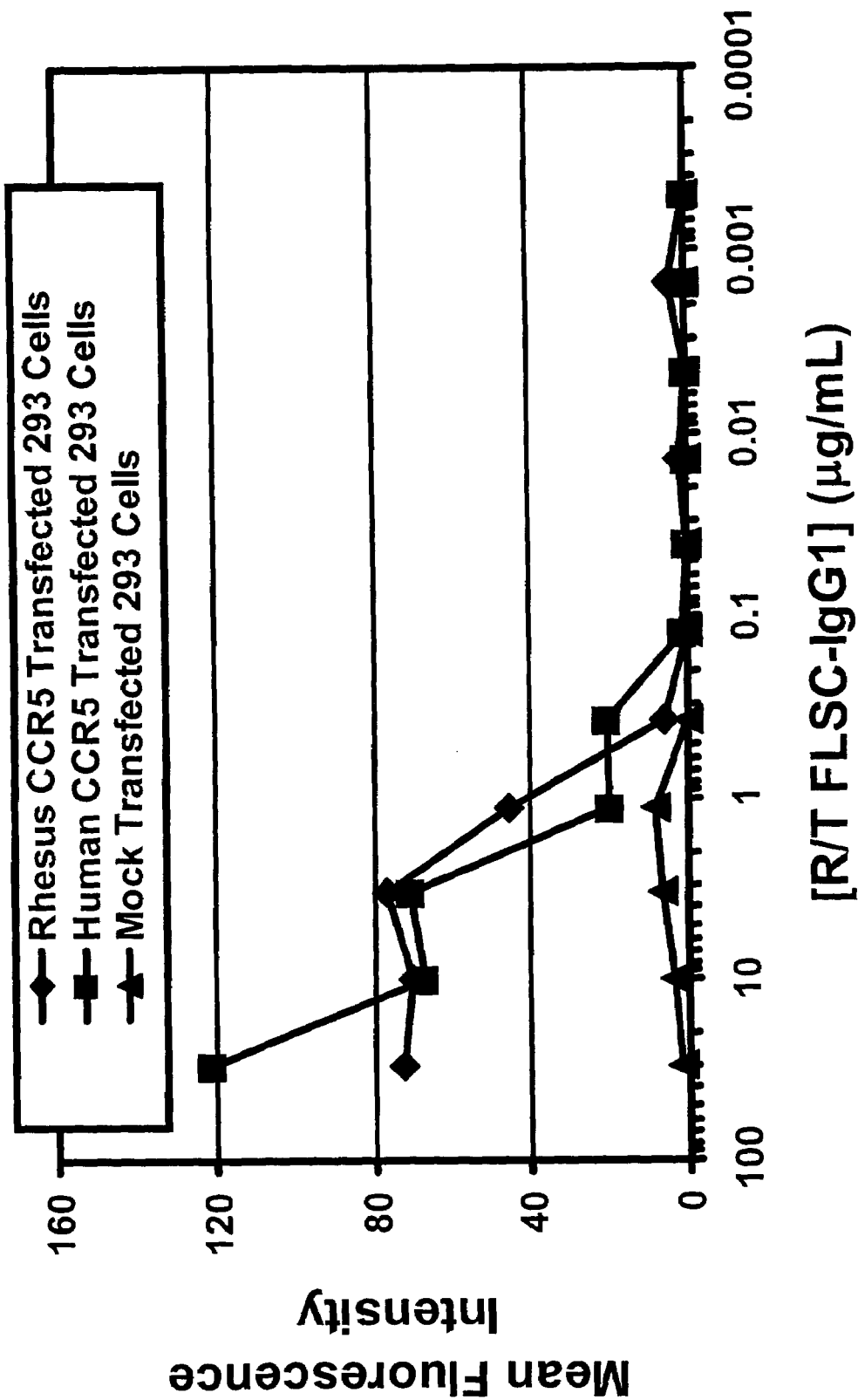
FIG. 20 shows binding of R/T FLSC-IgG1 to both human and rhesus CCR5.

EXAMPLE XIV 293 cells were transiently transfected either pcDNA-human CCR5 or pcDNA-rhesus CCR5 or no plasmid 24 hrs prior to use. Transfected cells ($10^5$/well) were incubated at 37° C. for 1 hr with the indicated concentration of R/T FLSC-IgG1. Bound R/T FLSC-IgG1 was detected with phycoerythrin conjugated Goat anti-human IgG and analyzed by FACS. FIG. 20 shows that R/T FLSC-IgG1 binds to both human and rhesus CCR5.

Figure 21:
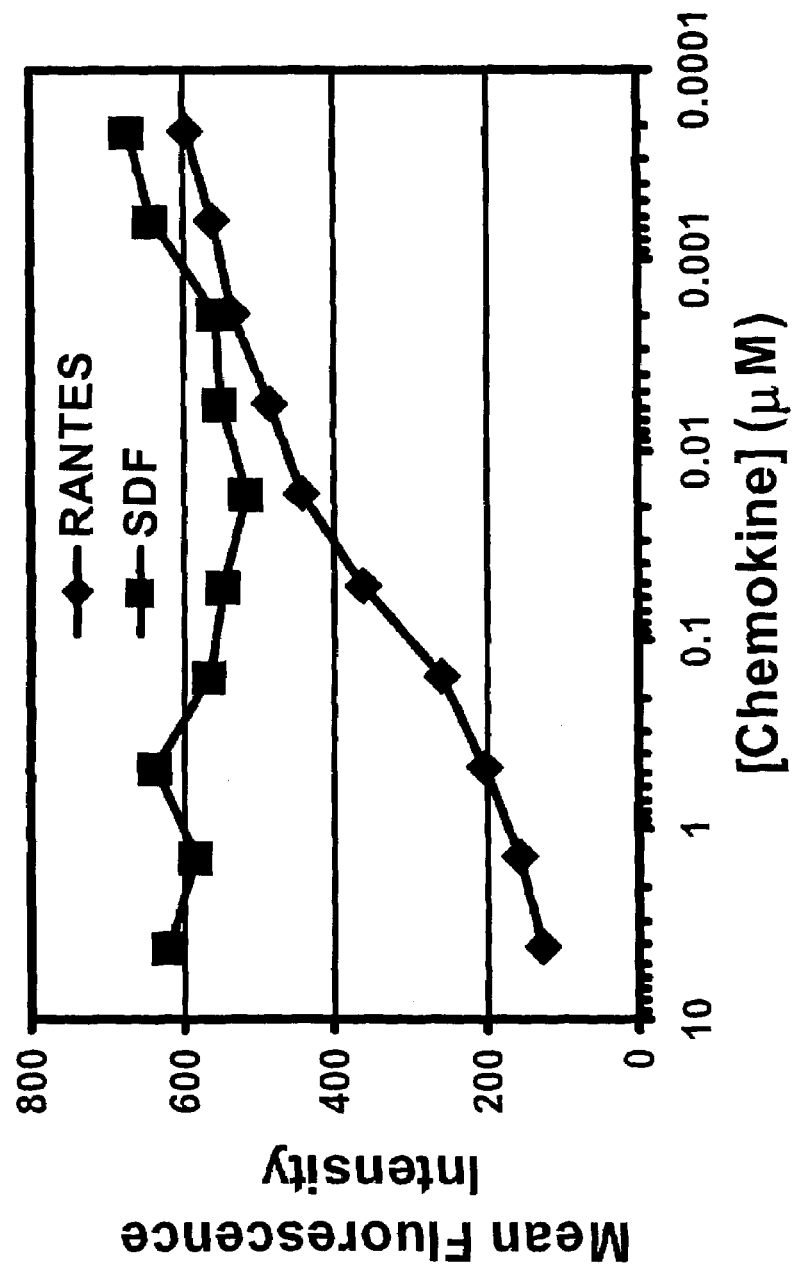
FIG. 21 shows RANTES competitively inhibits R/T FLSC-IgG1 binding to CCR5.

Canine thymocytes expressing CCR5 (CF2Th-R5) ($10^5$) were incubated with 3 ug/mL R/T LSC-IgG1 and the indicated concentration of chemokine for 1 hr at 37° C. Bound R/T FLSC-IgG1 was detected using phycoerythrin conjugated goat anti-human IgG and analyzed by FACS. RANTES is a CCR5-specific chemokine and as expected competes with R/T FLSC-IgG1 for the receptor. SDF, a CXCR4-specific chemokine, was used a control. FIG. 21 provides further proof that the R/T FLSC-IgG1 may be used as a screening tool to define reagents that may block HIV-1 infection via its coreceptor, CCR5.

All references cited herein are incorporated by reference herein for all that they teach and for all purposes. It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

That which is claimed is:

1. A polynucleotide sequence comprising a nucleic acid sequence encoding a chimeric polypeptide selected from the group consisting of SEQ ID NO: 13, SEQ ID NO: 2, SEQ ID NO: 4 and SEQ ID NO: 6.

2. A polynucleotide sequence comprising a nucleic acid sequence encoding a chimeric polypeptide comprising:

a virus coat polypeptide sequence and a viral receptor polypeptide sequence, wherein the coat polypeptide sequence and the receptor polypeptide sequence are linked by an amino acid spacer of sufficient length to allow the coat polypeptide sequence and the viral receptor polypeptide sequence to bind to each other wherein the virus coat polypeptide sequence is selected from the group consisting of SEQ ID NO: 24, SEQ ID NO: 30, and SEQ ID NO: 28.

3. The polynucleotide sequence according to claim 2, where the receptor polypeptide sequence is selected from the group consisting of SEQ ID NO: 26 and SEQ ID NO: 20.

4. The polynucleotide sequence according to claim 1, wherein the nucleic acid sequence is selected from the group consisting of SEQ ID NO: 1, SEQ ID NO: 3, SEQ ID NO: 5 and SEQ ID NO: 12.

5. The polynucleotide sequence according to claim 2, wherein a nucleic acid sequence for the virus coat polypeptide is selected from the group consisting of SEQ ID NO: 23, SEQ ID NO: 29 and SEQ ID NO: 27.

6. The polynucleotide sequence according to claim 5, wherein a nucleic acid sequence for the receptor polypeptide is selected from the group consisting of SEQ ID NO: 25 and SEQ ID NO: 19.

7. The polynucleotide sequence according to claim 6, further comprising a nucleotide sequence encoding for a heterologous domain.

8. The polynucleotide sequence according to claim 7, wherein the heterologous domain is an IgG or domains thereof.

9. An expression vector comprising at least one nucleotide sequence selected from the group consisting of SEQ ID NO: 1, SEQ ID NO: 3, SEQ ID NO: 5, SEQ ID NO: 12, SEQ ID NO: 23, SEQ ID NO: 29, SEQ ID NO: 27, SEQ ID NO: 25 and SEQ ID NO: 19.

10. An isolated host cell containing the expression vector of claim 7.

11. A method for identifying an agent that inhibits an interaction between a virus and a virus receptor comprising the steps of: (a) contacting the chimeric polypeptide selected from the group consisting of SEQ ID NO: 24, SEQ ID NO: 30, and SEQ ID NO: 28, with a test agent; and (b) detecting binding between the virus coat polypeptide sequence and the viral receptor polypeptide sequence, wherein a decreased amount of binding in the presence of the test agent identifies an agent that inhibits binding between the virus and the virus receptor.

* * * * *

UNITED STATES PATENT AND TRADEMARK OFFICE
CERTIFICATE OF CORRECTION

PATENT NO. : 7,399,473 B2
APPLICATION NO. : 11/124027
DATED : July 15, 2008
INVENTOR(S) : Anthony L. Devico et al.

Page 1 of 1

It is certified that error appears in the above-identified patent and that said Letters Patent is hereby corrected as shown below:

Column 1, line 19: "may have" should be -- has --

Signed and Sealed this
Eleventh Day of January, 2011

David J. Kappos
*Director of the United States Patent and Trademark Office*